US008504384B2

United States Patent
Mancini et al.

(10) Patent No.: US 8,504,384 B2
(45) Date of Patent: *Aug. 6, 2013

(54) METHOD AND ARTICLE OF MANUFACTURE FOR PERFORMING CLINICAL TRIAL BUDGET ANALYSIS

(75) Inventors: Ieda A. Mancini, Philadelphia, PA (US); Ann S. Vurimindi, Philadelphia, PA (US); Fernando F. Alves, Philadelphia, PA (US); Christopher T. Mather, Rocky Hill, NJ (US)

(73) Assignee: Numoda Technologies, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/870,160

(22) Filed: Aug. 27, 2010

(65) Prior Publication Data
US 2010/0324931 A1 Dec. 23, 2010

Related U.S. Application Data

(63) Continuation of application No. 12/121,822, filed on May 16, 2008, now Pat. No. 7,788,114.

(60) Provisional application No. 60/939,059, filed on May 19, 2007.

(51) Int. Cl.
*G06Q 10/00* (2006.01)
*G06Q 50/00* (2012.01)

(52) U.S. Cl.
USPC ............... 705/2; 705/3; 705/4; 707/100

(58) Field of Classification Search
USPC ................... 705/1–4, 400; 707/100
See application file for complete search history.

(56) References Cited

U.S. PATENT DOCUMENTS

| 5,890,129 | A * | 3/1999 | Spurgeon ............ 705/4 |
| 5,991,741 | A * | 11/1999 | Speakman et al. ....... 705/30 |
| 7,054,823 | B1 * | 5/2006 | Briegs et al. ........... 705/2 |
| 2005/0071348 | A1 * | 3/2005 | Laicher et al. ......... 707/100 |
| 2005/0171918 | A1 | 8/2005 | Eden et al. |
| 2006/0282244 | A1 * | 12/2006 | Chotai et al. .......... 703/11 |
| 2007/0100885 | A1 | 5/2007 | Sumino et al. |
| 2007/0255587 | A1 | 11/2007 | Chien et al. |

* cited by examiner

*Primary Examiner* — Michelle Le
(74) *Attorney, Agent, or Firm* — Panitch Schwarze Belisario & Nadel LLP

(57) ABSTRACT

An electronic method and article of manufacture is provided for analyzing clinical trial budgets. A clinical trial budget is input into a processor. The budget includes activities and associated activity costs of a clinical trial. The activities of the inputted clinical trial budget are classified into a set of standardized service categories. The processor is used to electronically allocate the associated activity costs with the respective standardized service category so that budget costs of the clinical trial can be objectively analyzed. A report of the associated activity costs with the respective standardized service category is outputted for use in analyzing budgets for clinical trials.

18 Claims, 164 Drawing Sheets

Result: 1) Pay more than necessary for some activities 2) Budget overruns due to required activities not listed, nor budgeted, but charged to client as pass-through costs 3) Poor vendor performance 4) Gaps in service cause increased risk of clinical trial delay and failure

Figure 2

| Report | Lack of analysis and awareness of budgets | Analysis provides improved information |
|---|---|---|
| 20 A. Differences of overall assumption specifications | There is no easy way to compare assumption specifications | Information is pulled from hundreds of pages of data regarding activities, standardized and displayed in comparison columns, or marked as not detailed |
| 20 B. Difference of LOAACs costs | Some budgets include costs in professional fees categories and some in pass through expenses so that without awareness of these factors, one can make false assumptions | Standardized activities are sorted into standard categories, making it possible to make decision based on more accurate information |
| 20 C. Cost Equalization | Comparisons are made based on total prices, yet most totals are inaccurate, are missing items, and have gaps in activities | Information on the total price has been corrected to have the costs of missing items and gaps corrected |
| 20 D. Cost Equalization assumptions specifications 1 | When different assumption specifications need to be analyzed, all CROs who responded with a budget need to do a second budget | An equalization is made to one or more set of assumptions so decisions can be more immediate |
| 20 E. Cost Equalization assumptions specifications 2 | Several different assumption specifications need to be analyze for one trial and all CROs will need to do as many budgets as are required | An equalization can be made to any set of assumption specifications. This makes it possible to evaluate many different option quickly. |
| 21 Detail of Differences – metrics (assumption specifications) | Although budget costs may be similar, or a choice is made to select the lowest priced CRO, it is difficult to know if what is being provided for the budget matches the RFP | When the activities are standardized into standard categories, it is easy to compare. For example it is now easy to see that the line for 'total project duration' from both CROs is different than the RFP |
| 22 A Detail of Differences – financial (costs) | Given the difference in the total standardized professional fees line, it is very time consuming to and often impossible to perform all the algorithms and calculations that it takes to | With the costs placed into standard categories, at a glance, one can see that monitoring and project management are the activities that are nearly seven times different |

Process Overview

Standardization

Figure 5-A

|   | A | B | C | D |
|---|---|---|---|---|
| 1 |   | Date: | =TODAY() |   |
| 2 |   | Compound: |   |   |
| 3 |   | Sponsor: |   |   |
| 4 |   | Contact: |   |   |
| 5 |   | Study Phase: |   |   |
| 6 |   | Study Title: |   |   |
| 7 |   | Protocol Number: |   |   |
| 8 |   | Contract Initiation Date | =C1+30 |   |
| 9 |   | First Patient Enrolled | =C1+(30*C21) |   |
| 10 |   | Completion of Contract | =C8+(C25*30) |   |
| 11 |   |   |   |   |
| 12 |   | RFP Specifications: |   |   |
| 13 |   | Total Sites | =C14+C15 |   |
| 14 |   | Sites US | 0 |   |
| 15 |   | Sites ROW | 150 |   |
| 16 |   | Patients Screened | 1500 |   |
| 17 |   | Screened to Enrolled Ratio | 5 |   |
| 18 |   | Patients Enrolled | =+C20*C19 |   |
| 19 |   | Enrolled to Completed Ratio | 1 |   |
| 20 |   | Patients Completed | 300 |   |
| 21 |   | Start Up Period | 3 |   |
| 22 |   | Enrollment Period (Months) | 24 |   |
| 23 |   | Treatment Period (Months) | 6 |   |
| 24 |   | Close Out Period (Months) | 3 |   |
| 25 |   | Total Study Length (Months) | =C22+C23+ C21+C24 |   |
| 26 |   | Treatment Period (Weeks) | =C23*4.333 |   |
| 27 |   | Monitoring/Live Period (Weeks) | =(C22+C23)*4.33*I30 |   |
| 28 |   | Study Length (Weeks) | =(C25*4.333) |   |
| 29 |   | Unique CRFs per Patient | 33 |   |
| 30 |   | Repeat CRFs per Patient | 176 |   |
| 31 |   | Total CRF per Patient | =C29+C30 |   |
| 32 |   | CRAs (US) | =I72*0.7 |   |
| 33 |   | CRAs (ROW) | 45 |   |
| 34 |   | Users | =+C13*2.5 |   |
| 35 |   | Tablets/pda | =+C13+2 |   |
| 36 |   | Inv Mtgs US | 1 |   |
| 37 |   | Inv Mtgs ROW | 2 |   |
| 38 |   | Total Inv. Mtgs | =1*(C37+C36) |   |
| 39 |   | Kick off Mtgs US | 1 |   |

Figure 5-B

| | A | B | C |
|---|---|---|---|
| 40 | | Kick off Mtgs ROW | 0 |
| 41 | | Total Kick off Mtgs | =SUM(C39:C40) |
| 42 | | IM/Trainning Staff | 1 |
| 43 | | Support Staff | =0.06*C13 |
| 44 | | Vendor Ini. visits US | 11 |
| 45 | | Vendor Ini. visits ROW | 11 |
| 46 | | Total vendor Ini visits | =SUM(C44:C45) |
| 47 | | | |
| 48 | | Query Rate | 0.14 |
| 49 | | Estimated Queries | =I16*C48 |
| 50 | | Edit Checks | =C51*C29 |
| 51 | | Edit Checks per page | 8 |
| 52 | | Integrations | 3 |
| 53 | | Cust Rpts | 0 |
| 54 | | Standard | 0 |
| 55 | | Configured | 0 |
| 56 | | Meds per Patient | 10 |
| 57 | | Disease/Pt | 10 |
| 58 | | Coded Terms per Patient (AEs) | 10 |
| 59 | | Total Coded Terms | =(C56+C57+C58)*C16 |
| 60 | | SAEs | =C20*0.1 |
| 61 | | SafetyDB | 1 |
| 62 | | SAS Transfers (out) | 3 |
| 63 | | Interim Analysis/Locks | 1 |
| 64 | | IVR Required? | =F20 |
| 65 | | Treatment arms | =2*C64 |
| 66 | | Calls/pt | =1*C64 |
| 67 | | Call Duration | =2.5*C64 |
| 68 | | IVRS Calls for Randomization | =(C18+C13)*C64 |
| 69 | | Number of Randomization Arms | =C65 |
| 70 | | Countries | 9 |
| 71 | | # Languages | 9 |
| 72 | | IVRS (Invt. Meeting) Attendance | 2 |
| 73 | | SIV (US) | =C32 |
| 74 | | SIV (ROW) | =C33 |
| 75 | | Total SIV | =SUM(C73:C74) |
| 76 | | Audited CRFs | =I16*0.1*I39 |
| 77 | | Vendor Audits US | 0 |

Figure 5-C

|   | A | B | C |
|---|---|---|---|
| 75 |   | Total SIV | =SUM(C73:C74) |
| 76 |   | Audited CRFs | =I16*0.1*I39 |
| 77 |   | Vendor Audits US | 0 |
| 78 |   | Vendor Audits ROW | 0 |
| 79 |   | Sub Contractors | 3 |
| 80 |   | IVRS Patients Diary | 0 |
| 81 |   | # Diary Calls Por Patient | 0 |
| 82 |   | Adm. Grants Paym. | 0 |

Figure 5-D

| | E | F |
|---|---|---|
| 12 | RFP Services Requested: | |
| 13 | Integrations | |
| 14 | Integrations | 0 |
| 15 | Reconciliations | 0 |
| 16 | Logistics | 0 |
| 17 | Portal | 0 |
| 18 | Project Accounting | 0 |
| 19 | Systems | |
| 20 | IVRS/ IWR | 0 |
| 21 | IVRS/ Diary | 0 |
| 22 | ESSDS Safety | 0 |
| 23 | Site Compliance tools | 0 |
| 24 | Screening Enrollment tools | 0 |
| 25 | Reporting and Document MGT | 0 |
| 26 | Monitoring System | 0 |
| 27 | Clinical Services | |
| 28 | Protocol and Study Documents | 0 |
| 29 | Project Management | 0 |
| 30 | Data Management | 0 |
| 31 | CRF Design | 0 |
| 32 | Database Design | 0 |
| 33 | Develop Data Management Plan | 0 |
| 34 | Setup Database | 0 |
| 35 | Develop Edit Check and Coding Programs | 0 |
| 36 | Data Entry/Cleaning | 0 |
| 37 | Run Database Cleaning | 0 |
| 38 | Database Audit | 0 |
| 39 | Start Up & Regulatory | 0 |

Figure 5-E

| D | E | F |
|---|---|---|
| 40 | Clinical Monitorig | 0 |
| 41 | Biostatistics & Medical Writing | 0 |
| 42 | Safety | 0 |
| 43 | TOTAL | =+F13+F19+F27 |
| 44 | | |
| 45 | Complexity Multipliers | |
| 46 | Start Up, Regulatory & Site Management | 1 |
| 47 | Monitoring | 1 |
| 48 | Project Management | 1 |
| 49 | Data Management | 1 |
| 50 | Safety, Medical & Scientific Services | 1 |
| 51 | Biostatistics & Medical Writing | 1 |
| 52 | Integrations | 1 |
| 53 | Reconciliations | 1 |
| 54 | Logistics | 1 |
| 55 | Portal | 1 |
| 56 | Project Accounting | 1 |
| 57 | IVRS/IWR | 1 |
| 58 | IVRS/Diary | 1 |
| 59 | ESSDS Safety | 1 |
| 60 | Site Compliance tools | 1 |
| 61 | Screening Enrollment tools | 1 |
| 62 | Reporting and Document Mgt | 1 |
| 63 | Monitoring System | 1 |
| 64 | | |
| 65 | | |
| 66 | Just in time Delivery | TRUE |
| 67 | Drug | 0 |
| 68 | Labs/pt | 0 |
| 69 | ECG/pt | 0 |
| 70 | Glucometers | 0 |
| 71 | Diary Device | 0 |
| 72 | Others | 0 |
| 73 | Total | =IF(F66=TRUE,SUM(F6 |
| 74 | | |
| 75 | | |
| 76 | | |
| 77 | | |
| 78 | | |

Figure 5-F

| | G | H | I |
|---|---|---|---|
| 1 | | | |
| 2 | | | |
| 3 | | | |
| 4 | | | |
| 5 | | | |
| 6 | | | |
| 7 | | | |
| 8 | | | |
| 9 | | | |
| 10 | | | |
| 11 | | | 0=No, 1=Yes |
| 12 | | Vendor Services: | Benchmark |
| 13 | | Data Management? | 1 |
| 14 | | Central Lab Downloads | =$C$27/4.33 |
| 15 | | Database Transfers | =1+$C$63 |
| 16 | | Total CRFs | =($C$18*$C$31)+($C$16*$C$ |
| 17 | | Electronic Transfers | =((I19+I15)*$C$52)*$C$27/4.3 |
| 18 | | Client Templates for CRFs | 0 |
| 19 | | E-Diary Transfers | 0 |
| 20 | | Study Start Up Required? | 1 |
| 21 | | Quarters | =$C$25/3 |
| 22 | | Central IRB sites | 1 |
| 23 | | Local IRB sites | 0 |
| 24 | | Regulatory Doc. Binders | =$C$13*I20 |
| 25 | | Study Manuals | =$C$13*2*I20 |
| 26 | | Study Team | =(3+I72)*I20 |
| 27 | | Safety Required? | 1 |
| 28 | | Expedited Reports | =$C$60*I27 |
| 29 | | Patient Narratives | =$C$60*I27 |
| 30 | | Monitoring Required? | 1 |
| 31 | | Interim Visits Freq. (Weeks) | 6 |
| 32 | | Initiation Teleconference | 0 |
| 33 | | Pharmacy Visits | =0*I30 |
| 34 | | Qualification Visits | =$C$13*I30 |
| 35 | | Initiation Visits | =$C$13*I30 |
| 36 | | Interim Visits--Paper CRFs | =$C$13*$C$27/I31*I30 |
| 37 | | Close-Out Visits | =$C$13*I30 |
| 38 | | Total Monitoring Visits | =I35+I34+I36+I37 |

Figure 5-G

| | G | H | I |
|---|---|---|---|
| 39 | | Audits Required? | 1 |
| 40 | | Site Audits | =$C$13*0.1*I30*I39 |
| 41 | | GCP Audits | =1*I30*I39 |
| 42 | | Study File Audit | =1*I39 |
| 43 | | Biostats Required? | 1 |
| 44 | | Number of Tables/Appendices | =20*I43 |
| 45 | | SAP | =1*I43 |
| 46 | | Unique Listings | =15*I43 |
| 47 | | Unique Summaries | =5*I43 |
| 48 | | Final Graphs | =5*I43 |
| 49 | | Subset Summaries | =0*I43 |
| 50 | | Subset Listings | =0*I43 |
| 51 | | Final Analysis | =1*I43 |
| 52 | | PM Required? | 1 |
| 53 | | Training Meeting | =$C$38*I52 |
| 54 | | Client Meetings | =$C$38*I52 |
| 55 | | Vendor to Manage | 1 |
| 56 | | Project Mngt Hours Week | =$C$13*0.6*I52 |
| 57 | | Study Material? | 1 |
| 58 | | SAE Form | 0 |
| 59 | | Informed Consent Form | 0 |
| 60 | | CRF Design | 0 |
| 61 | | Investigator Brochure | 0 |
| 62 | | CRF Review and Comm. | 0 |
| 63 | | Additional Study Material? | 1 |
| 64 | | Protocol Review and Comm. | 0 |
| 65 | | Document Translations | 0 |
| 66 | | Document Management | 0 |
| 67 | | Protocol Preparation | 0 |
| 68 | | DCMs | =1+I19 |
| 69 | | DCIs | 0 |
| 70 | | Lab Panels (Screens) | 0 |
| 71 | | | 0 |
| 72 | | Clinical Team | =($C$13/10)*I20 |
| 73 | | | 0 |
| 74 | | | |
| 75 | | | |
| 76 | | | |
| 77 | | | |

Normalization

Equalization

Figure 9-A

| | Protocol Number: XXXX |
|---|---|
| Indication | |
| Objectives | |
| Study Population | • Adult women with histologically- or cytologically-confirmed diagnosis of advanced XXXXX with measurable or nonmeasurable<br>• Baseline estradiol >30 pg/mL (Women on hormone replacement therapy are allowed)<br>• PS 2<br>• No prior chemotherapy for XXXXX<br>• Patients must have either:<br>   – Locally advanced recurrent disease following radiation or surgery,<br>   – Stage IIIB disease in patients who are not candidates for combined modality therapy, or<br>   – Stage IV disease<br>• Those patients with known brain metastases must have recovered from therapy for their CNS metastases and must have<br>• Adequate bone marrow, renal, hepatic, and cardiac function<br>• LDH must be < 3 X Upper Limit of Normal (ULN)<br>• Weight Loss must be <10% in previous 6 months<br>• Patients with LDH > ULN and weight loss ≥ 5% in previous 6 months will be excluded<br>• BMI must be <35 |
| Study Design | Multinational, phase III, open-label study of patients randomized to either:<br>Arm 1: XXXXX (conjugated paclitaxel dose of 175 mg/m2)<br>Arm 2: Gemcitabine (1000 mg/m2) or vinorelbine (30 mg/m2)<br>Randomization will be stratified to minimize potential imbalances between the 2 treatment arms. Stratification will be by age, geographic region, and stage of disease. |
| No. of Patients | Approximately 300 female patients will be randomized (150 in each arm). |
| Study Medications | Paclitaxel poliglumex (XXXXX) lyophilized powder with 90 mg paclitaxel as an ester conjugate of α-poly-(L)-glutamic acid per vial; supplied by XXXXXXXXXX.<br>Gemcitabine HCl for injection (NSC #613327), supplied as a lyophilized powder, is commercially available.<br>Vinorelbine tartrate (NSC #608210) for injection, supplied as a solution in Water for Injection, is commercially available. |
| Treatment Cycle | Based on the randomized treatment assignment, patients will receive either XXXXX or a comparator drug (vinorelbine tartrate or<br>Patients may not receive non-protocol-specified systemic antitumor therapy while receiving treatment on this study. |
| Safety Parameters | Toxicities will be evaluated at each patient visit using the NCI Common Toxicity Criteria, Version 3.<br>Hematology, coagulation, and clinical chemistry assessments will be assessed. |

Figure 9-B

| PROPOSED STUDY TARGET DATES | | |
|---|---|---|
| Study Start Date | Q1-Q2 2007 | |
| Site Initiation (study set up 4 months) | March 2007 for site selection start | |
| Enrollment Period: | March/April 2007-December 2008 (18-24 months) | |
| First Patient In | March/April 2007 (token USA pt) | |
| Last Patient In | March 2009 | |
| Treatment Period: | up to 6 cycles | |
| Last Patient Out | Sept 2009 | |
| Follow-up Period: | ~6 months | |
| Survival Follow up | SAA | |
| Interim Analysis | yes | |
| Last CRF in | TBD | |
| Clean Database Lock | Sept/Oct 2009 | |
| Statistical Analysis | TBD | |
| Clinical Study Report | Q4-2009 | |

Figure 9-C

| PROJECT OVERVIEW | |
|---|---|
| Compound Name | XXXXX |
| Program Phase | Phase III |
| Dosage Form | IV |
| Indication | XXXXX |
| Study Design | Randomized, Comparative |
| Patient Population | • Locally advanced or recurrent disease previously treated with radiation and/or surgery, or stage IIIB or IV |
| Number of Patients | 300 total |
| World Regions (US; EU; ** May need to greatly increase number of sites in these countries. These are the only countries we will consider) | Spain, France, Belgium, Germany, USA, Canada, Australia, Czech, UK, |
| Number of Investigators | 150-180 |
| Approximate Number of Patients Per Site | 1-2 subjects/site |
| Enrolment Rate | .5-1 patient per site every month |
| Duration of Patient Participation | upto 6 cycles plus follow up period ~1 year |
| -Screening/Run-In | <28 days |
| - # of cycles | 6 |
| -Follow-Up | 6 months |
| -Survival Follow-Up | SAA |
| Number of Protocol Summary Translations | French, Italian, Spanish, German, Danish, 3-5 Eastern Europe Translations, Mexico. |
| Number of Full Protocol Translations | SAA |
| Number of Informed Consent Translations | SAA |
| Number of Investigators' Meetings | 1 per region |
| Number of Protocol Amendments | 2 |

Figure 9-D

| Clincal Information | | |
|---|---|---|
| | Total Number of Monitoring Visits | Monitoring frequency every 6-8 weeks. |
| | -Potential sites Identified | |
| | -Pre-Study Evaluation (<1.2 X # ctrs) | 40 |
| | -Initiation (1 X # ctrs) | 150 |
| | -Interim Monitoring (IM) | every 6-8 weeks |
| | - IM Freq (enrollment) | within 3 weeks of FPI or sooner |
| | - IM Freq (treatment) | every 6-8 weeks |
| | - IM Freq (followup) | 2-3 months |
| | Number of Co-Monitoring Visits | 20 |
| | -Close-Out | 150 |
| | Total Number of Monitoring & close out Visits | |
| | Duration of Monitoring Visits (Hours) | 6 hours |
| | -Initiation | 24 (including travel/prep time) |
| | -Interim | 24 (including travel/prep time) |
| | -Close-Out | 24 (including travel/prep time) |
| Project Management | | |
| | Number of COMPANY/CRO Project Team Meetings | Quarterly meetings |
| | Number of internal face-to-face CRO Project Team Meetings (1 kick-off meeting) | 6 |
| | COMPANY/CRO Project Team Teleconferences | Weekly |
| | Internal CRO project team teleconferences | TBD |

Figure 9-E

| Central Lab / Readers/ Special Assessments | | |
|---|---|---|
| | Central lab (Estrogen, LDH) | All labs |
| | Local Labs: | Chem/cbc |
| Data Management | | |
| | # of Unique CRF Pages | 33 |
| | # of CRF Pages/ Completed Patient | 209 |
| | # of CRF Pages/ Screen Failure Patients | None |
| | Will Screen Fail CRF's Be Processed (yes/no) | None |
| | # of CRF Pages/ Early Withdrawal | 23+(16xC), C=# of cycles |
| | Total # of CRFs to be Processed by Data Management | |
| | # of Queries/ Patient | 20 |
| | # of Manually Coded Items/ Patient | None |
| | # of Other Electronic Data Sources | One, central lab |
| | Data Transfers: | |
| | # of Cumulative Dirty DB Transfers | Twelve |
| | # of Cumulative Clean DB Transfers | Six |
| | # of Incrementally Clean DB Transfers | None |
| | Interim Analysis | |
| | # of Interim Analyses | 1 |
| | # of Interim Analyses to Support Planned Interim Analyses | 1 |
| | Will there be an SAE Reconciliation to the Clinical Database (yes/no) | yes |
| | DSMC (yes/no) | no |
| | # of Times DSMC will Meet | |
| | Annual IND Filing (yes/no) | yes |

Figure 9-F-1

| 16.1 Schedule of Activities | Baseline | During Treatment[a] | EOT[d] | F/U |
|---|---|---|---|---|
| Informed Consent | X | | | |
| Inclusion/Exclusion Criteria | X | | | |
| Medical/Surgical History including comorbidities, HRT status, menopausal status | ≤2 weeks pre randomization | | | |
| Estradiol, LDH (central lab)[b] | ≤2 weeks pre randomization | | | |
| Pregnancy test, women of reproductive potential | ≤2 weeks pre randomization | | | |
| Coagulation parameters (PT, aPTT, INR) | ≤2 weeks pre trt | ≤72 hrs before study drug administration in patients with abnormal parameters at baseline or patients on therapeutic anticoagulation therapy | | |
| Clinical Chemistry: sodium, potassium, chloride, bicarbonate, BUN, creatinine, SGOT, SGPT, calcium, phosphate, uric acid, and total bilirubin | ≤2 weeks pre randomization | ≤7 days before study drug administration of cycles 2, 4, 6[c] | X | |
| Hematology: CBC with differential, platelet count | ≤2 weeks pre randomization | ≤72 hr before each study drug administration and on day 10 (±3)[c] | X | |
| Cytokines, cathepsin B (central lab) | ≤2 weeks pre randomization | day 10 cycle 1 only (±3 days) | | |
| Vital Signs (heart rate, blood pressure, respiration rate) | ≤2 weeks pre tx | Within 1 hr before & after each study drug administration | X | |
| Temperature | ≤2 weeks pre tx | Within 1 hr before each administration | | |
| ECOG Performance Status | ≤2 weeks pre randomization | ≤72 hrs before each study drug administration | X | |
| CT Scan or MRI of chest and abdomen | ≤4 weeks pre randomization | Last week of every 3rd cycle and repeated at least 4 wks after PR or CR. Additional assessments as clinically indicated | Every 8 weeks (±2 weeks) after last CT until progression, non-study treatment, or death | |
| ECG | ≤2 weeks pre randomization | | | |
| Chest X-ray | ≤4 weeks pre randomization | day 10 cycle 1 only (±3 days) | | |
| Concomitant Medications | ≤2 weeks pre randomization | Before each study drug administration | X | |
| Physical exam (weight and at baseline only, height) | ≤2 weeks pre randomization | Symptom directed exam ≤2 days before 1st administration each cycle | X | |

Figure 9-F-2

| | ≤2 weeks pre randomization | | |
|---|---|---|---|
| Pain Assessment | | ≤72 hrs before each study drug administration | X |
| FACT-LCS (only in countries in which a validated translation is currently available from FACIT) | ≤72 hr pre tx | ≤72 hrs before each study drug administration | X |
| Toxicity Assessment Record hospitalizations | | At each patient contact until 30 days after last study treatment (unless a study drug related AE continues–in which case, they must be followed until the earliest of resolution, initiation of | |
| Clinical Assessment for disease progression | | ≤2 days before each study drug administration | |
| Drug Administration CT-2103 Gemcitabine Vinorelbine | | Day 1 (±2) each 21-day cycle Day 1, 8, 15 each 28-day cycle Day 1, 8, 15 each 21-day cycle | |
| Survival/disease status/subsequent treatment | | | Every 4 weeks (±1) after EOT visit until death |

[a] Cycles are repeated for up to 6 cycles, or until intolerable toxicity, disease progression, or patient withdraws consent.
[b] Results must be available before randomization
[c] Results to be assessed by physician before administering next treatment
[d] End of Treatment visit: 30-37 days after last treatment or before initiation of non protocol chemotherapy. Regardless, all toxicities must be assessed between days 30 -

Figure 9-G

| DESCRIPTION | RESPONSIBILITIES ||||  ESTIMATED DIRECT COSTS |||| ESTIMATED PASSTHROUGH COSTS |||| COMMENTS |
|---|---|---|---|---|---|---|---|---|---|---|---|---|---|
| | Sponsor | VENDER | Joint | n/a | ITEM TOTAL ||| SECTION SUB TOTAL | ITEM TOTAL ||| SECTION SUB TOTAL | |
| | | | | | Unit | Price per Unit | Item Total | | Unit | Price per Unit | Item Total | | |
| 1 Project Management | 0 | 0 | X | 0 | 0 | 0 | 0 | 0 | 0 | 0 | 0 | 0 | 0 |
| 2 Medical Management | X | 0 | 0 | 0 | 0 | 0 | 0 | 0 | 0 | 0 | 0 | 0 | 0 |
| 3 Vendor Administration | 0 | 0 | X | 0 | 0 | 0 | 0 | 0 | 0 | 0 | 0 | 0 | 0 |
| 4 Study Start Up | 0 | 0 | X | 0 | 0 | 0 | 0 | 0 | 0 | 0 | 0 | 0 | 0 |
| 5 Initiation and Monitoring | 0 | X | 0 | 0 | 0 | 0 | 0 | 0 | 0 | 0 | 0 | 0 | 0 |
| 6 Data Management | 0 | X | 0 | 0 | 0 | 0 | 0 | 0 | 0 | 0 | 0 | 0 | 0 |
| 7 Statistical Analysis | X | 0 | 0 | 0 | 0 | 0 | 0 | 0 | 0 | 0 | 0 | 0 | 0 |
| 8 Drug Supply Management | X | X | X | 0 | 0 | 0 | 0 | 0 | 0 | 0 | 0 | 0 | 0 |
| 9 Labs and Assessments | 0 | 0 | X | X | 0 | 0 | 0 | 0 | 0 | 0 | 0 | 0 | 0 |

Total     Direct Cost  0     Passthrough  0

Figure 9-H

| DESCRIPTION | RESPONSIBILITIES | | | | ESTIMATED DIRECT COSTS | | | | | | ESTIMATED PASS-THROUGH COSTS | | | | | COMMENTS |
|---|---|---|---|---|---|---|---|---|---|---|---|---|---|---|---|---|
| | Sponsor | VENDER | Joint | n/a | Unit Type | # Units | Price per Unit | Item Total | SECTION SUB TOTAL | | Unit Type | # Units | Price per Unit | Item Total | SECTION SUB TOTAL | |
| | | | | | | | | ITEM TOTAL | | | | | ITEM TOTAL | | | |
| 1 Project Management | X | X | X | | | | | | | | | | | | | |
| 1.1 Time Line Management | X | X | X | | | | | | | | | | | | | |
| 1.2 Team Management | X | X | X | | | | | | | | | | | | | |
| 1.2.1 Status Reports | X | X | | | | | | | | | | | | | | |
| 1.2.1.1 Essential Doc. Version Tracking (approved. Prot. ICF, CRF, IB) | | X | | | | | | | | | | | | | | |
| 1.2.1.2 Initiation (Ess. Doc tracking by country and site) | | X | | | | | | | | | | | | | | |
| 1.2.1.3 Pt Recruitment | | X | | | | | | | | | | | | | | |
| 1.2.1.4 Monitoring (Visits and reports) | X | X | | | | | | | | | | | | | | |
| 1.2.1.5 CRF retrieval | | X | | | | | | | | | | | | | | |
| 1.2.1.6 Queries (rate; closed; pending) | | X | | | | | | | | | | | | | | |
| Direct Cost | | X | | | | | | | | | | | | | | |
| 1.2.1.8 SAE | | X | | | | | | | | | | | | | | |
| 1.2.1.9 Invest Grant payment | | | X | | | | | | | | | | | | | |
| 1.2.1.10 Vender payments | | | X | | | | | | | | | | | | | |
| 1.2.1.11 other | | X | | | | | | | | | | | | | | |
| 1.2.2 Task List (Wkly Updates) | | X | | | | | | | | | | | | | | |
| 1.2.3 Issues/Decision Log (Wkly Updates) | | X | | | | | | | | | | | | | | |
| 1.2.4 CTI/ CRO Meeting Telecon. Agenda; Minutes (wkly) | | X | | | | | | | | | | | | | | |
| 1.2.5 Weekly Monitoring Team Meetings | | X | | | | | | | | | | | | | | |
| 1.2.6 Frequently Asked Questions for sites (Wkly) | | X | | | | | | | | | | | | | | |
| 1.2.7 Study News Letter-(Mo/Qtr) (CRF completion updates; Protocol Clarifications; Freq Asked Questions; AE coding help) | | X | | | | | | | | | | | | | | |
| 1.3 Training | X | X | | | | | | | | | | | | | | |
| 1.3.1 Project Familization | X | X | | | | | | | | | | | | | | |
| 1.3.2 CRO Kick Off Mtg | X | X | | | | | | | | | | | | | | |
| 1.3.3 CTI/CRO Face to Face | X | X | | | | | | | | | | | | | | |

Figure 9-I

| Task | |
|---|---|
| 1.4 Recruitment Plan | X |
| 2 Medical Management | X |
| 2.1 Medical Monitoring/ PV | X |
| 2.1.1 Medical Monitor | X |
| 2.1.2 SAE Initial &Follow-up Reports | X |
| 2.1.3 SAE Narrative as part of SAE Rpt | X |
| 2.1.4 24 hr Med non SAE coverage | X |
| 2.1.5 Reportable Determination | X |
| 2.1.6 CRF or Table/Listing Safety | X |
| 2.1.7 Generation of IND / CIOMOS safety letter | X |
| 2.1.8 Site Safety Report Submission | X |
| 2.1.9 Develop and maintain safety database | X |
| 2.1.10 Reconcile safety database with AE data base | X |
| 2.1.11 Distribute SAE and safety updates per GCP to sites | X |
| 2.1.12 DMC management/safety updates | X |
| 2.2 Quality Plan | X |
| 2.2.1 Vendor Audits | X |
| 2.2.2 Site Audits | X |
| 2.3 Records Archiving & Management | X |
| 3 Vendor Administration | X |
| 3.1 Drug packaging facility payment | X |
| 3.2 Central laboratory payments | X |
| 3.3 Assessment Payments | X |
| 3.4 Central Reader Payment | X |

Figure 9-J

| DESCRIPTION | RESPONSIBILITIES | | | | ESTIMATED DIRECT COSTS | | | | | ESTIMATED PASSTHROUGH COSTS | | | | | COMMENTS |
|---|---|---|---|---|---|---|---|---|---|---|---|---|---|---|---|
| | Sponsor | VENDER | Joint | n/a | Unit Type | ITEM TOTAL | | | SECTION SUB TOTAL | Unit Type | ITEM TOTAL | | | SECTION SUB TOTAL | |
| | | | | | | Unit | Price per Unit | Item Total | | | Unit | Price per Unit | Item Total | | |
| 4 Study Start Up | X | X | X | X | | | | | | | | | | | |
| 4.1 Investigator Brochure/ Pharmacy Brochure | | X | | | | | | | | | | | | | |
| 4.1.1 Draft or update IB | X | | | | | | | | | | | | | | |
| 4.1.2 Review and Approve | X | | | | | | | | | | | | | | |
| 4.1.3 Distribute to Sites; IRB/IEC | | X | | | | | | | | | | | | | |
| 4.2 Protocol development | X | X | | | | | | | | | | | | | |
| 4.2.1 Literature review, background research | X | | | | | | | | | | | | | | |
| 4.2.2 Design and write protocol | X | | | | | | | | | | | | | | |
| 4.2.3 Review Protocol | X | | | | | | | | | | | | | | |
| 4.2.4 Approve protocol | X | | | | | | | | | | | | | | |
| Direct Cost | | X | | | | | | | | | | | | | |
| 4.2.6 Translate Protocol | | X | | | | | | | | | | | | | All study documents translated must have certified back translations. |
| 4.2.7 Copy & Distribute Protocol to sites | | X | | | | | | | | | | | | | |
| 4.2.8 Protocol Amendments | X | | | | | | | | | | | | | | |
| 4.3 Informed Consent Development | X | X | X | | | | | | | | | | | | |
| 4.3.1 Draft Informed Consent Template | X | | | | | | | | | | | | | | |
| 4.3.2 IC Template review and approval | | X | | | | | | | | | | | | | |
| 4.3.3 IC Translation | | X | | | | | | | | | | | | | |
| 4.4 CRF (see also DM) | X | | X | | | | | | | | | | | | |
| 4.4.1 Approve CRFs and patient assessment booklets | X | | | | | | | | | | | | | | |
| 4.4.2 CRF completion conventions | | X | | | | | | | | | | | | | |
| 4.5 Regulatory Submissions | | X | | | | | | | | | | | | | |
| 4.5.1 Manage regulatory submissions (based on FDA IND docs) | | X | | | | | | | | | | | | | |
| 4.5.2 Manage regulatory updates | | X | | | | | | | | | | | | | |
| 4.6 Investigator recruitment and Selection | X | ##### | X | | | | | | | | | | | | |
| 4.6.1 Develop list of potential investigators | | | X | | | | | | | | | | | | |
| 4.6.2 Qualification Telephone surveys | | X | | | | | | | | | | | | | |
| 4.6.3 Pre-study Qualification Visits | | X | | | | | | | | | | | | | |
| 4.6.3.1 Conduct site qualification visits | | X | | | | | | | | | | | | | |

Figure 9-K

| Task | C1 | C2 | C3 | C4 | C5 | C6 | C7 | C8 | C9 | C10 | C11 |
|---|---|---|---|---|---|---|---|---|---|---|---|
| 4.6.3.2 Provide written site evaluation report | | X | | | | | | | | | |
| 4.6.4 Select sites | | X | | | | | | | | | |
| 4.6.5 Prepare Investigator contract | X | | | | | | | | | | |
| 4.6.6 Negotiate Investigator grants (site budgets) | X | | | | | | | | | | |
| 4.6.7 Collect essential and reg documents | | X | | | | | | | | | |
| 4.8 Drug Supply | X | | | | | | | | | | |
| 4.8.1 Arrange drug packaging | X | | | | | | | | | | |
| 4.8.2 Arrange drug labeling | X | | | | | | | | | | |
| 4.8.3 Drug storage and distribution | X | | | | | | | | | | |
| 4.9 Patient randomization (IVRS?) ( See Biostats) | | X | | | | | | | | | |
| 4.1 IRB/IEC | | X | | | | | | | | | |
| 4.10.1 Select Central IRB | | X | | | | | | | | | |
| 4.10.2 Manage Ethics Committee/IRBs submissinos | | X | | | | | | | | | |
| 4.10.3 Managage Regulatory Submissions | | X | | | | | | | | | |
| 4.11 Pk Assessments | | X | | | | | | | | | |
| 4.11.1 Identify Labs, NDA, RFP | X | | | | | | | | | | |
| 4.11.2 Vendor Audits | X | | | | | | | | | | |
| 4.11.3 Develop/Transfer procedures | X | | | | | | | | | | |
| 4.11.4 Per patient cost of Sample kits | X | | | | | | | | | | |
| 4.11.5 Shipping, testing, and storage procedures | X | | | | | | | | | | |
| 4.11.6 Sample archiving | X | | | | | | | | | | |
| 4.11.7 Electronic Data Collection | | X | | | | | | | | | |
| 4.11.8 Data Transfer | | X | | | | | | | | | |
| 4.12 Central laboratory | | X | | | | | | | | | |
| 4.12.1 Identify Labs, NDA, RFP | | X | | | | | | | | | |
| 4.12.2 Vendor Audits | | | | | | | | | | | |
| 4.12.3 Per patient cost of Sample kits | | X | | | | | | | | | |
| 4.12.4 Per patient cost of lab tests | | X | | | | | | | | | |
| 4.12.5 Sample archiving | | X | | | | | | | | | |
| 4.12.6 Electronic Data Collection | | X | | | | | | | | | |
| 4.12.7 Data Transfer | | X | | | | | | | | | |
| 4.13 Site Study Binders | | X | | | | | | | | | |
| 4.13.1 Site Regulatory Binder | | X | | | | | | | | | |
| 4.13.2 Site Study Binder | | X | | | | | | | | | |
| 4.13.3 Site Pharmacy Binder | | X | | | | | | | | | |
| 4.13.4 Site pK Binder | | | | | | | | | | | |
| 4.14 Set Up CTMF | X | | | | | | | | | | |

Figure 9-L

| DESCRIPTION | RESPONSIBILITIES | | | | ESTIMATED DIRECT COSTS | | | | | ESTIMATED PASSTHROUGH COSTS | | | | COMMENTS |
| --- | --- | --- | --- | --- | --- | --- | --- | --- | --- | --- | --- | --- | --- | --- |
| | Sponsor | VENDER | Joint | n/a | Unit Type | ITEM TOTAL | | | SECTION SUB TOTAL | Unit Type | ITEM TOTAL | | SECTION SUB TOTAL | |
| | | | | | | Unit | Price per Unit | Item Total | | | Unit | Price per Unit | Item Total | | |
| 5 Initiation and Monitoring | x | x | | | | | | | | | | | | |
| 5.1 Initiation | | x | | | | | | | | | | | | |
| 5.1.1 Prestudy Documentation | | x | | | | | | | | | | | | |
| 5.1.3 Complete initiation visit report | | x | | | | | | | | | | | | |
| 5.2 Interim Monitoring | | x | | | | | | | | | | | | |
| 5.2.1 Conduct monitoring visits | | x | | | | | | | | | | | | |
| 5.2.2 Verify 100% of source documentation | | x | | | | | | | | | | | | |
| 5.2.3 Resolve edits/queries with site | | x | | | | | | | | | | | | |
| 5.2.4 Review drug records | | x | | | | | | | | | | | | |
| 5.2.5 Review lab storage Direct Cost | | x | | | | | | | | | | | | |
| 5.2.7 Interim Monitoring Visit report | | x | | | | | | | | | | | | |
| 5.2.8 Complete interim monitoring report | | x | | | | | | | | | | | | |
| 5.3 Site Close-Out | x | x | | | | | | | | | | | | |
| 5.3.1 Conduct site close-out visits | | x | | | | | | | | | | | | |
| 5.3.2 Site files complete, records archive | x | | | | | | | | | | | | | |
| 5.3.3 data queries resolved | | x | | | | | | | | | | | | |
| 5.3.4 sample archival discussed | | x | | | | | | | | | | | | |
| 5.3.5 drug reconciled | | x | | | | | | | | | | | | |
| 5.3.6 Survival | | x | | | | | | | | | | | | |
| 5.3.7 Provide close-out trip report | | x | | | | | | | | | | | | |
| 5.4 Site General Administration | | x | | | | | | | | | | | | |
| 5.4.1 Weekly telephone contact with sites | | x | | | | | | | | | | | | |
| 5.4.2 Brief In-person site contact | | x | | | | | | | | | | | | |
| 5.4.3 Investigator /institution grant administration | | x | | | | | | | | | | | | |
| 5.4.4 Provide newsletters | | x | | | | | | | | | | | | |
| 5.4.5 Provide helpdesk for study conduct (unrelated to eCRF) | | x | | | | | | | | | | | | |

Figure 9-M

| DESCRIPTION | RESPONSIBILTIES ||||  ESTIMATED DIRECT COSTS |||||  ESTIMATED PASSTHROUGH COSTS ||||| COMMENTS |
|---|---|---|---|---|---|---|---|---|---|---|---|---|---|---|---|
| | | | | | | ITEM TOTAL |||| | ITEM TOTAL |||| |
| | Sponsor | VENDER | Joint | n/a | Unit Type | Unit | Price per Unit | Item Total | SECTION SUB TOTAL | Unit Type | Unit | Price per Unit | Item Total | SECTION SUB TOTAL | |
| 6 Data Management | X | X | X | | | | | | | | | | | | |
| 6.1 Data Project Management | | | | | | | | | | | | | | | |
| 6.2 Develop Data Management and Quality Plan | | X | | | | | | | | | | | | | |
| 6.2.1 Collaborate, review, and approve DM and DQ Plan | X | | | | | | | | | | | | | | |
| 6.3 Status Reports CRFs; Data Entry; Queries | | X | | | | | | | | | | | | | |
| 6.4 Client Conference Calls | | | X | | | | | | | | | | | | |
| 6.5 CRFs | | | X | | | | | | | | | | | | |
| CRFs/Paper or Electronic | | | | | | | | | | | | | | | |
| 6.5.1.1 Provide Draft CRFs | | | | | | | | | | | | | | | |
| 6.5.1.2 Design CRFs | | | | | | | | | | | | | | | |
| Direct Cost | | | | | | | | | | | | | | | |
| 6.5.1.4 Approve CRFs | | | | | | | | | | | | | | | |
| 6.5.2 Print CRFs | | | | | | | | | | | | | | | |
| 6.5.3 Distribute CRFs to sites | | | | | | | | | | | | | | | |
| 6.5.4 Electronic CRF | | X | | | | | | | | | | | | | |
| 6.5.4.1 Server/Datase Configeration & Qualification | | X | | | | | | | | | | | | | |
| 6.5.4.2 eCRF Design | | X | | | | | | | | | | | | | |
| 6.5.4.3 eCRF Programming | | X | | | | | | | | | | | | | |
| 6.5.4.4 eCRF QC | | X | | | | | | | | | | | | | |
| 6.5.4.5 eCFR Approval | X | | | | | | | | | | | | | | |
| 6.5.4.6 eCRF Deployment | | X | | | | | | | | | | | | | |
| 6.5.4.7 eCRF Completion conventions | | | X | | | | | | | | | | | | |
| 6.6 Data Base Administration | X | X | X | | | | | | | | | | | | |
| 6.6.1 Data Base Specification | | X | | | | | | | | | | | | | |
| 6.6.2 Data Base Design | | X | | | | | | | | | | | | | |
| 6.6.3 Approve DB Design | X | | | | | | | | | | | | | | |
| 6.6.4 Data Base QC | | | X | | | | | | | | | | | | |
| 6.6.5 Data Base Audit | | | X | | | | | | | | | | | | |
| 6.6.6 Data Base Documentation | | X | | | | | | | | | | | | | |
| 6.7 Edit Checks | | X | X | | | | | | | | | | | | |
| 6.7.1 Edit Check Specifications | | X | | | | | | | | | | | | | |
| 6.7.2 Edit Check Programing | | X | | | | | | | | | | | | | |
| 6.7.3 Edit Check QC | | | X | | | | | | | | | | | | |
| 6.8 Self-Evident Edit Checks | X | | | | | | | | | | | | | | |
| 6.9 Data Entry | | X | | | | | | | | | | | | | |
| 6.9.1 eCRF at Site | | X | | | | | | | | | | | | | |
| 6.9.2 paper - Double Data entry | | | | | | | | | | | | | | | |
| 6.1 Dictionary Coding | | | X | | | | | | | | | | | | |
| 6.10.1 SAE Coding | | | X | | | | | | | | | | | | |
| 6.10.2 Mediation Coding | | | X | | | | | | | | | | | | |
| 6.11 CRF storage or imaging | | | | | | | | | | | | | | | open for bids |
| 6.12 Central Laboratory Data intergration | | X | | | | | | | | | | | | | |
| 6.12.1 Lab Normal Ranges | | X | | | | | | | | | | | | | |
| 6.13 Central Scan or X-ray data | | X | | | | | | | | | | | | | |

Figure 9-N

| DESCRIPTION | RESPONSIBILITIES | | | | Unit Type | ESTIMATED DIRECT COSTS | | | | ESTIMATED PASSTHROUGH COSTS | | | | COMMENTS |
| --- | --- | --- | --- | --- | --- | --- | --- | --- | --- | --- | --- | --- | --- | --- |
| | Sponsor | VENDER | Joint | n/a | | ITEM TOTAL | | | SECTION SUB TOTAL | Unit Type | ITEM TOTAL | | SECTION SUB TOTAL | |
| | | | | | | Unit | Price per Unit | Item Total | | | Unit | Price per Unit | Item Total | | |
| 7 Statistical Analysis | X | | | | | | | | | | | | | |
| 7.1 Statistical Analysis Plan | X | | | | | | | | | | | | | |
| 7.1.1 Develop Analysis Plan | X | | | | | | | | | | | | | |
| 7.1.2 Review and Approve SAP | X | | | | | | | | | | | | | |
| 7.1.3 Number of tables (unique/total) | X | | | | | | | | | | | | | |
| 7.1.4 Number of Listings (unique/total) | X | | | | | | | | | | | | | |
| 7.1.5 Number of figures (unique/total) | X | | | | | | | | | | | | | |
| 7.2 Randomization Plan (IVRS?) | X | | | | | | | | | | | | | |
| 7.3 Data Monitoring Committee | X | | | | | | | | | | | | | |
| 7.4 Table, Listing, and figure Programing | X | | | | | | | | | | | | | |
| Direct Cost | X | | | | | | | | | | | | | |
| 7.7 Query Generation | X | | | | | | | | | | | | | |
| 7.7 Interm Analysis | X | | | | | | | | | | | | | |
| 7.8 Draft T/L/F | X | | | | | | | | | | | | | |
| 7.9 Blinded/ Mock T/L/F | X | | | | | | | | | | | | | |

Figure 9-O

| DESCRIPTION | RESPONSIBILITIES | | | | ESTIMATED DIRECT COSTS | | | | ESTIMATED PASSTHROUGH COSTS | | | | COMMENTS |
|---|---|---|---|---|---|---|---|---|---|---|---|---|---|
| | Sponsor | Vendor | Joint | n/a | Unit Type | ITEM TOTAL | | SECTION SUB TOTAL | Unit Type | ITEM TOTAL | | SECTION SUB TOTAL | |
| | | | | | | Unit | Price per Unit | Item Total | | | Unit | Price per Unit | Item Total | | |
| 8 Drug Supply Management | X | X | X | | | | | | | | | | | |
| 8.1 Drug Supply Plan | X | X | X | | | | | | | | | | | |
| 8.1.1 Drug Supply | X | X | | | | | | | | | | | | |
| 8.1.2 Packaging | X | X | | | | | | | | | | | | |
| 8.1.3 Inventory Management | X | | | | | | | | | | | | | |
| 8.1.4 Randomization? | X | | | | | | | | | | | | | |
| 8.1.5 PI level lot tracking | X | | | | | | | | | | | | | |
| 8.1.6 Distributor management | X | | | | | | | | | | | | | |
| 8.1.7 Country Specific Labels | X | | | | | | | | | | | | | |
| 8.1.8 Import licenses | | X | | | | | | | | | | | | The Importer of Record is the one that applies for the Import License and that is usually the CRO, except in France which CTI French depot can secure |
| Direct Cost | X | | | | | | | | | | | | | |
| 8.1.10 Country Depots | X | | | | | | | | | | | | | |
| 8.1.8 Within Country Comparator Procurement | X | | | | | | | | | | | | | |
| 8.1.12 Shipping requirements (Hazardous?) | X | X | | | | | | | | | | | | |
| 8.1.13 Shipper | X | X | | | | | | | | | | | | |
| 8.1.14 Drug Distruction | | | X | | | | | | | | | | | Certain sites can be permitted to destroy at the clinical site but requires XXX approval. CRO needs to do site level drug reconciliation. SCM handles product level reconciliation. |
| 8.1.15 Final Reconciliation | | | X | | | | | | | | | | | |
| 8.1.16 Ancillary Supplies | X | | | | | | | | | | | | | |
| 8.2 Supply Study Drug for packaging | X | X | | | | | | | | | | | | |
| 8.2.1 Identify vendors for compators | X | | | | | | | | | | | | | |
| 8.2.2 Import Licenses and Customs Clearance | | X | | | | | | | | | | | | Except for France |
| 8.3 Package Study Drug | X | | | | | | | | | | | | | |
| 8.4 Produce Randomization Code | X | | | | | | | | | | | | | |
| 8.5 Label study drug | X | | | | | | | | | | | | | |
| 8.6 Ship study drug to site | | | X | | | | | | | | | | | |
| 8.7 Store study drug | | | X | | | | | | | | | | | |
| 8.8 study drug accountability | | | X | | | | | | | | | | | See comments on 8.1.15 |
| 8.9 Perform post-study drug accountability | | | X | | | | | | | | | | | See comments on 8.1.15 |
| 12 Study drug disposition & accountability | | | X | | | | | | | | | | | All disposition managed by SC but the ones disposed at clinical sites will require the CRO to ensure a Certificate of Destruction is included in the site file as proof of destruction. |

Figure 9-P

| DESCRIPTION | RESPONSIBILITIES | | | | ESTIMATED DIRECT COSTS | | | | | ESTIMATED PASSTHROUGH COSTS | | | | | COMMENTS |
|---|---|---|---|---|---|---|---|---|---|---|---|---|---|---|---|
| | Sponsor | Vendor | Joint | n/a | Unit Type | ITEM TOTAL | | | SECTION SUB TOTAL | Unit Type | ITEM TOTAL | | | SECTION SUB TOTAL | |
| | | | | | | Unit | Price per Unit | Item Total | | | Unit | Price per Unit | Item Total | | |
| 9 Labs and Assessments | | | | | | | | | | | | | | | |
| 9.1 Central lab | | | X | X | | | | | | | | | | | |
| 9.1.1 per patient sampling kit cost | | | X | | | | | | | | | | | | |
| 9.1.2 per patient testing cost | | | X | | | | | | | | | | | | |
| 9.1.3 per patient shiping est. | | | X | | | | | | | | | | | | |
| 9.1 pK Lab | | | | X | | | | | | | | | | | |
| 9.1.1 Test Validation Charges | | | | | | | | | | | | | | | |
| 9.1.2 per patient sampling kit cost | | | | | | | | | | | | | | | |
| 9.1.3 per patient testing cost | | | | | | | | | | | | | | | |
| 9.1.4 per patient shiping est. | | | | | | | | | | | | | | | |
| Direct Cost | | | | | | | | | | | | | | | |
| 9.2 Central Readers | | | | | | | | | | | | | | | |

Figure 10-A

XXXXXX
1.3 BUDGET SUMMARY

The budget proposal has been prepared according to the study specifications provided by XXXX XXXXXXXX, as detailed in the key assumptions in Section 1.4, the timelines described in Section 1.5, and the observations made in Section 1.2 above.

A summary of the current proposed budget is shown below along with an explanation of various study-specific considerations and any relevant modifications in the budget. The detailed considerations are provided in the attached excel file using XXXXXXXXXX' provided format.

| CLINICAL TRIAL MANAGEMENT SERVICES (excluding Pass-Through Costs) | $ 4,863,116 USD |
|---|---|

TERMS

- All prices are excluding VAT.
- All expenses will be invoiced separately, on presentation of justification, with a 2% service fee applied.
- The estimate excludes investigators grants; extra hospital costs; writing and submission of any amendments; organization and presentation of results to investigators, organization and payment of fees for extramural investigator meetings; drug shipment.
- Estimate is based on an exchange rate of 1 euro = 1.3 US$. If an exchange rate fluctuation by greater than +/- 5% occurs, contract prices will be adjusted accordingly.

PAYMENT SCHEDULE

To be discussed between XXXX and XXXXX.

Figure 10-B

CONFIDENTIAL 1.4     KEY ASSUMPTIONS

| PARAMETER | ASSUMPTIONS |
|---|---|
| Investigational Product | XXXXXX |
| Other Study Drugs | XXXXXXXXXX, XXXXXXXXXX |
| Indication | XXXXXXXX |
| Study Phase | Phase III |
| Study Design | Multinational, open-label, randomized, 2-arm study with stratification by age, geographic region and disease stage |
| No. Treatment Arms | 2 |
| No. Patients | 300 (150 per arm) |
| No. Investigative Countries | 9 (Spain, France, Belgium, Germany, USA, Canada, Australia, Czech, UK) |
| No. Investigative Sites | 150 (North America: 60, ROW: 90) |
| Study Duration | 35 months |
| No. Monitoring Visits | 2 visits/site |
| Total No. Serious Adverse Event | TBD |
| Estimated No. Total CRF Pages / Patient | 209 |
| Estimated No. Unique CRF Pages / Patient | 33 |
| Estimated No. Total CRF Pages | 62,700 |

1.5     PROPOSED STUDY TIMELINES

| TIMELINE | |
|---|---|
| Set up (Contract Award, Kick-off & Investigator Meetings, Training, First Site Initiation) | 4 months |
| Enrollment Duration (first patient in to last patient in) | 24 months |
| Follow-up Duration | 6 months |
| Study Close-Out Activities (Last Patient / Final Database Clean) | 1 month |
| Total Project Duration | 35 months |

XXXXX      X/XX      Version 1 26-Jan-07

Figure 11-A

| PROPOSED STUDY TARGET DATES | |
|---|---|
| Study Start Date | Q1-Q2 2007 |
| Site Initiation (study set up 4 months) | March 2007 for site selection start |
| Enrollment Period: | March/April 2007-December 2008 (18-24 months) |
| | |
| First Patient In | March/April 2007 (token USA pt) |
| Last Patient In | March 2009 |
| Treatment Period: | up to 6 cycles |
| Last Patient Out | Sept 2009 |
| Follow-up Period: | ~6 months |
| Survival Follow up | SAA |
| Interim Analysis | yes |
| Last CRF in | TBD |
| Clean Database Lock | Sept/Oct 2009 |
| Statistical Analysis | TBD |
| Clinical Study Report | Q4-2009 |
| | |
| | |

Figure 11-B

| PROJECT OVERVIEW | | |
|---|---|---|
| | Compound Name | Xyotax |
| | Program Phase | Phase III |
| | Dosage Form | IV |
| | Indication | NSCLC, E+ female only |
| | Study Design | Randomized, Comparative |
| | Patient Population | • Locally advanced or recurrent disease previously treated with radiation and/or surgery, or stage IIIB or IV |
| | Number of Patients | 300 total |
| | World Regions (US; EU; ** May need to greatly increase number of sites in these countries. These are the only countries we will consider) | Spain, France, Belgium, Germany, USA, Canada, Australia, Czech, UK, |
| | Number of Investigators | 150-180 |
| | Approximate Number of Patients Per Site | 1-2 subjects/site |
| | Enrolment Rate | .5-1 patient per site every month |
| | Duration of Patient Participation | upto 6 cycles plus follow up period ~1 year |
| | -Screening/Run-In | <28 days |
| | - # of cycles | 6 |
| | -Follow-Up | 6 months |
| | -Survival Follow-Up | SAA |
| | Number of Protocol Summary Translations | French, Italian, Spanish, German, Danish, 3-5 Eastern Europe Translations, Mexico. |
| | Number of Full Protocol Translations | SAA |
| | Number of Informed Consent Translations | SAA |
| | Number of Investigators' Meetings | 1 per region |
| | Number of Protocol Amendments | 2 |

Figure 11-C

| Clincal Information | | |
|---|---|---|
| | Total Number of Monitoring Visits | Monitoring frequency every 6-8 weeks. |
| | -Potential sites Identified | |
| | -Pre-Study Evaluation (<1.2 X # ctrs) | 40 |
| | -Initiation (1 X # ctrs) | 150 |
| | -Interim Monitoring (IM) | every 6-8 weeks |
| | - IM Freq (enrollment) | within 3 weeks of FPI or sooner |
| | - IM Freq (treatment) | every 6-8 weeks |
| | - IM Freq (followup) | 2-3 months |
| | Number of Co-Monitoring Visits | 20 |
| | -Close-Out | 150 |
| | Total Number of Monitoring & close out Visits | |
| | Duration of Monitoring Visits (Hours) | 6 hours |
| | -Initiation | 24 (including travel/prep time) |
| | -Interim | 24 (including travel/prep time) |
| | -Close-Out | 24 (including travel/prep time) |
| | | |
| Project Management | | |
| | Number of COMPANY/CRO Project Team Meetings | Quarterly meetings |
| | Number of internal face-to-face CRO Project Team Meetings (1 kick-off meeting) | 6 |
| | COMPANY/CRO Project Team Teleconferences | Weekly |
| | Internal CRO project team teleconferences | TBD |
| Central Lab / Readers/ Special Assessments | | |
| | Central lab (Estrogen, LDH) | All labs |
| | | |
| | Local Labs: | Chem/cbc |

Figure 11-D

| Data Management | | |
|---|---|---|
| | # of Unique CRF Pages | 33 |
| | # of CRF Pages/ Completed Patient | 209 |
| | # of CRF Pages/ Screen Failure Patients | None |
| | Will Screen Fail CRFs Be Processed (yes/no) | None |
| | # of CRF Pages/ Early Withdrawal | $23+(16 \times C)$, C=# of cycles |
| | Total # of CRFs to be Processed by Data Management | |
| | # of Queries/ Patient | 20 |
| | # of Manually Coded Items/ Patient | None |
| | # of Other Electronic Data Sources | One, central lab |
| | Data Transfers: | |
| | # of Cumulative Dirty DB Transfers | Twelve |
| | # of Cumulative Clean DB Transfers | Six |
| | # of Incrementally Clean DB Transfers | None |
| | Interim Analysis | |
| | # of Interim Analyses | 1 |
| | # of Interim Analyses to Support Planned Interim Analyses | 1 |
| | | |
| | Will there be an SAE Reconciliation to the Clinical Database (yes/no) | yes |
| | DSMC (yes/no) | no |
| | # of Times DSMC will Meet | |
| | Annual IND Filing (yes/no) | yes |

Figure 11-E

| DESCRIPTION | RESPONSIBILITIES | | | ESTIMATED DIRECT COSTS $ US | | | | | ESTIMATED PASS-THROUGH COSTS $ US | | | | |
|---|---|---|---|---|---|---|---|---|---|---|---|---|---|
| | Sponsor | Vendor | Joint | n/a | Unit Type | ITEM TOTAL | | | SECTION SUB TOTAL | Unit Type | ITEM TOTAL | | SECTION SUB TOTAL |
| | | | | | | # Units | Price per Unit | Item Total | | | # Units | Price per Unit | Item Total | |
| 1 Project Management | X | X | X | X | | | | | 1,394,180 | | | | | |
| 1.1 Time Line Management | X | X | X | | per month | 35 | 18,500 | 647,500 | 647,500 | | | | | |
| 1.2 Team Management | X | X | X | | | | | | 414,224 | | | | | |
| 1.2.1 Status Reports | | X | | | per patient | 300 | 500 | 150,000 | | | | | | |
| 1.2.1.1 Essential Doc. Version Tracking (approved. Prot; ICF; CRF; IB) | | X | | | | | | | | | | | | |
| 1.2.1.2 Initiation (Ess. Doc tracking by country and site) | | X | | | | | | | | | | | | |
| 1.2.1.3 Pt Recruitment | X | | | | | | | | | | | | | |
| 1.2.1.4 Monitoring (Visits and reports) | | X | | | | | | | | | | | | |
| 1.2.1.5 CRF retrieval | | X | | | | | | | | | | | | |
| 1.2.1.6 Queries (rate; closed; pending) | | X | | | | | | | | | | | | |
| Direct Cost | | X | | | | | | | | | | | | |
| 1.2.1.8 SAE | | X | | | | | | | | | | | | |
| 1.2.1.9 Invest Grant payment | | | X | | per site, per month | 4500 | 50 | 225,000 | | | | | | |
| 1.2.1.10 Vender payments | | | X | | | | | | | | | | | |
| 1.2.1.11 other | | X | | | | | | | | | | | | |
| 1.2.2 Task List (Wkly Updates) | | X | | | | | | | | | | | | |
| 1.2.3 Issues/Decision Log (Wkly Updates) | | X | | | | | | | | | | | | |
| 1.2.4 Agenda | | X | | | per month | 35 | 1,000 | 39,224 | | | | | | |

Figure 11-F

| | | | | | | | |
|---|---|---|---|---|---|---|---|
| 1.2.5 Weekly Monitoring Team Meetings | X | | | | | | |
| 1.2.6 Frequently Asked Questions for sites (Wkly) | X | | | | | | |
| 1.2.7 Study News Letter- (Mo/Qtr) (CRF completion updates; Protocol Clarifications; Freq Asked Questions; AE coding help) | X | | | | | | |
| 1.3 Training | X | | | | 3,376 | 32,456 | |
| 1.3.1 Project Familization | X | | | | | | |
| 1.3.2 CRO Kick Off Mtg | X | per day | 14100 | 1 | 16,060 | travel+ accomodations+ meals+ ground transportation+ Catering; room rental+ office supplies | TBD |
| 13.3 | | | | | | | |
| 1.4 Recruitment Plan | X | | | | 150,000 | 150,000 | |
| 2 Medical Management | X | | | | | | |
| 2.1 Medical Monitoring/ PV | X | per day | 6510 | 2 | 13,020 | | |
| 2.1.1 Medical Monitor | X | | | | | | |
| 2.1.2 SAE Initial &Follow-up Reports | X | per SAE. FUP | 350 | TBD | TBD | per shipment | TBD TBD TBD |
| 2.1.3 SAE Narrative as part of SAE Rpt | X | | | | | | |
| 2.1.4 24 hr Med non SAE coverage | X | | | | | | |

Figure 11-G

| | | | | | | | | | |
|---|---|---|---|---|---|---|---|---|---|
| 2.1.5 Reportable Determination | X | | | | | | | | |
| 2.1.6 CRF or Table/Listing | X | | | | | | | | |
| 2.1.7 Generation of IND / CIOMOS safety letter | X | | | per submission | TBD | 100 | TBD | | |
| 2.1.8 Site Safety Report Submission | | X | | | | | | | |
| 2.1.9 Develop and maintain safety database | | X | | | | | | | |
| 2.1.10 Reconcile safety database with AE data base | | | | | | | | | |
| 2.1.11 Distribute SAE and safety updates per GCP to sites | | X | | per SAE, per site | TBD | 75 | TBD | | |
| 2.1.12 DMC management/safety updates | | X | | | | | | | |
| 2.2 Quality Plan | | X | | | | | | | |
| 2.2.1 Vendor Audits | | X | | | | | | | |
| 2.2.2 Site Audits | | X | | | | | | | |
| 2.3 Records Archiving & Management | | X | | | | | | | |
| 3 Vendor Administration | | X | | | | | | | |
| 3.1 Drug packaging facility payment | | X | | | | | per shipment | TBD TBD TBD | |
| 3.2 Central laboratory payments | | X | | | | | | | |
| 3.3 Assessment Payments | | X | | | | | per shipment | TBD TBD TBD | |
| 3.4 Central Reader Payment | | X | | | | | | | |

Figure 11-H

| DESCRIPTION | RESPONSIBILITIES ||| | ESTIMATED DIRECT COSTS ||||| | ESTIMATED PASSTHROUGH COSTS ||||
|---|---|---|---|---|---|---|---|---|---|---|---|---|---|---|
| | Sponsor | VENDER | Joint | n/a | Unit Type | ITEM TOTAL - Unit | ITEM TOTAL - Price per Unit | ITEM TOTAL - Item Total | SECTION SUB TOTAL | Unit Type | ITEM TOTAL - Unit | ITEM TOTAL - Price per Unit | ITEM TOTAL - Item Total | SECTION SUB TOTAL |
| 4 Study Start Up | X | X | X | X | | | | | 914850 | | | | | |
| 4.1 Investigator Brochure/Pharmacy Brochure | | X | | | | | | | 7500 | | | | | |
| 4.1.1 Draft or update IB | X | | | | | | | | | | | | | |
| 4.1.2 Review and Approve | X | | | | | | | | | | | | | |
| 4.1.3 Distribute to Sites; IRB/IEC | | X | | | per site | 150 | 50 | 7500 | | per shipment | TBD | 50-100 | TBD | |
| 4.2 Protocol development | X | X | | | | | | | 7500 | | | | | |
| 4.2.1 Literature review, background research | X | | | | | | | | | | | | | |
| 4.2.2 Design and write protocol | X | | | | | | | | | | | | | |
| 4.2.3 Review Protocol | X | | | | | | | | | | | | | |
| 4.2.4 Approve protocol | X | | | | | | | | | | | | | |
| Direct Cost | | X | | | | | | | | | | | | |
| 4.2.6 Translate Protocol | | X | | | per page | TBD | 30 | TBD | | translation fees | TBD | 200/per page | TBD | |
| 4.2.7 Copy & Distribute Protocol to sites | | X | | | per site | 150 | 50 | 7500 | | per shipment | TBD | 50-100 | TBD | |
| 4.2.8 Protocol Amendments | X | | | | | | | | | | | | | |
| 4.3 Informed Consent Development | X | X | X | | | | | | | | | | | |
| 4.3.1 Draft Informed Consent Template | X | | | | | | | | | | | | | |
| 4.3.2 IC Template review and approval | | | X | | | | | | | | | | | |
| 4.3.3 IC Translation | | X | | | per page | TBD | 30 | TBD | | translation fees | TBD | 200/per page | TBD | |
| 4.4 CRF (see also DM) | X | X | | | | | | | | | | | | |
| 4.4.1 Approve CRF's and patient assessment booklets | X | | | | | | | | | | | | | |
| 4.4.2 CRF completion conventions | | | X | | | | | | | | | | | |
| 4.5 Regulatory Submissions | | X | | | | | | | 318750 | | | | | |
| EUDRACT | | | | | per item | 1 | 250 | 250 | | per shipment | TBD | TBD | TBD | |
| IMPdossier IND adaptation | | | | | per item | 1 | 20,000 | 20000 | | per shipment | TBD | TBD | TBD | |

Figure 11-I

| Task | | | | | | | |
|---|---|---|---|---|---|---|---|
| 4.5.1 Manage regulatory submissions (based on FDA IND docs) | x | | | | | | |
| Health Authorities | | | | | per shipment+ submission fees | TBD | TBD | TBD |
| IRB/ EC | | | per item | 9 | 10,500 | 94500 | | | |
| | | | per item | 136 | 1,500 | 204000 | per shipment+ submission fees | TBD | TBD | TBD |
| 4.5.2 Manage regulatory updates | x | | | | | | |
| 4.6 Investigator recruitment and Selection | x | #REF! | | | | 187500 | |
| 4.6.1 Develop list of potential investigators | | x | | | | | |
| 4.6.2 Qualification Telephone surveys | x | | per site | 150 | 250 | 37500 | |
| 4.6.3 Pre-study Qualification Visits | x | | | | | | |
| 4.6.3.1 Conduct site qualification visits | x | | per site | TBD | 2000 | TBD | travel+ accomodation + meals+ ground transportation | TBD | TBD | TBD |
| 4.6.3.2 Provide written site evaluation report | | x | | | | | |
| 4.6.4 Select sites | | x | | | | | |
| 4.6.5 Prepare Investigator contract | x | | | | | | |
| 4.6.6 Negotiate investigator grants (site budgets) | x | | | | | | |
| 4.6.7 Collect essential and reg documents | x | | per site | 150 | 1000 | 150000 | |
| 4.8 Drug Supply | x | | | | | | |
| 4.8.1 Arrange drug packaging | x | | | | | | |
| 4.8.2 Arrange drug labeling | x | | | | | | |

Figure 11-J

| Task | | | | | | | | |
|---|---|---|---|---|---|---|---|---|
| 4.8.3 Drug storage and distribution | x | | | | | | | |
| 4.9 Patient randomization (IVRS?) (See Biostats) | | x | | | | | | |
| 4.1 IRB/IEC | | x | | | | | | |
| 4.10.1 Select Central IRB | | x | | | | | | |
| 4.10.2 Manage Ethics Committee/IRBs submissinos | | x | | | | | | |
| 4.10.3 Managage Regulatory Submissions | | x | | | | | | |
| 4.11 Pk Assessments | | x | | | | | | |
| 4.11.1 Identify Labs, NDA, RFP | x | | | | | | | |
| 4.11.2 Vendor Audits | x | | | | | | | |
| 4.11.3 Develop/Transfer procedures | x | | | | | | | |
| 4.11.4 Per patient cost of Sample kits | x | | | | | | | |
| 4.11.5 Shipping, testing, and storage procedures | x | | | | | | | |
| 4.11.6 Sample archiving | x | | | per lab. | TBD | TBD | | |
| 4.11.7 Electronic Data Collection | | x | | | | | | |
| 4.11.8 Data Transfer | | x | | | | | | |
| 4.12 Central laboratory | | x | | | | | | |
| 4.12.1 Identify Labs, NDA, RFP | | x | | | 1500 | | | |
| 4.12.2 Vendor Audits | | | | | | | | |
| 4.12.3 Per patient cost of Sample kits | | x | | | | | | |
| 4.12.4 Per patient cost of lab tests | | | | | | | | |
| 4.12.5 Sample archiving | | x | | | | | | |
| 4.12.6 Electronic Data Collection | | x | | | | | | |
| 4.12.7 Data Transfer | | x | | | | | | |
| 4.13 Site Study Binders | | x | | | | | | |
| 4.13.1 Site Regulatory Binder | | x | | | | | | |
| 4.13.2 Site Study Binder | | x | | | | | | |
| 4.13.3 Site Pharmacy Binder | | x | | | | | | |

Figure 11-K

| | | | | | | | | | | | |
|---|---|---|---|---|---|---|---|---|---|---|---|
| 4.13.4 Site pK Binder | x | | | | | | | | | | |
| 4.14 Set Up CTMF | | | | | | | | | TBD | TBD | TBD |
| CTMF set-up | | | x | per country | 9 | 500 | 4500 | office supplies+ shipment | TBD | TBD | TBD |
| | | | | per patient | 300 | 500 | 150000 | 154500 | | | |
| CTMF maintainance | | | | | | | | | | | |
| 4.15 Recruit Independent Data Monitoring committee | | | x | | | | | | | | |
| 4.14 Investigator's meeting | | | | | | | | travel+ accomodation + meals+ ground transportation + Catering; room rental+ office supplies | TBD | TBD | TBD |
| | | | | | | | | 239100 | | | |
| 4.14.1 Location | x | | x | | | | | | | | |
| 4.14.2 Agenda | x | x | | | | | | | | | |
| 4.14.3 Attendee list | | x | | | | | | | | | |
| 4.14.4 Travel arrangements | | x | | | | | | | | | |
| 4.14.5 Run meeting | | x | | | | | | | | | |
| 4.14.6 Presentations | | x | | | | | | | | | |
| 4.14.7 Meeting materials/Bindes | | | x | per site | 150 | 1500 | 225000 | | | | |
| 4.14.8 Attendance | x | | x | per day | 1 | 14100 | 14100 | | | | |

Figure 11-L

| DESCRIPTION | RESPONSIBILTIES | | | | ESTIMATED DIRECT COSTS | | | | | ESTIMATED PASSTHROUGH COSTS | | | |
|---|---|---|---|---|---|---|---|---|---|---|---|---|---|
| | Sponsor | VENDER | Joint | n/a | Unit Type | ITEM TOTAL | | | Unit Type | Unit | ITEM TOTAL | | SECTION SUB TOTAL |
| | | | | | | Unit | Price per Unit | Item Total | SECTION SUB TOTAL | | | Price per Unit | Item Total | |
| 5 Initiation and Monitoring | X | X | | | | | | | 1,702,500 | | | | | |
| 5.1 Initiation | | X | | | | | | | | | | | | |
| 5.1.1 Prestudy Documentation | | X | | | | | | | | | | | | |
| 5.1.3 Complete initiation visit report | | X | | | | | | | | | | | | |
| 5.2 Interim Monitoring | | X | | | | | | | 1,140,000 | | | | | |
| 5.2.1 Conduct monitoring visits | | | | | per visit | 600 | 1,900 | 1,140,000 | | travel+ accomodation+ meals+ ground transportation | TBD | TBD | TBD | |
| 5.2.2 Verify 100% of source documentation | | X | | | | | | | | | | | | |
| 5.2.3 Resolve edits/queries with site | | X | | | | | | | | | | | | |
| 5.2.4 Review drug records | | X | | | | | | | | | | | | |
| 5.2.5 Review lab storage | | X | | | | | | | | | | | | |
| Direct Cost | | X | | | | | | | | | | | | |
| 5.2.7 Interim Monitoring Visit report | | X | | | | | | | | | | | | |
| 5.2.8 Complete interim monitoring report | | X | | | | | | | | | | | | |
| 5.3 Site Close-Out | X | X | | | | | | | 225000 | | | | | |
| 5.3.1 Conduct site close-out visits | | X | | | per visit | 150 | 1500 | 225000 | | travel+ accomodations+ meals+ ground transportation | TBD | TBD | TBD | |
| 5.3.2 Site files complete; records archive | X | | | | | | | | | | | | | |

Figure 11-M

| | | | | | | |
|---|---|---|---|---|---|---|
| 5.3.3 data queries resolved | x | | | | | Included in close-out visit |
| 5.3.4 sample archival discussed | x | | | | | Included in close-out visit. |
| 5.3.5 drug reconciled | x | | | | | Included in close-out visit |
| 5.3.6 Survival | x | | | | | Included in close-out visit |
| 5.3.7 Provide close-out trip report | x | | | | | Included in close-out visit |
| 5.4 Site General Administration | x | | | 337500 | | |
| 5.4.1 Weekly telephone contact with sites | | per site per month | 4500 | 75 | 337500 | Routine site management |
| 5.4.2 Brief In-person site contact | x | | | | | Included in above tasks |
| 5.4.3 Investigator /institution grant administration | x | | | | | Included in 1.2.1.9 |
| 5.4.4 Provide newsletters | x | | | | | Included in Project Management |
| 5.4.5 Provide helpdesk for study conduct (unrelated to eCRF) | x | | | | | Included in weekly tel. Contacts |

Figure 11-N

| DESCRIPTION | RESPONSIBILITIES ||||| ESTIMATED DIRECT COSTS ||||| ESTIMATED PASSTHROUGH COSTS ||||
| --- | --- | --- | --- | --- | --- | --- | --- | --- | --- | --- | --- | --- | --- |
| | Sponsor | VENDER | Joint | n/a | Unit Type | Unit | Price per Unit | Item Total | SECTION SUB TOTAL | Unit Type | Unit | Price per Unit | Item Total | SECTION SUB TOTAL |
| 6 Data Management | X | X | X | | | | | | 614,336 | | | | | |
| 6.1 Data Project Management | | X | | | | 1 | 52,824 | 52,824 | 52,824 | | | | | |
| 6.2 Develop Data Management and Quality Plan | | X | | | DMOP | 1 | 23,136 | 23,136 | 23,136 | | | | | |
| 6.2.1 Collaborate, review, and approve DM and DQ Plan | X | | | | | | | | | | | | | |
| 6.3 Status Reports CRFs; Data Entry; Queries | | X | | | uniques | 33 | 264 | 8,712 | 8,712 | | | | | |
| 6.4 Client Conference Calls | | | X | | weekly | 128 | 132 | 16,896 | 16,896 | | | | | |
| 6.4 Client Conference Calls | | | X | | bi-weekly | 64 | 113 | 7,232 | 7,232 | | | | | |
| 6.5 CRFs | | | X | | Unique | 33 | 283 | 9,323 | 9,323 | | | | | |
| 6.5.1.1 Provide CRFs/Paper or Electronic Draft CRFs | | | | | | | | | | | | | | |
| 6.5.1.2 Design CRFs Direct Cost | | | | | | | | | | | | | | |
| 6.5.1.4 Approve CRFs | | | | | | | | | | | | | | |
| 6.5.2 Print CRFs | | | | | | | | | | per CRF | 62,700 | 250 | 76,350 | 76,350 |
| 6.5.3 Distribute CRFs to sites | | X | | | | | | | | | | | | |
| 6.5.4 Electronic CRF | | | | | | | | | | | | | | |

Figure 11-O

| | | | | | | | | | | |
|---|---|---|---|---|---|---|---|---|---|---|
| 6.5.4.1 Server/Datase Configeration & Qualification | | X | | | | | | | | |
| 6.5.4.2 eCRF Design | | X | | | | | | | | |
| 6.5.4.3 eCRF Programming | | X | | | | | | | | |
| 6.5.4.4 eCRF QC | | X | | | | | | | | |
| 6.5.4.5 eCRF Approval | X | | | | | | | | | |
| 6.5.4.6 eCRF Deployment | | X | | | | | | | | |
| 6.5.4.7 eCRF Completion conventions | | | X | | | | | | | |
| 6.6 Data Base Administration | X | X | X | | | | | | | |
| 6.6.1 Data Base Specification | | X | | | | | | | | |
| 6.6.2 Data Base Design | | X | | DB Setup | 30,492 | 30,492 | | | | |
| 6.6.3 Approve DB Design | X | | | | | | | | | |
| 6.6.4 Data Base QC | | | X | | | | | | | |
| 6.6.5 Data Base Audit | | X | X | | 11,639 | 11,639 | | | | |
| 6.6.6 Data Base Documentation | | X | | | | | | | 42,131 | |
| 6.7 Edit Checks | | X | X | | | | | | | |
| 6.7.1 Edit Check Specifications | | X | X | | | | 194,840 | | | |
| 6.7.2 Edit Check Programming | | X | | | | 194,840 | | | | |
| 6.7.3 Edit Check QC | | | X | | | | | | | |

Figure 11-P

| | | | | | | | | | |
|---|---|---|---|---|---|---|---|---|---|
| 6.8 Self-Evident Edit Checks | X | | | | | | | | |
| 6.9 Data Entry | | X | | | | | | | |
| 6.9.1 eCRF at Site | | X | | | | | | | |
| 6.9.2 paper - Double Data entry | | | | CRF page | 62,700 | 194,762 | | | |
| 6.1 Dictionary Coding | | | X | | | | | | |
| 6.10.1 SAE Coding | | | X | CRFs | 300 | 132 | 39,600 | 39,600 | |
| 6.10.2 Mediation Coding | | | X | | | | | | |
| 6.11 CRF storage or imaging | | | | | | | | | |
| 6.12 Central Laboratory Data integration | | X | | | | | | 15,640 | |
| 6.12.1 Lab Normal Ranges | | X | | data Integration | | | 15,640 | | |
| 6.13 Central Scan or X ray data | | X | | | | | | | |
| 6.14 pK or -Special Assessment Data | | X | | | | | | | |
| 6.15 Query Generation and Query Management | | X | X | | | | | | |
| 6.15.1 Site generated Queries | | X | | | | | | | |
| 6.15.2 CRA Generated Queries | | | X | | | | | | |

Figure 11-Q

| | | | | | | | | | | |
|---|---|---|---|---|---|---|---|---|---|---|
| 6.15.3 Listing Review generated Queries | | | X | | | | | | | |
| 6.15.4 Central Reads generated queries | | | | | | | | | | |
| 6.15.5 SAE - AE reconciliation | | | X | | | | | | | |
| 6.16 Monthly Transfer SAS datafiles | X | | | | | | | | | |
| 6.17 Track CRF, Queries, patients | X | | | | | | | | | |
| 6.18 Database Maintenance, Hosting and Support | X | monthly | | 35 | 264 | 9,240 | 9,240 | | | |

Figure 11-R

| DESCRIPTION | RESPONSIBILITIES ||||  | ESTIMATED DIRECT COSTS |||| ESTIMATED PASSTHROUGH COSTS ||||
|---|---|---|---|---|---|---|---|---|---|---|---|---|---|
| | Sponsor | VENDER | Joint | n/a | Unit Type | Unit | ITEM TOTAL: Price per Unit | ITEM TOTAL: Item Total | SECTION SUB TOTAL | Unit Type | ITEM TOTAL: Unit | ITEM TOTAL: Price per Unit | ITEM TOTAL: Item Total | SECTION SUB TOTAL |
| 8 Drug Supply Management | X | X | X | | | | | | 87300 | | | | | |
| 8.1 Drug Supply Plan | X | X | X | | | | | | 87300 | | | | | |
| 8.1.1 Drug Supply | X | | | | | | | | | | | | | |
| 8.1.2 Packaging | X | | | | | | | | | | | | | |
| 8.1.3 Inventory Management | X | | | | | | | | | | | | | |
| 8.1.4 Randomization | X | | | | | | | | | | | | | |
| 8.1.5 Pt level lot tracking | X | | | | | | | | | | | | | |
| 8.1.6 Distributor management | X | | | | | | | | | | | | | |
| 8.1.7 Country Specific Labels | X | | | | | | | | | | | | | |
| 8.1.8 Import licenses | | X | | | per country | 7 | 3900 | 27300 | | | | | | |
| Direct Cost | | | | | | | | | | | | | | |
| 8.1.10 Country Depots | X | | | | | | | | | | | | | |
| 8.1.8 Within Country Compartor Procurement | X | | | | | | | | | | | | | |

Figure 11-S

| | | | | | | | |
|---|---|---|---|---|---|---|---|
| 8.1.12 Shipping requirements (Hazardous?) | x | | | | | | |
| 8.1.13 Shipper | x | | | | | | |
| 8.1.14 Drug Distruction | | x | per site | 150 | 400 | 60000 | |
| 8.1.15 Final Reconciliation | | x | | | | | |
| 8.1.16 Ancillary Supplies | x | | | | | | |
| 8.2 Supply Study Drug for packaging | x | x | | | | | |
| 8.2.1 Identify vendors for compators | x | | | | | | |
| 8.2.2 Import Licenses and Customs Clearance | | x | | | | | |
| 8.3 Package Study Drug | x | | | | | | |
| 8.4 Produce Randomization Code | x | | | | | | |
| 8.5 Label study drug | x | | | | | | |
| 8.6 Ship study drug to site | | x | | | | | |
| 8.7 Store study drug | | x | | | | | |
| 8.8 study drug accountability | | x | | | | | |
| 8.9 Perform post-study drug accountability | | x | | | | | |
| 12 Study drug disposition & accountability | | x | | | | | |

Figure 11-T

| DESCRIPTION | RESPONSIBILITIES ||| ESTIMATED DIRECT COSTS ||||| ESTIMATED PASSTHROUGH COSTS ||||
|---|---|---|---|---|---|---|---|---|---|---|---|---|
| | Sponsor | VENDER | Joint | n/a | Unit Type | ITEM TOTAL ||| SECTION SUB TOTAL | Unit Type | ITEM TOTAL ||| SECTION SUB TOTAL |
| | | | | | | Unit | Price per Unit | Item Total | | | Unit | Price per Unit | Item Total | |
| 9. Labs and Assessments | | | | | | | | | | | | | | |
| 9.1 Central lab | | | X | X | | | | | | | | | | |
| 9.1.1 per patient sampling kit cost | | | X | | | | | | | | | | | |
| 9.1.2 per patient testing cost | | | X | | | | | | | | | | | |
| 9.1.3 per patient shiping est. | | | X | | | | | | | | | | | |
| 9.1 pK Lab | | | | X | | | | | | | | | | |
| 9.1.1 Test Validation Charges | | | | | | | | | | | | | | |
| 9.1.2 per patient sampling kit cost | | | | | | | | | | | | | | |
| 9.1.3 per patient testing cost | | | | | | | | | | | | | | |
| 9.1.4 per patient shiping est. | | | | | | | | | | | | | | |
| Direct Cost | | | | | | | | | | | | | | |
| 9.2 Central Readers | | | | | | | | | | | | | | |

Figure 11- U

| DESCRIPTION | RESPONSIBILTIES ||| ESTIMATED DIRECT COSTS ||||| ESTIMATED PASSTHROUGH COSTS ||||
|---|---|---|---|---|---|---|---|---|---|---|---|
| | Sponsor | VENDER | Joint | n/a | Unit Type | ITEM TOTAL ||| SECTION SUB TOTAL | Unit Type | ITEM TOTAL ||| SECTION SUB TOTAL |
| | | | | | | Unit | Price per Unit | Item Total | | | Unit | Price per Unit | Item Total | |
| 7 Statistical Analysis | X | | | | | | | | | | | | | |
| 7.1 Statistical Analysis Plan | X | | | | | | | | | | | | | |
| 7.1.1 Develop Analysis Plan | X | | | | | | | | | | | | | |
| 7.1.2 Review and Approve SAP | X | | | | | | | | | | | | | |
| 7.1.3 Number of tables (unique/total) | X | | | | | | | | | | | | | |
| 7.1.4 Number of Listings (unique/total) | X | | | | | | | | | | | | | |
| 7.1.5 Number of figures (unique/total) | X | | | | | | | | | | | | | |
| 7.2 Randomization Plan (IVRS?) | X | | | | | | | | | | | | | |
| 7.3 Data Monitoring Committee | X | | | | | | | | | | | | | |
| 7.4 Table, Listing and Figure Programing | X | | | | | | | | | | | | | |
| Direct Cost | X | | | | | | | | | | | | | |
| 7.7 Query Generation | X | | | | | | | | | | | | | |
| 7.7 Interm Analysis | X | | | | | | | | | | | | | |
| 7.8 Draft T/L/F | X | | | | | | | | | | | | | |
| 7.9 Blinded/ Mock T/L/F | X | | | | | | | | | | | | | |

Figure 12-A

Key Unit Assumptions

| Unit | One Month Follow-up | Six Month Follow-up | One Year Follow-up | Assumptions |
|---|---|---|---|---|
| Patients | | | | |
| Patients Screened | 400 | 400 | | 400 patients |
| Screen Failure Rate | 25 | 25 | | 25 % |
| Patient Randomized/Enrolled | 300 | 300 | | 300 patients |
| Patient Discontinuation Rate | 0 | 0 | | 0 % |
| Patient Completed/Evaluable | 300 | 300 | | 300 patients |
| SAEs | 300 | 300 | | 300 SAEs |
| Randomized Patient SAE Rate | 100 | 100 | | 100 % |
| Sites | | | | |
| Sites | 185 | 185 | | 185 total sites |
| | 55 | 55 | | 55 sites (North America) |
| | 120 | 120 | | 120 sites (Europe) |

Figure 12-B

| Unit | One Month Follow-up | Six Month Follow-up | One Year Follow-up | Assumptions |
|---|---|---|---|---|
| | 10 | 10 | 10 | 10 sites (Australia) |
| Sites with Local IRBs | 9 | 9 | | 9 sites |
| Percent Sites with Local IRBs | 20 | 20 | | 20 % |
| Pre-Study | | | | |
| XX Internal Kickoff Meeting | | 1 | 1 | 1 meeting |
| Duration | | 6 | 6 | 6 h/meeting |
| Hours Travel (CRAs) | | 0 | 0 | 0 h/meeting |
| XXX Kickoff Meeting | | 1 | 1 | 1 meeting (assumes US meeting) |
| Duration | | 4 | 4 | 4 h/meeting |
| Hours Travel | | 8 | 8 | 8 h/meeting |
| Project-Specific Training Meeting | | 1 | 1 | 1 meeting |
| Duration | | 4 | 4 | 4 h/meeting |
| Hours Travel | | 0 | 0 | 0 h/meeting |
| Telephone Pre-Study Screens | | 185 | 185 | 185 screens |
| Pre-Study Site Visits | | 40 | 40 | 40 visits |
| Hours Onsite | | 4 | 4 | 4 h/visit |
| Hours Preparation and Follow-up | | 4 | 4 | 4 h/visit |
| Hours Travel | | 8 | 8 | 8 h/visit (North America) |
| | | ~ 4 | ~ 4 | ~ 4 h/visit (Europe) |
| | | 4 | 4 | 4 h/visit (Australia) |
| Investigator Meeting | | 2 | 2 | 2 meetings (US and EU) |
| Duration | | 16 | 16 | 16 h/meeting |
| Hours Travel | | 8 | 8 | 8 h/meeting |
| Monitoring and Site Visits | | | | |
| Initiation Visits | | 185 | 185 | 185 visits |
| Hours Onsite | | 8 | 8 | 8 h/visit |
| Hours Preparation and Follow-up | | 5 | 5 | 5 h/visit |
| Hours Travel | | 8 | 8 | 8 h/visit (North America) |
| | | ~ 4 | ~ 4 | ~ 4 h/visit (Europe) |
| | | 4 | 4 | 4 h/visit (Australia) |
| Total Routine Monitoring Visits | | 3,700 | 4,070 | 4,440 visits (every 6 weeks during treatment, every 12 weeks during follow-up) |
| Routine Monitoring Visits per Site | | 20 | 22 | 24 visits/site |
| Hours Onsite | | 8 | 8 | 8 h/visit |
| Hours Preparation and | | 5 | 5 | 5 h/visit |

Figure 12-C

| Unit | One Month Follow-up | Six Month Follow-up | One Year Follow-up | Assumptions |
|---|---|---|---|---|
| Follow-up | | | | |
|     Hours Travel | | 8 | 8 | 8 h/visit (North America) |
| | | ~ 4 | ~ 4 | ~ 4 h/visit (Europe) |
| | | 4 | 4 | 4 h/visit (Australia) |
| Close-Out Visits | | 185 | 185 | 185 visits |
|     Hours Onsite | | 8 | 8 | 8 h/visit |
|     Hours Preparation and Follow-up | | 5.5 | 5.5 | 5.5 h/visit |
|     Hours Travel | | 8 | 8 | 8 h/visit (North America) |
| | | ~ 4 | ~ 4 | ~ 4 h/visit (Europe) |
| | | 4 | 4 | 4 h/visit (Australia) |
| Site Management | | | | |
| Grant Payments | | 10 | 12 | 14 payments/site (quarterly) |
| Newsletter Issues | | 30 | 36 | 42 issues/site (monthly) |
| Project Management | | | | |
| Vendor Management | | 4 | 4 | 4 vendors |
| Face-to-Face Meetings | | 5 | 5 | 5 meetings (semiannual – US based) |
|     Duration | | 6 | 6 | 6 h/meeting/attendee |
|     Hours Travel | | 8 | 8 | 8 h/meeting/attendee |
| Internal Team Teleconferences | | 151 | 202 | 254 teleconferences (weekly) |
|     Duration | | 1 | 1 | 1 h/teleconference |
| XXX Teleconferences | | 151 | 202 | 254 teleconferences (weekly) |
|     Duration | | 1 | 1 | 1 h/teleconference |
| Data Management | | | | |
| CRFs per Patient | | 119 | 119 | 119 CRFs/patient |
| Unique CRFs | | 23 | 23 | 23 unique CRFs |
| Copy CRFs | | 96 | 96 | 96 copy CRFs |
| Total CRFs | | 35,700 | 35,700 | 35,700 CRFs |
| Data Collection Modules | | 26 | 26 | 26 DCMs |
| Data Collection Instruments | | 119 | 119 | 119 DCIs |
| Discrepancies per Page | | 0.8 | 0.8 | 0.8 discrepancies/page |
| Queries | | 5,712 | 5,712 | 5,712 queries |
| Queries per Page | | 0.16 | 0.16 | 0.16 queries/page |
| Validation Checks | | 312 | 312 | 312 validation checks |
| Validation Checks per DCM | | 12 | 12 | 12 validation checks/DCM |
| CRFs 100% Verified | | 5,355 | 5,355 | 5,355 CRFs 100% verified |
| Coded Terms per Patient | | 20 | 20 | 20 coded terms/patient |

Figure 12-D

| Unit | One Month Follow-up | Six Month Follow-up | One Year Follow-up | Assumptions |
|---|---|---|---|---|
| Total Coded Terms | 6,000 | 6,000 | | 6,000 coded terms |
| Data Transfers to XXX | 19 | 19 | | 19 transfers |
| Electronic Downloads | 29 | 29 | | 29 downloads (monthly during treatment) |
| Lab Panels and Timepoints (electronic labs) | 3 | 3 | | 3 panels, 7 timepoints/panel (biochem, hem, urinalysis) |
| Interim Data Locks | 2 | 2 | | 2 locks |
| Interim Data Lock Sample Size | 13 | 13 | | 13 audited patients |
| Audited CRFs | 511 | 511 | | 511 audited CRFs |
| Final Audit Sample Size | 26 | 26 | | 26 audited patients |
| Audited CRFs | 3,094 | 3,094 | | 3,094 audited CRFs |
| Drug Safety | | | | |
| Investigator Alert Letters | 30 | 30 | | 30 letters |

Figure 12-E

CONFIDENTIAL

Section 7 Budget

7.1 Budget Summary

The total budget for the project assuming one month of follow-up is $23,867,938 with pass-through expenses estimated to total $3,134,508, for a project total of $27,002,446. A summary budget is listed below. For your review, XX has included the mapping to CTI's budget grid. The budgets in XXX's preferred format are provided in Attachment 1.

Table F  Budget Summary by Task – One Month Follow-up

| Task | Cost | Location in Cost Grid |
|---|---|---|
| Protocol Development | $ 6,092 | |
| Protocol Review, Non-XX Protocol | $ 6,092 | 4.2.3 |
| Pre-study Activities | $ 1,512,026 | |
| Study Planning | $ 48,786 | 1.1 |
| Data Management Plan | $ 18,181 | 6.2.1 |
| CTMS Setup | $ 5,560 | 1.1 |
| Develop IVRS Specifications | $ 2,364 | 4.9 |
| Project Feasibility | $ 62,789 | 1.1 |
| Site Identification, Recruitment, and Selection | $ 83,702 | 4.6.1 |
| Design, Review, and Production of CRFs | $ 25,611 | 6.5.1.2 |
| Printing, Distribution, and Tracking of CRFs | $ 5,339 | 6.5.2 |
| Develop, Assemble, and Distribute the Site Reference Manual and Site Regulatory Binders | $ 47,045 | 4.1.3 |
| Creation and Review of the Informed Consent Form | $ 6,756 | 4.3.1 |
| Translations | $ 12,564 | 4.2.6 |
| Central File Set Up of Site Files | $ 11,398 | 5.3.2 |
| Telephone Pre Study Visit | $ 112,028 | 4.6.2 |
| On-site Pre Study Visit - On-site | $ 24,276 | 4.6.3.1 |
| On-site Pre Study Visit - Travel | $ 34,797 | 4.6.3.1 |
| On-site Pre Study Visit - Prep and Follow-up | $ 24,276 | 4.6.3.2 |
| Investigator Meeting Planning, Preparation, and Follow-up | $ 25,550 | 4.14.6 |
| Investigator Meeting Travel and Attendance | $ 176,832 | 4.14.6 |
| Internal Kickoff Meeting | $ 41,562 | 1.1 |

Figure 12-F

CONFIDENTIAL

| Task | Cost | Location in Cost Grid |
|---|---|---|
| XXX Kickoff Meeting | $ 34,216 | 1.3.2 |
| Project Specific Training | $ 30,940 | 1.3.1 |
| IRB and EC Submissions | $ 376,812 | 4.5.1 |
| EC and Regulatory Annual Reports | $ 35,651 | 4.5.2 |
| Regulatory Document Collection and Drug Release | $ 173,625 | 4.6.7 |
| Regulatory Approvals/Weekly Tracking | $ 91,367 | 4.5.1 |
| Monitoring and Site Visits | $ 11,313,754 | |
| Site Initiation Visit- On-site | $ 224,056 | 5.1.1 |
| Site Initiation Visit - Travel | $ 149,534 | 5.1.1 |
| Site Initiation Visit - Prep and Follow-up | $ 140,035 | 5.1.2 |
| RMV - On-site | $ 4,481,120 | 5.2.1 |
| RMV - Travel | $ 2,990,680 | 5.2.1 |
| RMV - Prep and Follow-up | $ 2,800,700 | 5.2.7 |
| Close Out Visit - On-site | $ 224,056 | 5.3.1 |
| Close Out Visit - Travel | $ 149,534 | 5.3.1 |
| Close Out Visit - Prep and Follow-up | $ 154,039 | 5.3.7 |
| Site Management | $ 4,055,101 | |
| Routine Site Communication | $ 1,949,663 | 5.4.1 |
| Newsletters | $ 90,855 | 1.2.7 |
| Study & Site File Maintenance | $ 762,219 | 5.3.2 |
| Grants Administration | $ 213,590 | 1.2.1.9 |
| Clinical Support of Query Resolution | $ 69,432 | 5.2.3 |
| Annual IRB Renewals | $ 55,870 | 4.5.2 |
| CTMS Input and Support | $ 913,472 | 1.1 |
| Project Management | $ 5,207,620 | |
| Project Status Reports | $ 192,538 | 1.2.1 |
| Internal Project Team Teleconferences | $ 799,142 | 1.2.5 |
| XXX Teleconferences | $ 349,565 | 1.2.4 |
| Face-to-Face Meetings | $ 107,332 | 1.3.3 |
| Clinical Overall Supervision | $ 2,973,968 | 1.1 |
| Vendor Management and Payments | $ 90,184 | 1.2.1.10 |
| Review of Trip Reports | $ 547,952 | 1.2.1.4 |

Figure 12-G

CONFIDENTIAL

| Task | Cost | Location in Cost Grid |
|---|---|---|
| Data Management Overall Supervision | $ 146,940 | 1.1 |
| Drug Safety | $ 646,621 | |
| Develop Safety Management Plan | $ 8,912 | 2.1.2 |
| Development and Maintenance of Safety Database (ARISg) | $ 2,284 | 2.1.2 |
| Collection, Review, and Follow-up of Reports | $ 314,517 | 2.1.2 |
| Setup/Maintenance of SAE Files | $ 25,408 | 2.1.2 |
| Investigator Alert Letters | $ 245,661 | 2.1.8 |
| AE/SAE Reconciliation | $ 44,931 | 2.1.10 |
| Monthly Line Listings | $ 4,908 | 2.1.2 |
| DM (Paper) | $ 903,933 | |
| Annotate the CRF | $ 12,785 | 6.6.2 |
| Database Setup and Testing | $ 20,290 | 6.6.2 |
| Setup for Local Labs and Incoming Electronic Data Transfers | $ 4,928 | 6.6.2 |
| Setup for Medical Coding | $ 1,232 | 6.6.2 |
| Data Validation Programming | $ 16,016 | 6.6.2 |
| Data Validation Testing | $ 10,299 | 6.6.2 |
| Scanning and Indexing CRFs and Queries | $ 52,735 | 6.3 |
| Data Entry and Reconciliation (First Pass) | $ 65,538 | 6.9.2 |
| Data Entry and Reconciliation (Second Pass) | $ 65,538 | 6.9.2 |
| Manual Review of Data | $ 42,896 | 6.8 |
| Review Discrepancy Database | $ 181,240 | 6.3 |
| DCF Management | $ 168,910 | 6.3 |
| Reconciliation of AEs and SAEs | $ 21,632 | 6.15.5 |
| Reconciliation of Electronic Data or Local Lab Data | $ 5,757 | 4.12.6 |
| Loading of Electronic Data | $ 17,864 | 4.12.6 |
| Data Transfer to CTI | $ 14,630 | 6.16 |
| Data Filing and Tracking | $ 52,735 | 6.17 |
| Medical Coding | $ 61,243 | 6.10.2 |
| Initial Database QC Checks | $ 9,545 | 6.6.2 |
| 100% Verification of Key Variables | $ 32,069 | 6.6.2 |
| QC for Interim Lock | $ 13,609 | 6.6.4 |

Figure 12-H

CONFIDENTIAL

| Task | Cost | Location in Cost Grid |
|---|---|---|
| Final QC of Database | $ 18,974 | 6.6.4 |
| Setup of Listings and Reports in I-Review/SAS | $ 13,468 | 6.6.6 |
| Drug Supply Management | $ 199,414 | |
| Drug Importation & Licensing | $ 4,214 | 8.1.8 |
| Drug Shipping and Tracking | $ 146,158 | 5.2.4 |
| Drug Receipt and Destruction | $ 49,042 | 8.1.14 |
| Storage and Archiving | $ 23,378 | |
| Project File Maintenance | $ 18,732 | 5.3.2 |
| Archiving | $ 4,646 | 5.3.2 |
| Total Fees | $ 23,867,938 | |
| Total Pass-throughs | $ 3,134,508 | |
| Grand Total | $ 27,002,446 | |

The total budget for the project assuming one month of follow-up is $26,084,556 with pass-through expenses estimated to total $3,371,194, for a project total of $29,455,750. A summary budget is listed below.

Table G  Budget Summary by Task – Six Month Follow-up

| Task | Cost | Location in Cost Grid |
|---|---|---|
| Protocol Development | $ 6,142 | |
| Protocol Review, Non-XX Protocol | $ 6,142 | 4.2.3 |
| Pre-study Activities | $ 1,523,343 | |
| Study Planning | $ 49,209 | 1.1 |
| Data Management Plan | $ 18,312 | 6.2.1 |
| CTMS Setup | $ 5,600 | 1.1 |
| Develop IVRS Specifications | $ 2,388 | 4.9 |
| Project Feasibility | $ 63,325 | 1.1 |
| Site Identification, Recruitment, and Selection | $ 84,362 | 4.6.1 |
| Design, Review, and Production of CRFs | $ 25,828 | 6.5.1.2 |
| Printing, Distribution, and Tracking of CRFs | $ 5,389 | 6.5.2 |

Figure 12-I

CONFIDENTIAL

| Task | Cost | Location in Cost Grid |
|---|---|---|
| Develop, Assemble, and Distribute the Site Reference Manual and Site Regulatory Binders | $ 47,431 | 4.1.3 |
| Creation and Review of the Informed Consent Form | $ 6,803 | 4.3.1 |
| Translations | $ 12,652 | 4.2.6 |
| Central File Set Up of Site Files | $ 11,503 | 5.3.2 |
| Telephone Pre Study Visit | $ 112,860 | 4.6.2 |
| On-site Pre Study Visit - On-site | $ 24,464 | 4.6.3.1 |
| On-site Pre Study Visit - Travel | $ 35,084 | 4.6.3.1 |
| On-site Pre Study Visit - Prep and Follow-up | $ 24,464 | 4.6.3.2 |
| Investigator Meeting Planning, Preparation, and Follow-up | $ 25,760 | 4.14.6 |
| Investigator Meeting Travel and Attendance | $ 178,200 | 4.14.6 |
| Internal Kickoff Meeting | $ 41,880 | 1.1 |
| XXX Kickoff Meeting | $ 34,460 | 1.3.2 |
| Project Specific Training | $ 31,180 | 1.3.1 |
| IRB and EC Submissions | $ 379,469 | 4.5.1 |
| EC and Regulatory Annual Reports | $ 35,886 | 4.5.2 |
| Regulatory Document Collection and Drug Release | $ 174,850 | 4.6.7 |
| Regulatory Approvals/Weekly Tracking | $ 91,986 | 4.5.1 |
| Monitoring and Site Visits | $ 12,434,420 | |
| Site Initiation Visit- On-site | $ 225,720 | 5.1.1 |
| Site Initiation Visit - Travel | $ 150,718 | 5.1.1 |
| Site Initiation Visit - Prep and Follow-up | $ 141,075 | 5.1.2 |
| RMV - On-site | $ 4,965,840 | 5.2.1 |
| RMV - Travel | $ 3,315,796 | 5.2.1 |
| RMV - Prep and Follow-up | $ 3,103,650 | 5.2.7 |
| Close Out Visit - On-site | $ 225,720 | 5.3.1 |
| Close Out Visit - Travel | $ 150,718 | 5.3.1 |
| Close Out Visit - Prep and Follow-up | $ 155,183 | 5.3.7 |
| Site Management | $ 4,817,088 | |
| Routine Site Communication | $ 2,478,317 | 5.4.1 |
| Newsletters | $ 109,980 | 1.2.7 |
| Study & Site File Maintenance | $ 920,316 | 5.3.2 |

Figure 12-J

CONFIDENTIAL

| Task | Cost | Location in Cost Grid |
|---|---|---|
| Grants Administration | $ 258,333 | 1.2.1.9 |
| Clinical Support of Query Resolution | $ 69,920 | 5.2.3 |
| Annual IRB Renewals | $ 60,024 | 4.5.2 |
| CTMS Input and Support | $ 920,198 | 1.1 |
| Project Management | $ 5,517,680 | |
| Project Status Reports | $ 194,113 | 1.2.1 |
| Internal Project Team Teleconferences | $ 950,854 | 1.2.5 |
| XXX Teleconferences | $ 415,566 | 1.2.4 |
| Face-to-Face Meetings | $ 108,058 | 1.3.3 |
| Clinical Overall Supervision | $ 2,996,570 | 1.1 |
| Vendor Management and Payments | $ 91,001 | 1.2.1.10 |
| Review of Trip Reports | $ 599,699 | 1.2.1.4 |
| Data Management Overall Supervision | $ 161,820 | 1.1 |
| Drug Safety | $ 651,482 | |
| Develop Safety Management Plan | $ 9,001 | 2.1.2 |
| Development and Maintenance of Safety Database (ARISg) | $ 2,312 | 2.1.2 |
| Collection, Review, and Follow-up of Reports | $ 316,617 | 2.1.2 |
| Setup/Maintenance of SAE Files | $ 25,619 | 2.1.2 |
| Investigator Alert Letters | $ 247,734 | 2.1.8 |
| AE/SAE Reconciliation | $ 45,231 | 2.1.10 |
| Monthly Line Listings | $ 4,968 | 2.1.2 |
| DM (Paper) | $ 909,911 | |
| Annotate the CRF | $ 12,928 | 6.6.2 |
| Database Setup and Testing | $ 20,541 | 6.6.2 |
| Setup for Local Labs and Incoming Electronic Data Transfers | $ 4,992 | 6.6.2 |
| Setup for Medical Coding | $ 1,248 | 6.6.2 |
| Data Validation Programming | $ 16,224 | 6.6.2 |
| Data Validation Testing | $ 10,366 | 6.6.2 |
| Scanning and Indexing CRFs and Queries | $ 52,735 | 6.3 |
| Data Entry and Reconciliation (First Pass) | $ 65,538 | 6.9.2 |
| Data Entry and Reconciliation (Second Pass) | $ 65,538 | 6.9.2 |

Figure 12-K

CONFIDENTIAL

| Task | Cost | Location in Cost Grid |
|---|---|---|
| Manual Review of Data | $ 43,194 | 6.8 |
| Review Discrepancy Database | $ 182,668 | 6.3 |
| DCF Management | $ 170,338 | 6.3 |
| Reconciliation of AEs and SAEs | $ 21,782 | 6.15.5 |
| Reconciliation of Electronic Data or Local Lab Data | $ 5,809 | 4.12.6 |
| Loading of Electronic Data | $ 18,096 | 4.12.6 |
| Data Transfer to XXX | $ 14,782 | 6.16 |
| Data Filing and Tracking | $ 52,735 | 6.17 |
| Medical Coding | $ 62,005 | 6.10.2 |
| Initial Database QC Checks | $ 9,614 | 6.6.2 |
| 100% Verification of Key Variables | $ 32,364 | 6.6.2 |
| QC for Interim Lock | $ 13,707 | 6.6.4 |
| Final QC of Database | $ 19,109 | 6.6.4 |
| Setup of Listings and Reports in I-Review/SAS | $ 13,598 | 6.6.6 |
| Drug Supply Management | $ 200,949 | |
| Drug Importation & Licensing | $ 4,249 | 8.1.8 |
| Drug Shipping and Tracking | $ 147,308 | 5.2.4 |
| Drug Receipt and Destruction | $ 49,392 | 8.1.14 |
| Storage and Archiving | $ 23,541 | |
| Project File Maintenance | $ 18,865 | 5.3.2 |
| Archiving | $ 4,676 | 5.3.2 |
| Total Fees | $ 26,084,556 | |
| Total Pass-throughs | $ 3,371,194 | |
| Grand Total | $ 29,455,750 | |

Figure 12-L

CONFIDENTIAL

The total budget for the project assuming one month of follow-up is $28,567,888 with pass-through expenses estimated to total $3,607,731, for a project total of $32,175,619. A summary budget is listed below.

Table H  Budget Summary by Task – One Year Follow-up

| Task | Cost | Location in Cost Grid |
|---|---|---|
| Protocol Development | $ 6,272 | |
| Protocol Review, Non-XX Protocol | $ 6,272 | 4.2.3 |
| Pre-study Activities | $ 1,555,305 | |
| Study Planning | $ 50,143 | 1.1 |
| Data Management Plan | $ 18,682 | 6.2.1 |
| CTMS Setup | $ 5,680 | 1.1 |
| Develop IVRS Specifications | $ 2,436 | 4.9 |
| Project Feasibility | $ 64,698 | 1.1 |
| Site Identification, Recruitment, and Selection | $ 86,113 | 4.6.1 |
| Design, Review, and Production of CRFs | $ 26,327 | 6.5.1.2 |
| Printing, Distribution, and Tracking of CRFs | $ 5,503 | 6.5.2 |
| Develop, Assemble, and Distribute the Site Reference Manual and Site Regulatory Binders | $ 48,465 | 4.1.3 |
| Creation and Review of the Informed Consent Form | $ 6,956 | 4.3.1 |
| Translations | $ 12,947 | 4.2.6 |
| Central File Set Up of Site Files | $ 11,744 | 5.3.2 |
| Telephone Pre Study Visit | $ 115,080 | 4.6.2 |
| On-site Pre Study Visit - On-site | $ 24,944 | 4.6.3.1 |
| On-site Pre Study Visit - Travel | $ 35,766 | 4.6.3.1 |
| On-site Pre Study Visit - Prep and Follow-up | $ 24,944 | 4.6.3.2 |
| Investigator Meeting Planning, Preparation, and Follow-up | $ 26,288 | 4.14.6 |
| Investigator Meeting Travel and Attendance | $ 181,860 | 4.14.6 |
| Internal Kickoff Meeting | $ 42,744 | 1.1 |
| XXX Kickoff Meeting | $ 35,136 | 1.3.2 |
| Project Specific Training | $ 31,822 | 1.3.1 |
| IRB and EC Submissions | $ 387,596 | 4.5.1 |
| EC and Regulatory Annual Reports | $ 36,635 | 4.5.2 |

Figure 12-M

CONFIDENTIAL

| Task | Cost | Location in Cost Grid |
|---|---|---|
| Regulatory Document Collection and Drug Release | $ 178,815 | 4.6.7 |
| Regulatory Approvals/Weekly Tracking | $ 93,982 | 4.5.1 |
| Monitoring and Site Visits | $ 13,733,753 | |
| Site Initiation Visit- On-site | $ 230,160 | 5.1.1 |
| Site Initiation Visit - Travel | $ 153,658 | 5.1.1 |
| Site Initiation Visit - Prep and Follow-up | $ 143,850 | 5.1.2 |
| RMV - On-site | $ 5,523,840 | 5.2.1 |
| RMV - Travel | $ 3,687,792 | 5.2.1 |
| RMV - Prep and Follow-up | $ 3,452,400 | 5.2.7 |
| Close Out Visit - On-site | $ 230,160 | 5.3.1 |
| Close Out Visit - Travel | $ 153,658 | 5.3.1 |
| Close Out Visit - Prep and Follow-up | $ 158,235 | 5.3.7 |
| Site Management | $ 5,510,728 | |
| Routine Site Communication | $ 2,903,377 | 5.4.1 |
| Newsletters | $ 130,991 | 1.2.7 |
| Study & Site File Maintenance | $ 1,095,154 | 5.3.2 |
| Grants Administration | $ 307,024 | 1.2.1.9 |
| Clinical Support of Query Resolution | $ 71,282 | 5.2.3 |
| Annual IRB Renewals | $ 65,170 | 4.5.2 |
| CTMS Input and Support | $ 937,731 | 1.1 |
| Project Management | $ 5,938,640 | |
| Project Status Reports | $ 197,837 | 1.2.1 |
| Internal Project Team Teleconferences | $ 1,114,705 | 1.2.5 |
| XXX Teleconferences | $ 486,940 | 1.2.4 |
| Face-to-Face Meetings | $ 110,250 | 1.3.3 |
| Clinical Overall Supervision | $ 3,098,208 | 1.1 |
| Vendor Management and Payments | $ 92,901 | 1.2.1.10 |
| Review of Trip Reports | $ 658,592 | 1.2.1.4 |
| Data Management Overall Supervision | $ 179,207 | 1.1 |
| Drug Safety | $ 663,153 | |
| Develop Safety Management Plan | $ 9,161 | 2.1.2 |
| Development and Maintenance of Safety Database (ARISg) | $ 2,354 | 2.1.2 |

Figure 12-N

CONFIDENTIAL

| Task | Cost | Location in Cost Grid |
|---|---|---|
| Collection, Review, and Follow-up of Reports | $ 322,917 | 2.1.2 |
| Setup/Maintenance of SAE Files | $ 26,008 | 2.1.2 |
| Investigator Alert Letters | $ 251,522 | 2.1.8 |
| AE/SAE Reconciliation | $ 46,131 | 2.1.10 |
| Monthly Line Listings | $ 5,059 | 2.1.2 |
| DM (Paper) | $ 930,941 | |
| Annotate the CRF | $ 13,181 | 6.6.2 |
| Database Setup and Testing | $ 20,950 | 6.6.2 |
| Setup for Local Labs and Incoming Electronic Data Transfers | $ 5,088 | 6.6.2 |
| Setup for Medical Coding | $ 1,272 | 6.6.2 |
| Data Validation Programming | $ 16,536 | 6.6.2 |
| Data Validation Testing | $ 10,566 | 6.6.2 |
| Scanning and Indexing CRFs and Queries | $ 54,115 | 6.3 |
| Data Entry and Reconciliation (First Pass) | $ 67,323 | 6.9.2 |
| Data Entry and Reconciliation (Second Pass) | $ 67,323 | 6.9.2 |
| Manual Review of Data | $ 44,086 | 6.8 |
| Review Discrepancy Database | $ 186,740 | 6.3 |
| DCF Management | $ 174,304 | 6.3 |
| Reconciliation of AEs and SAEs | $ 22,232 | 6.15.5 |
| Reconciliation of Electronic Data or Local Lab Data | $ 5,951 | 4.12.6 |
| Loading of Electronic Data | $ 18,444 | 4.12.6 |
| Data Transfer to XXX | $ 15,067 | 6.16 |
| Data Filing and Tracking | $ 54,115 | 6.17 |
| Medical Coding | $ 63,238 | 6.10.2 |
| Initial Database QC Checks | $ 9,822 | 6.6.2 |
| 100% Verification of Key Variables | $ 33,141 | 6.6.2 |
| QC for Interim Lock | $ 14,001 | 6.6.4 |
| Final QC of Database | $ 19,514 | 6.6.4 |
| Setup of Listings and Reports in I-Review/SAS | $ 13,930 | 6.6.6 |
| Drug Supply Management | $ 205,025 | |
| Drug Importation & Licensing | $ 4,340 | 8.1.8 |

Figure 12-O

CONFIDENTIAL

| Task | Cost | Location in Cost Grid |
|---|---|---|
| Drug Shipping and Tracking | $ 150,183 | 5.2.4 |
| Drug Receipt and Destruction | $ 50,502 | 8.1.14 |
| Storage and Archiving | $ 24,071 | |
| Project File Maintenance | $ 19,297 | 5.3.2 |
| Archiving | $ 4,774 | 5.3.2 |
| Total Fees | $ 28,567,888 | |
| Total Pass-throughs | $ 3,607,731 | |
| Grand Total | $ 32,175,619 | |

7.2 Pass-Through Expenses

Expenses, such as travel, day-to-day shipping, printing, copying, and communication with XXX and the investigative sites, have been included in the budget as pass-through expenses. Major expenses including, but not limited to, travel outside of XX offices will be passed through, without mark-up, to XXX. XXX will be invoiced monthly for pass-through expenses as they are incurred by XX. The table below provides a breakdown of the estimated pass-through expenses for this project.

Please note that the IVRS bid found in Attachment 5 is not figured into the pass through cost estimates found below.

Table I    Estimated Pass-Through Expenses – One Month Follow-up

| Item | Cost |
|---|---|
| Travel | $ 2,588,131 |
| Meetings | $ 63,257 |
| General Project Overhead (phone & fax costs) | $ 113,535 |
| Site-related Pass-throughs (shipping) | $ 209,189 |
| Regulatory Fees | $ 2,588,131 |
| Estimated Pass-Through Expenses | $ 3,134,508 |

Table J    Estimated Pass-Through Expenses – Six Month Follow-up

| Item | Cost |
|---|---|
| Travel | $ 2,820,917 |
| Meetings | $ 63,257 |
| General Project Overhead (phone & fax costs) | $ 117,435 |

Figure 12-P

CONFIDENTIAL

| | | |
|---|---|---|
| Site-related Pass-throughs (shipping) | $ | 209,189 |
| Regulatory Fees | $ | 160,395 |
| Estimated Pass-Through Expenses | $ | 3,371,194 |

Table K  Estimated Pass-Through Expenses – One Year Follow-up

| Item | | Cost |
|---|---|---|
| Travel | $ | 3,053,704 |
| Meetings | $ | 63,257 |
| General Project Overhead (phone & fax costs) | $ | 121,185 |
| Site-related Pass-throughs (shipping) | $ | 209,189 |
| Regulatory Fees | $ | 160,395 |
| Estimated Pass-Through Expenses | $ | 3,607,731 |

7.3 Notes to the Budget

7.3.1 Cost-of-Business

In order to allow XXX to accurately anticipate total project costs, XX has incorporated cost-of-business rate increases into the project budget, with increases instituted at the beginning of each calendar year.

7.3.2 Exchange Rates

Please note that although the enclosed fees are stated in US dollars (USD), they are based on XX's international rate card based in Euros. For the purposes of this proposal, our Euro-based fees have been converted to USD using the exchange rate of 0.7581. Please note that due to the continued volatility of the USD in the foreign currency exchange markets, XX adopts a pricing policy whereby we apply the appropriate "monthly rate" at the time each budget is prepared. If following this proposal a subsequent revision is made, this may result in changes to the USD prices if a move in the monthly exchange rate has occurred.

If XX is successful in being awarded the conduct of this study, XX will discuss with XXX agreeable payment terms based upon either quoting the budget in Euros and invoicing monthly in USD at the current exchange rate or XX quoting in USD, and for contracting purposes, locking the exchange rates at the rate quoted in the final proposal. Invoices will be presented on a monthly basis for units performed during the current month in USD indexing from the contracted exchange rate to the exchange rate for the prevailing month.

Figure 13-A

| PROPOSED STUDY TARGET DATES | | |
|---|---|---|
| | Study Start Date | Q1-Q2 2007 |
| | Site Initiation (study set up 4 months) | March 2007 for site selection start |
| | Enrollment Period: | March/April 2007-December 2008 (18-24 months) |
| | | |
| | First Patient In | March/April 2007 (token USA pt) |
| | Last Patient In | March 2009 |
| | Treatment Period: | up to 6 cycles |
| | Last Patient Out | Sept 2009 |
| | Follow-up Period: | ~6 months |
| | Survival Follow up | SAA |
| | Interim Analysis | yes |
| | Last CRF in | TBD |
| | Clean Database Lock | Sept/Oct 2009 |
| | Statistical Analysis | TBD |
| | Clinical Study Report | Q4-2009 |
| | | |
| | | |

Figure 13-B

| PROJECT OVERVIEW | | |
|---|---|---|
| | Compound Name | XXXXXX |
| | Program Phase | Phase III |
| | Dosage Form | IV |
| | Indication | XXXXXX |
| | Study Design | Randomized, Comparative |
| | Patient Population | • Locally advanced or recurrent disease previously treated with radiation and/or surgery, or stage IIIB or IV |
| | Number of Patients | 300 total |
| | World Regions (US; EU; ** May need to greatly increase number of sites in these countries. These are the only countries we will consider) | Spain, France, Belgium, Germany, USA, Canada, Australia, Czech, UK, |
| | Number of Investigators | 150-180 |
| | Approximate Number of Patients Per Site | 1-2 subjects/site |
| | Enrolment Rate | .5-1 patient per site every month |
| | Duration of Patient Participation | upto 6 cycles plus follow up period ~1 year |
| | -Screening/Run-In | <28 days |
| | - # of cycles | 6 |
| | -Follow-Up | 6 months |
| | -Survival Follow-Up | SAA |
| | Number of Protocol Summary Translations | French, Italian, Spanish, German, Danish, 3-5 Eastern Europe Translations, Mexico. |
| | Number of Full Protocol Translations | SAA |
| | Number of Informed Consent Translations | SAA |
| | Number of Investigators' Meetings | 1 per region |
| | Number of Protocol Amendments | 2 |

Figure 13-C

| Clincal Information | | |
|---|---|---|
| | Total Number of Monitoring Visits | Monitoring frequency every 6-8 weeks. |
| | -Potential sites Identified | |
| | -Pre-Study Evaluation (<1.2 X # ctrs) | 40 |
| | -Initiation (1 X # ctrs) | 150 |
| | -Interim Monitoring (IM) | every 6-8 weeks |
| | - IM Freq (enrollment) | within 3 weeks of FPI or sooner |
| | - IM Freq (treatment) | every 6-8 weeks |
| | - IM Freq (followup) | 2-3 months |
| | Number of Co-Monitoring Visits | 20 |
| | -Close-Out | 150 |
| | Total Number of Monitoring & close out Visits | |
| | Duration of Monitoring Visits (Hours) | 6 hours |
| | -Initiation | 24 (including travel/prep time) |
| | -Interim | 24 (including travel/prep time) |
| | -Close-Out | 24 (including travel/prep time) |
| | | |
| Project Management | | |
| | Number of COMPANY/CRO Project Team Meetings | Quarterly meetings |
| | Number of internal face-to-face CRO Project Team Meetings (1 kick-off meeting) | 6 |
| | COMPANY/CRO Project Team Teleconferences | Weekly |
| | Internal CRO project team teleconferences | TBD |
| Central Lab / Readers/ Special Assessments | | |
| | Central lab (Estrogen, LDH) | All labs |
| | | |
| | Local Labs: | Chem/cbc |

Figure 13-D

| Data Management | | |
|---|---|---|
| | # of Unique CRF Pages | 33 |
| | # of CRF Pages/ Completed Patient | 209 |
| | # of CRF Pages/ Screen Failure Patients | None |
| | Will Screen Fail CRFs Be Processed (yes/no) | None |
| | # of CRF Pages/ Early Withdrawal | 23+(16xC), C=# of cycles |
| | Total # of CRFs to be Processed by Data Management | |
| | # of Queries/ Patient | 20 |
| | # of Manually Coded Items/ Patient | None |
| | # of Other Electronic Data Sources | One, central lab |
| | Data Transfers: | |
| | # of Cumulative Dirty DB Transfers | Twelve |
| | # of Cumulative Clean DB Transfers | Six |
| | # of Incrementally Clean DB Transfers | None |
| | Interim Analysis | |
| | # of Interim Analyses | 1 |
| | # of Interim Analyses to Support Planned Interim Analyses | 1 |
| | | |
| | Will there be an SAE Reconciliation to the Clinical Database (yes/no) | yes |
| | DSMC (yes/no) | no |
| | # of Times DSMC will Meet | |
| | Annual IND Filing (yes/no) | yes |

Figure 13-E

| DESCRIPTION | RESPONSIBILITIES | | | | ESTIMATED DIRECT COSTS | | | | | | ESTIMATED PASS-THROUGH COSTS | | | | | |
|---|---|---|---|---|---|---|---|---|---|---|---|---|---|---|---|---|
| | Sponsor | VENDER | Joint | n/a | Unit Type | # Units | ITEM TOTAL Price per Unit | ITEM TOTAL Item Total | SECTION SUB TOTAL | | Unit Type | # Units | ITEM TOTAL Price per Unit | ITEM TOTAL Item Total | SECTION SUB TOTAL |
| 1 Project Management | X | X | X | | | | | | 6,649,390 | | | | | | 140,499 |
| 1.1 Time Line Management | X | X | X | | month | 33 | 126,248 | 4,193,077 | 4,193,077 | | month | 33 | 2,773 | 92,085 | 92,085 |
| 1.2 Team Management | X | | X | | | | | | 2,283,826 | | | | | | 21,450 |
| 1.2.1 Status Reports | | X | X | | week | 133 | 1,448 | 192,538 | | | | | | | 21,450 |
| 1.2.1.1 Essential Doc. Version Tracking (approved. Prot; ICF; CRF; IB) | X | | | | | | | | | | | | | | |
| 1.2.1.2 Initiation (Ess. Doc tracking by country and site) | X | | | | | | | | | | | | | | |
| 1.2.1.3 Pt Recruitment | | X | | | | | | | | | | | | | |
| 1.2.1.4 Monitoring (Visits and reports) | X | | X | | report | 3,221 | 170 | 547,952 | | | | | | | |
| 1.2.1.5 CRF retrieval | | X | | | | | | | | | | | | | |
| 1.2.1.6 Queries (rate; closed; pending) | | X | | | | | | | | | | | | | |
| Direct Cost | | X | | | | | | | | | | | | | |
| 1.2.1.8 SAE | | X | | | | | | | | | | | | | |
| 1.2.1.9 Invest Grant payment | | | X | | payment per site | 1,850 | 115 | 213,590 | | | | | | | |
| 1.2.1.10 Vender payments | | | X | | vendor | 4 | 22,546 | 90,184 | | | | | | | |
| 1.2.1.11 other | | X | | | | | | | | | | | | | |
| 1.2.2 Task List (Wkly Updates) | | X | | | | | | | | | | | | | |
| 1.2.3 Issues/Decision Log (Wkly Updates) | | X | | | | | | | | | | | | | |
| 1.2.4 CTI/ CRO Meeting Telecon. Agenda; Minutes (wkly) | | X | | | week | 143 | 2,445 | 349,565 | | | teleconference | 143 | 150 | 21,450 | |
| 1.2.5 Weekly Monitoring Team Meetings | | X | | | week | 143 | 5,588 | 799,142 | | | | | | | |
| 1.2.6 Frequently Asked Questions for sites (Wkly) | | X | | | | | | | | | | | | | |

Figure 13-F

| Task | | | | | | | | | | | | |
|---|---|---|---|---|---|---|---|---|---|---|---|---|
| 1.2.7 Study News Letter- (Mo/Qtr) (CRF completion updates; Protocol Clarifications; Freq Asked Questions; AE coding help) | | x | newsletter | 30 | 3,029 | 90,855 | | | | | | |
| 1.3 Training | x | x | | | | 172,488 | | | | | 26,963 | |
| 1.3.1 Project Familization | | x | meeting | 1 | 30,940 | 30,940 | | | | | | |
| 1.3.2 CRO Kick Off Mtg | x | x | meeting | 1 | 34,216 | 34,216 | | meeting | 1 | 5,947 | 5,947 | |
| 1.3.3 CTI/CRO Face to Face | | x | meeting | 5 | 21,466 | 107,332 | | meeting | 5 | 4,203 | 21,017 | |
| 1.4 Recruitment Plan | x | | | | | | | | | | | |
| 2 Medical Management | x | x | | | | | 646,621 | | | | | |
| 2.1 Medical Monitoring/ PV | x | x | | | | | 646,621 | | | | | |
| 2.1.1 Medical Monitor | x | | | | | | | | | | | |
| 2.1.2 SAE Initial &Follow-up Reports | | x | SAE | 300 | 1,187 | 356,029 | | | | | | |
| 2.1.3 SAE Narrative as part of SAE Rpt | x | | | | | | | | | | | |
| 2.1.4 24 hr Med non SAE coverage | x | | | | | | | | | | | |
| 2.1.5 Reportable Determination | x | | | | | | | | | | | |
| 2.1.6 CRF or Table/Listing Safety | x | | | | | | | | | | | |
| 2.1.7 Generation of IND / CIOMOS safety letter | | x | letter | 30 | 8,189 | 245,661 | | | | | | |
| 2.1.8 Site Safety Report Submission | x | | | | | | | | | | | |
| 2.1.9 Develop and maintain safety database | | | | | | | | | | | | |
| 2.1.10 Reconcile safety database with AE data base | | x | SAE | 300 | 150 | 44,931 | | | | | | |
| 2.1.11 Distribute SAE and safety updates per GCP to sites | x | | | | | | | | | | | |
| 2.1.12 DMC management/safety updates | x | | | | | | | | | | | |
| 2.2 Quality Plan | x | | | | | | | | | | | |
| 2.2.1 Vendor Audits | x | | | | | | | | | | | |
| 2.2.2 Site Audits | x | | | | | | | | | | | |
| 2.3 Records Archiving & Management | x | | | | | | | | | | | |
| 3 Vendor Administration | x | | | | | | | | | | | |
| 3.1 Drug packaging facility payment | x | | | | | | | | | | | |
| 3.2 Central laboratory payments | x | | | | | | | | | | | |
| 3.3 Assessment Payments | x | | | | | | | | | | | |
| 3.4 Central Reader Payment | x | | | | | | | | | | | |

Figure 13-G

| DESCRIPTION | RESPONSIBILITIES | | | | ESTIMATED DIRECT COSTS | | | | | | | ESTIMATED PASSTHROUGH COSTS | | | |
|---|---|---|---|---|---|---|---|---|---|---|---|---|---|---|---|
| | Sponsor | VENDER | Joint | n/a | Unit Type | ITEM TOTAL | | | SECTION SUB TOTAL | Unit Type | ITEM TOTAL | | | SECTION SUB TOTAL |
| | | | | | | Unit | Price per Unit | Item Total | | | Unit | Price per Unit | Item Total | |
| 4 Study Start Up | X | X | X | X | | | | | 1,313,227 | | | | | 233,937 |
| 4.1 Investigator Brochure/ Pharmacy Brochure | | X | | | | | | | 47,045 | | | | | |
| 4.1.1 Draft or update IB | X | | | | | | | | | | | | | |
| 4.1.2 Review and Approve | X | | | | | | | | | | | | | |
| 4.1.3 Distribute to Sites; IRB/IEC | | X | | | site | 185 | 254 | 47,045 | | | | | | |
| 4.2 Protocol development | X | X | | | | | | | 18,656 | | | | | 18,467 |
| 4.2.1 Literature review, background research | X | | | | | | | | | | | | | |
| 4.2.2 Design and write protocol | X | | | | | | | | | | | | | |
| 4.2.3 Review Protocol | X | | | | protocol | 1 | 6,092 | 6,092 | | | | | | |
| 4.2.4 Approve protocol | X | | | | | | | | | | | | | |
| Direct Cost | | X | | | | | | | | | | | | |
| 4.2.6 Translate Protocol | | X | | | translation | 5 | 2,513 | 12,564 | | translation | 5 | 3,693 | 18,467 | |
| 4.2.7 Copy & Distribute Protocol to sites | | X | | | | | | | | | | | | |
| 4.2.8 Protocol Amendments | X | | | | | | | | | | | | | |
| 4.3 Informed Consent Development | X | X | | | | | | | 6,756 | | | | | |
| 4.3.1 Draft Informed Consent Template | X | | | | unit | 1 | 6,756 | 6,756 | | | | | | |
| 4.3.2 IC Template review and approval | | | X | | | | | | | | | | | |
| 4.3.3 IC Translation | | X | | | | | | | | | | | | |

Figure 13-H

| | | | | | | | | | | |
|---|---|---|---|---|---|---|---|---|---|---|
| 4.4 CRF (see also DM) | x | | | | | | | | | |
| 4.4.1 Approve CRFs and patient assessment booklets | | x | | | | | | | | |
| 4.4.2 CRF completion conventions | | | x | | | | | | | |
| 4.5 Regulatory Submissions | | | x | | | | | 141,927 | | |
| 4.5.1 Manage regulatory submissions (based on FDA IND docs) | | | x | site | 185 | 2,531 | 468,179 | | | |
| 4.5.2 Manage regulatory updates | | | x | site | 185 | 495 | 91,521 | | | |
| 4.6 Investigator recruitment and Selection | x | ##### | | | | | 452,704 | | | |
| 4.6.1 Develop list of potential investigators | | x | | site | 185 | 452 | 83,702 | | | |
| 4.6.2 Qualification Telephone surveys | | | x | site | 185 | 606 | 112,028 | | | |
| 4.6.3 Pre-study Qualification Visits | | | x | | | | | | | |
| 4.6.3.1 Conduct site qualification visits | | | x | site | 40 | 1,477 | 59,073 | | | |
| 4.6.3.2 Provide written site evaluation report | | | x | site | 40 | 607 | 24,276 | visit | 40 | 687 | 27,480 |
| 4.6.4 Select sites | | | x | | | | | | | |
| 4.6.5 Prepare Investigator contract | x | | | | | | | | | |
| 4.6.6 Negotiate Investigator grants (site budgets) | x | | | | | | | | | |
| 4.6.7 Collect essential and reg documents | | | x | site | 185 | 939 | 173,625 | | | |

Figure 13-I

| | | | | | | | | | | | | | | |
|---|---|---|---|---|---|---|---|---|---|---|---|---|---|---|
| 4.8 Drug Supply | X | | | | | | | | | | | | | |
| 4.8.1 Arrange drug packaging | | X | | | | | | | | | | | | |
| 4.8.2 Arrange drug labeling | | | X | | | | | | | | | | | |
| 4.8.3 Drug storage and distribution | | | | X | | | | | | | | | | |
| 4.9 Patient randomization (IVRS?) (See Biostats) | | | | | X | 1 | 2,364 | 2,364 | | | | | | |
| 4.1 IRB/IEC | | | | | X | | | | | | | | | |
| 4.10.1 Select Central IRB | | | | | | X | | | | | | | | |
| 4.10.2 Manage Ethics Committee/IRBs submissinos | | | | | X | | | | | | | | | |
| 4.10.3 Managage Regulatory Submissions | | | | | X | | | | | | | | | |
| 4.11 Pk Assessments | | | | | X | | | | | | | | | |
| 4.11.1 Identify Labs, NDA, RFP | | | | | X | | | | | | | | | |
| 4.11.2 Vendor Audits | | | | | X | | | | | | | | | |
| 4.11.3 Develop/Transfer procedures | | | | | X | | | | | | | | | |
| 4.11.4 Per patient cost of Sample kits | | | | | X | | | | | | | | | |
| 4.11.5 Shipping, testing, and storage procedures | | | | | X | | | | | | | | | |
| 4.11.6 Sample archiving | | | | | X | | | | | | | | | |
| 4.11.7 Electronic Data Collection | | | | | X | | | | | | | | | |
| 4.11.8 Data Transfer | | | | | X | | | | | | | | | |
| 4.12 Central laboratory | | | | | X | | | 23,621 | | | | | | |
| 4.12.1 Identify Labs, NDA, RFP | | | | | X | | | | | | | | | |
| 4.12.2 Vendor Audits | | | | | | | | | | | | | | |
| 4.12.3 Per patient cost of Sample kits | | | | | X | | | | | | | | | |

Figure 13-J

| | | | | | | | | | |
|---|---|---|---|---|---|---|---|---|---|
| 4.12.4 Per patient cost of lab tests | | x | | | | | | | |
| 4.12.5 Sample archiving | | | x | | | | | | |
| 4.12.6 Electronic Data Collection | | | x | | timpoints | 6,300 | 4 | 23,621 | | |
| 4.12.7 Data Transfer | | | x | | | | | | | |
| 4.13 Site Study Binders | | | x | | | | | | | |
| 4.13.1 Site Regulatory Binder | | | x | | | | | | binder | 185 | 26 | 4,884 |
| 4.13.2 Site Study Binder | | | x | | | | | | binder | 185 | 26 | 4,884 |
| 4.13.3 Site Pharmacy Binder | | | x | | | | | | | |
| 4.13.4 Site pK Binder | | | | | | | | | | |
| 4.15 Recruit independent Data Monitoring committee | | | | x | | | | | | |
| 4.14 Investigator's meeting | | | x | | | | | 202,382 | | | | 36,294 |
| 4.14.1 Location | x | | | | | | | | | |
| 4.14.2 Agenda | x | | | x | | | | | | |
| 4.14.3 Attendee list | | | | x | | | | | | |
| 4.14.4 Travel arrangements | | | x | | | | | | | |
| 4.14.5 Run meeting | | | x | | | | | | | |
| 4.14.6 Presentations | | | x | | | | | | | |
| 4.14.7 Meeting materials/Bindes | | | x | | | 2 | 12,775 | 25,550 | | | |
| 4.14.8 Attendance | x | | x | | | | | | | |
| | | | | | | 2 | 88,416 | 176,832 | | 2 | 18,147 | 36,294 |

Figure 13-K

| DESCRIPTION | RESPONSIBILITIES | | | | ESTIMATED DIRECT COSTS | | | | ESTIMATED PASSTHROUGH COSTS | | | | |
| --- | --- | --- | --- | --- | --- | --- | --- | --- | --- | --- | --- | --- | --- |
| | Sponsor | VENDER | Joint | n/a | Unit Type | ITEM TOTAL | | | SECTION SUB TOTAL | Unit Type | ITEM TOTAL | | SECTION SUB TOTAL |
| | | | | | | Unit | Price per Unit | Item Total | | | Unit | Price per Unit | Item Total |
| 8 Drug Supply Management | X | X | X | | | | | | 53256 | | | | |
| 8.1 Drug Supply Plan | X | X | X | | | | | | 53256 | | | | |
| 8.1.1 Drug Supply | X | | | | | | | | | | | | |
| 8.1.2 Packaging | X | | | | | | | | | | | | |
| 8.1.3 Inventory Management | X | | | | | | | | | | | | |
| 8.1.4 Randomization? | X | | | | | | | | | | | | |
| 8.1.5 Pt level lot tracking | X | | | | | | | | | | | | |
| 8.1.6 Distributor management | X | | | | | | | | | | | | |
| 8.1.7 Country Specific Labels | X | | | | | | | | | | | | |
| 8.1.8 Import licenses | | X | | | license | 7 | 602 | 4,214 | | | | | |
| Direct Cost | X | | | | | | | | | | | | |
| 8.1.10 Country Depots | X | | | | | | | | | | | | |
| 8.1.8 Within Country Compartor Procurement | X | | | | | | | | | | | | |
| 8.1.12 Shipping requirements (Hazardous?) | X | | | | | | | | | | | | |
| 8.1.13 Shipper | X | | | | | | | | | | | | |

Figure 13-L

| | | | | | 185 | 265 | 49,042 | | | | | | |
|---|---|---|---|---|---|---|---|---|---|---|---|---|---|
| 8.1.14 Drug Distruction | | | | | | | | | | | | | |
| 8.1.15 Final Reconciliation | | | | x | | | | | | | | | |
| | | | | x | | | | | | | | | |
| 8.1.16 Ancillary Supplies | x | | | | | | | | | | | | |
| 8.2 Supply Study Drug for packaging | x | x | | | | | | | | | | | |
| 8.2.1 Identify vendors for compators | x | | | | | | | | | | | | |
| 8.2.2 Import Licenses and Customs Clearance | | x | | | | | | | | | | | |
| 8.3 Package Study Drug | x | | | | | | | | | | | | |
| 8.4 Produce Randomization Code | x | | | | | | | | | | | | |
| 8.5 Label study drug | x | | | | | | | | | | | | |
| 8.6 Ship study drug to site | x | | | | | | | | | | | | |
| 8.7 Store study drug | | | x | | | | | | | | | | |
| 8.8 study drug accountability | | | x | | | | | | | | | | |
| 8.9 Perform post-study drug accountability | | | | x | | | | | | | | | |
| 12 Study drug disposition & accountability | | | | x | | | | | | | | | |

Figure 13-M

| DESCRIPTION | RESPONSIBILITIES | | | | ESTIMATED DIRECT COSTS | | | | | ESTIMATED PASSTHROUGH COSTS | | | | |
|---|---|---|---|---|---|---|---|---|---|---|---|---|---|---|
| | Sponsor | VENDER | Joint | n/a | Unit Type | ITEM TOTAL | | | SECTION SUB TOTAL | Unit Type | ITEM TOTAL | | | SECTION SUB TOTAL |
| | | | | | | Unit | Price per Unit | Item Total | | | Unit | Price per Unit | Item Total | |
| 9 Labs and Assessments | | | | | | | | | | | | | | |
| 9.1 Central lab | | | X | X | | | | | | | | | | |
| 9.1.1 per patient sampling kit cost | | | X | | | | | | | | | | | |
| 9.1.2 per patient testing cost | | | X | | | | | | | | | | | |
| 9.1.3 per patient shiping est. | | | X | | | | | | | | | | | |
| 9.1 pK Lab | | | | X | | | | | | | | | | |
| 9.1.1 Test Validation Charges | | | | | | | | | | | | | | |
| 9.1.2 per patient sampling kit cost | | | | | | | | | | | | | | |
| 9.1.3 per patient testing cost | | | | | | | | | | | | | | |
| 9.1.4 per patient shiping est. | | | | | | | | | | | | | | |
| Direct Cost | | | | | | | | | | | | | | |
| 9.2 Central Readers | | | | | | | | | | | | | | |

Figure 13-N

| DESCRIPTION | RESPONSIBILITIES | | | | ESTIMATED DIRECT COSTS | | | | | | ESTIMATED PASSTHROUGH COSTS | | | | |
|---|---|---|---|---|---|---|---|---|---|---|---|---|---|---|---|
| | Sponsor | VENDER | Joint | n/a | Unit Type | ITEM TOTAL | | | SECTION SUB TOTAL | | ITEM TOTAL | | | SECTION SUB TOTAL |
| | | | | | | Unit | Price per Unit | Item Total | | Unit Type | Unit | Price per Unit | Item Total | |
| 6 Data Management | X | X | X | | | | | | 929,443 | | | | | |
| 6.1 Data Project Management | | | | | | | | | | | | | | |
| 6.2 Develop Data Management and Quality Plan | X | X | | | plan | 1 | 18,181 | 18,181 | 18,181 | | | | | |
| 6.2.1 Collaborate, review, and approve DM and DQ Plan | | | | | | | | | | | | | | |
| 6.3 Status Reports CRFs; Data Entry, Queries | | X | | | page | 35,700 | 11 | 402,885 | 402,885 | | | | | |
| 6.4 Client Conference Calls | | | X | | | | | | | | | | | |
| 6.5 CRFs | | | X | | | | | | 30,949 | | | | | 96,762 |
| CRFs/Paper or Electronic | | | | | | | | | | | | | | |
| 6.5.1.1 Provide Draft CRFs | | | | | | | | | | | | | | |
| 6.5.1.2 Design CRFs | | | | | page | 119 | 215 | 25,611 | | | | | | |
| Direct Cost | | | | | | | | | | | | | | |
| 6.5.1.4 Approve CRFs | | | | | | | | | | | | | | |
| 6.5.2 Print CRFs | | | | | patient | 300 | 18 | 5,339 | | patient | 300 | 323 | 96,762 | |
| 6.5.3 Distribute CRFs to sites | | | | | | | | | | | | | | |
| 6.5.4 Electronic CRF | | X | | | | | | | | | | | | |
| 6.5.4.1 Server/Datase Configuration & Qualification | | X | | | | | | | | | | | | |
| 6.5.4.2 eCRF Design | | X | | | | | | | | | | | | |
| 6.5.4.3 eCRF Programming | | X | | | | | | | | | | | | |
| 6.5.4.4 eCRF QC | | X | | | | | | | | | | | | |
| 6.5.4.5 eCFR Approval | X | | | | | | | | | | | | | |
| 6.5.4.6 eCRF Deployment | | X | | | | | | | | | | | | |
| 6.5.4.7 eCRF Completion conventions | | | X | | | | | | | | | | | |
| 6.6 Data Base Administration | X | X | X | | | | | | 153,214 | | | | | |

Figure 13-O

| Task | | | | | | | Unit | | | | |
|---|---|---|---|---|---|---|---|---|---|---|---|
| 6.6.1 Data Base Specification | | X | | | | | | | | | |
| 6.6.2 Data Base Design | | X | | | | | database | 1 | 107,163 | 107,163 | |
| 6.6.3 Approve DB Design | X | | | | | | | | | | |
| 6.6.4 Data Base QC | | | X | | | | QC | 2 | 16,291 | 32,583 | |
| 6.6.5 Data Base Audit | | | X | | | | | | | | |
| 6.6.6 Data Base Documentation | | X | | | | | listing | 30 | 449 | 13,468 | |
| 6.7 Edit Checks | | X | | | | | | | | | |
| 6.7.1 Edit Check Specifications | | X | | | | | | | | | |
| 6.7.2 Edit Check Programing | | X | | | | | | | | | |
| 6.7.3 Edit Check QC | X | | X | | | | page | 35,700 | 1 | 42,896 | 42,896 |
| 6.8 Self-Evident Edit Checks | | | | | | | | | | 131,077 | 131,077 |
| 6.9 Data Entry | | X | | | | | | | | | |
| 6.9.1 eCRF at Site | | X | | | | | page | 35,700 | 4 | 131,077 | |
| 6.9.2 paper - Double Data entry | | | | X | | | | | | | |
| 6.1 Dictionary Coding | | | | X | | | patient | 300 | 204 | 61,243 | 61,243 |
| 6.10.1 SAE Coding | | | | X | | | | | | | |
| 6.10.2 Mediation Coding | | | X | | | | | | | | |
| 6.11 CRF storage or imaging | | X | | | | | | | | | |
| 6.12 Central Laboratory Data intergration | | | | X | | | | | | | |
| 6.12.1 Lab Normal Ranges | | X | | | | | | | | | |
| 6.13 Central Scan or X-ray data | | X | | | | | | | | | |
| 6.14 pK or -Special Assessment Data | | X | | | | | | | | | |
| 6.15 Query Generation and Query Management | X | | X | | | | | | | 21,632 | 21,632 |

Figure 13-P

| | | | | | | | | | | |
|---|---|---|---|---|---|---|---|---|---|---|
| 6.15.1 Site generated Queries | X | | | | | | | | | |
| 6.15.2 CRA Generated Queries | | X | | | | | | | | |
| 6.15.3 Listing Review generated Queries | | | X | | | | | | | |
| 6.15.4 Central Reads generated queries | | | | | | | | | | |
| 6.15.5 SAE - AE reconciliation | X | | | SAE | 300 | 72 | 21,632 | | | |
| 6.16 Monthly Transfer SAS datafiles | X | | | transfer | 19 | 770 | 14,630 | 14,630 | | |
| 6.17 Track CRF, Queries, patients | X | | | page | 35,700 | 1 | 52,735 | 52,735 | | |
| 6.18 Database Maintenance, Hosting and Support | X | | | | | | | | | |

Figure 13-Q

| DESCRIPTION | RESPONSIBILITIES | | | ESTIMATED DIRECT COSTS | | | | | ESTIMATED PASSTHROUGH COSTS | | | | |
|---|---|---|---|---|---|---|---|---|---|---|---|---|---|
| | Sponsor | Vendor | Joint | n/a | Unit Type | ITEM TOTAL | | | SECTION SUB TOTAL | Unit Type | ITEM TOTAL | | SECTION SUB TOTAL |
| | | | | | | Unit | Price per Unit | Item Total | | | Unit | Price per Unit | Item Total | |
| 5 Initiation and Monitoring | X | X | | | | | | | 14,276,001 | | | | | 2,663,310 |
| 5.1 Initiation | | X | | | | | | | 513,625 | | | | 116,393 | 116,393 |
| 5.1.1 Prestudy Documentation | | X | | | site | 185 | 2,019 | 373,590 | | | | | | |
| 5.1.3 Complete initiation visit report | | X | | | site | 185 | 757 | 140,035 | | | | | | |
| 5.2 Interim Monitoring | | X | | | | | | | 10,488,089 | | | | 2,327,864 | 2,327,864 |
| 5.2.1 Conduct monitoring visits | | X | | | visit | 3,700 | 2,019 | 7,471,800 | | visit | 3,700 | 629 | 2,327,864 | |
| 5.2.2 Verify 100% of source documentation | | X | | | | | | | | | | | | |
| 5.2.3 Resolve edits/queries with site | | X | | | site | 185 | 375 | 69,432 | | | | | | |
| 5.2.4 Review drug records | | X | | | site | 185 | 790 | 146,158 | | | | | | |
| 5.2.5 Review lab storage | | X | | | | | | | | | | | | |
| Direct Cost | | X | | | | | | | | | | | | |
| 5.2.7 Interim Monitoring Visit report | | X | | | visit | 3,700 | 757 | 2,800,700 | | | | | | |
| 5.2.8 Complete interim monitoring report | | X | | | | | | | | | | | | |
| 5.3 Site Close-Out | X | X | | | | | | | 1,324,624 | | 185 | 629 | 116,393 | 116,393 |

Figure 13-R

| | | | | | site | 185 | 2,019 | 373,590 | visit | 185 | 629 | 116,393 |
|---|---|---|---|---|---|---|---|---|---|---|---|---|
| 5.3.1 Conduct site close-out visits | | x | | | | | | | | | | |
| 5.3.2 Site files complete; records archive | x | | | | month | 33 | 23,996 | 796,996 | | | | |
| 5.3.3 data queries resolved | | x | | | | | | | | | | |
| 5.3.4 sample archival discussed | | x | | | | | | | | | | |
| 5.3.5 drug reconciled | | x | | | | | | | | | | |
| 5.3.6 Survival | | x | | | | | | | | | | |
| 5.3.7 Provide close-out trip report | | x | | | site | 185 | 833 | 154,039 | | | | |
| 5.4 Site General Administration | | x | | | | | | 1,949,663 | month | 33 | 3,091 | 102,659 |
| 5.4.1 Weekly telephone contact with sites | | x | | | week | 130 | 14,966 | 1,949,663 | | | 102,659 | |
| 5.4.2 Brief In-person site contact | | x | | | | | | | | | | |
| 5.4.3 Investigator /institution grant administration | | x | | | | | | | | | | |
| 5.4.4 Provide newsletters | | x | | | | | | | | | | |
| 5.4.5 Provide helpdesk for study conduct (unrelated to eCRF) | | x | | | | | | | | | | |

Figure 13-S

| DESCRIPTION | RESPONSIBILITIES ||| | ESTIMATED DIRECT COSTS |||| | ESTIMATED PASSTHROUGH COSTS |||
|---|---|---|---|---|---|---|---|---|---|---|---|---|
| | Sponsor | VENDER | Joint | n/a | Unit Type | Unit | Price per Unit | Item Total | SECTION SUB TOTAL | Unit Type | Unit | Price per Unit | Item Total | SECTION SUB TOTAL |
| 7 Statistical Analysis | X | | | | | | | | | | | | | |
| 7.1 Statistical Analysis Plan | X | | | | | | | | | | | | | |
| 7.1.1 Develop Analysis Plan | | X | | | | | | | | | | | | |
| 7.1.2 Review and Approve SAP | | | X | | | | | | | | | | | |
| 7.1.3 Number of tables (unique/total) | X | | | | | | | | | | | | | |
| 7.1.4 Number of Listings (unique/total) | | X | | | | | | | | | | | | |
| 7.1.5 Number of figures (unique/total) | X | | | | | | | | | | | | | |
| 7.2 Randomization Plan (IVRS?) | X | | | | | | | | | | | | | |
| 7.3 Data Monitoring Committee | X | | | | | | | | | | | | | |
| 7.4 Table,Listing, and figure Programing | X | | | | | | | | | | | | | |
| Direct Cost | X | | | | | | | | | | | | | |
| 7.7 Query Generation | X | | | | | | | | | | | | | |
| 7.7 Interm Analysis | X | | | | | | | | | | | | | |
| 7.8 Draft T/L/F | X | | | | | | | | | | | | | |
| 7.9 Blinded/ Mock T/L/F | X | | | | | | | | | | | | | |

Figure 13-T

| PROPOSED STUDY TARGET DATES | |
|---|---|
| Study Start Date | Q1-Q2 2007 |
| Site Initiation (study set up 4 months) | March 2007 for site selection start |
| Enrollment Period: | March/April 2007-December 2008 (18-24 months) |
| | |
| First Patient In | March/April 2007 (token USA pt) |
| Last Patient In | March 2009 |
| Treatment Period: | up to 6 cycles |
| Last Patient Out | Sept 2009 |
| Follow-up Period: | ~6 months |
| Survival Follow up | SAA |
| Interim Analysis | yes |
| Last CRF in | TBD |
| Clean Database Lock | Sept/Oct 2009 |
| Statistical Analysis | TBD |
| Clinical Study Report | Q4-2009 |
| | |
| | |

Figure 13-U

| PROJECT OVERVIEW | | |
|---|---|---|
| | Compound Name | Xyotax |
| | Program Phase | Phase III |
| | Dosage Form | IV |
| | Indication | NSCLC, E+ female only |
| | Study Design | Randomized, Comparative |
| | Patient Population | • Locally advanced or recurrent disease previously treated with radiation and/or surgery, or stage IIIB or IV |
| | Number of Patients | 300 total |
| | World Regions (US; EU; ** May need to greatly increase number of sites in these countries. These are the only countries we will consider) | Spain, France, Belgium, Germany, USA, Canada, Australia, Czech, UK, |
| | Number of Investigators | 150-180 |
| | Approximate Number of Patients Per Site | 1-2 subjects/site |
| | Enrolment Rate | .5-1 patient per site every month |
| | Duration of Patient Participation | upto 6 cycles plus follow up period ~1 year |
| | -Screening/Run-In | <28 days |
| | - # of cycles | 6 |
| | -Follow-Up | 6 months |
| | -Survival Follow-Up | SAA |
| | Number of Protocol Summary Translations | French, Italian, Spanish, German, Danish, 3-5 Eastern Europe Translations, Mexico. |
| | Number of Full Protocol Translations | SAA |
| | Number of Informed Consent Translations | SAA |
| | Number of Investigators' Meetings | 1 per region |
| | Number of Protocol Amendments | 2 |

Figure 13-V

| Clincal Information | | |
|---|---|---|
| | Total Number of Monitoring Visits | Monitoring frequency every 6-8 weeks. |
| | -Potential sites Identified | |
| | -Pre-Study Evaluation (<1.2 X # ctrs) | 40 |
| | -Initiation (1 X # ctrs) | 150 |
| | -Interim Monitoring (IM) | every 6-8 weeks |
| | - IM Freq (enrollment) | within 3 weeks of FPI or sooner |
| | - IM Freq (treatment) | every 6-8 weeks |
| | - IM Freq (followup) | 2-3 months |
| | Number of Co-Monitoring Visits | 20 |
| | -Close-Out | 150 |
| | Total Number of Monitoring & close out Visits | |
| | Duration of Monitoring Visits (Hours) | 6 hours |
| | -Initiation | 24 (including travel/prep time) |
| | -Interim | 24 (including travel/prep time) |
| | -Close-Out | 24 (including travel/prep time) |
| | | |
| Project Management | | |
| | Number of COMPANY/CRO Project Team Meetings | Quarterly meetings |
| | Number of internal face-to-face CRO Project Team Meetings (1 kick-off meeting) | 6 |
| | COMPANY/CRO Project Team Teleconferences | Weekly |
| | Internal CRO project team teleconferences | TBD |
| Central Lab / Readers/ Special Assessments | | |
| | Central lab (Estrogen, LDH) | All labs |
| | | |
| | Local Labs: | Chem/cbc |

Figure 13-W

| Data Management | | |
|---|---|---|
| | # of Unique CRF Pages | 33 |
| | # of CRF Pages/ Completed Patient | 209 |
| | # of CRF Pages/ Screen Failure Patients | None |
| | Will Screen Fail CRFs Be Processed (yes/no) | None |
| | # of CRF Pages/ Early Withdrawal | $23+(16xC)$, C=# of cycles |
| | Total # of CRFs to be Processed by Data Management | |
| | # of Queries/ Patient | 20 |
| | # of Manually Coded Items/ Patient | None |
| | # of Other Electronic Data Sources | One, central lab |
| | Data Transfers: | |
| | # of Cumulative Dirty DB Transfers | Twelve |
| | # of Cumulative Clean DB Transfers | Six |
| | # of Incrementally Clean DB Transfers | None |
| | Interim Analysis | |
| | # of Interim Analyses | 1 |
| | # of Interim Analyses to Support Planned Interim Analyses | 1 |
| | | |
| | Will there be an SAE Reconciliation to the Clinical Database (yes/no) | yes |
| | DSMC (yes/no) | no |
| | # of Times DSMC will Meet | |
| | Annual IND Filing (yes/no) | yes |

Figure 13-X

| DESCRIPTION | RESPONSIBILITIES ||||  ESTIMATED DIRECT COSTS |||||  ESTIMATED PASS-THROUGH COSTS |||||
|---|---|---|---|---|---|---|---|---|---|---|---|---|---|
| | Sponsor | VENDER | Joint | n/a | Unit Type | # Units | Price per Unit | Item Total | SECTION SUB TOTAL | Unit Type | # Units | Price per Unit | Item Total | SECTION SUB TOTAL |
| 1 Project Management | X | X | X | | | | | | 7,031,845 | | | | | 144,399 |
| 1.1 Time Line Management | X | X | X | | month | 33 | 127,618 | 4,238,601 | 4,238,601 | month | 33 | 2,773 | 92,085 | 92,085 |
| 1.2 Team Management | X | X | X | | | | | | 2,619,546 | | | | | 25,350 |
| 1.2.1 Status Reports | | X | | | week | 133 | 1,459 | 194,113 | | | | | | |
| 1.2.1.1 Essential Doc. Version Tracking (approved. Prot; ICF; CRF; IB) | X | | | | | | | | | | | | | |
| 1.2.1.2 Initiation (Ess. Doc tracking by country and site) | | X | | | | | | | | | | | | |
| 1.2.1.3 Pt Recruitment | X | X | | | | | | | | | | | | |
| 1.2.1.4 Monitoring (Visits and reports) | | X | | | report | 3,499 | 171 | 599,699 | | | | | | |
| 1.2.1.5 CRF retrieval | | X | | | | | | | | | | | | |
| 1.2.1.6 Queries (rate; closed; pending) | | X | | | | | | | | | | | | |
| Direct Cost | | X | | | | | | | | | | | | |
| 1.2.1.8 SAE | | X | | | | | | | | | | | | |
| 1.2.1.9 Invest Grant payment | | | X | | payment per site | 2,220 | 116 | 258,333 | | | | | | |
| 1.2.1.10 Vender payments | | | X | | vendor | 4 | 22,750 | 91,001 | | | | | | |
| 1.2.1.11 other | | X | | | | | | | | | | | | |
| 1.2.2 Task List (Wkly Updates) | | X | | | | | | | | | | | | |
| 1.2.3 Issues/Decision Log (Wkly Updates) | | X | | | | | | | | | | | | |
| 1.2.4 CTI/ CRO Meeting Telecon. Agenda; Minutes (wkly) | | X | | | week | 143 | 2,906 | 415,566 | | teleconference | 143 | 177 | 25,350 | |
| 1.2.5 Weekly Monitoring Team Meetings | | X | | | week | 143 | 6,649 | 950,854 | | | | | | |
| 1.2.6 Frequently Asked Questions for sites (Wkly) | | X | | | | | | | | | | | | |
| 1.2.7 Study News Letter- (Mo/Qtr) (CRF completion updates; Protocol Clarifications; Freq Asked Questions; AE coding help) | | X | | | newsletter | 36 | 3,055 | 109,980 | | | | | | |

Figure 13-Y

| | | | | | | | | |
|---|---|---|---|---|---|---|---|---|
| 1.3 Training | | X | | | 173,698 | | | | 26,963 |
| 1.3.1 Project Familization | | X | meeting | 1 | 31,180 | 31,180 | | | |
| 1.3.2 CRO Kick Off Mtg | | X | meeting | 1 | 34,460 | 34,460 | meeting | 1 | 5,947 | 5,947 |
| 1.3.3 CTI/CRO Face to Face | | X | meeting | 5 | 21,612 | 108,058 | meeting | 5 | 4,203 | 21,017 |
| 1.4 Recruitment Plan | X | | | | | | | | |
| 2 Medical Management | X | X | | | | 651,482 | | | |
| 2.1 Medical Monitoring/ PV | X | X | | | | 651,482 | | | |
| 2.1.1 Medical Monitor | X | | | | | | | | |
| 2.1.2 SAE Initial &Follow-up Reports | X | | SAE | 300 | 1,195 | 358,517 | | | |
| 2.1.3 SAE Narrative as part of SAE Rpt | X | | | | | | | | |
| 2.1.4 24 hr Med non SAE coverage | X | | | | | | | | |
| 2.1.5 Reportable Determination | X | | | | | | | | |
| 2.1.6 CRF or Table/Listing Safety | X | | | | | | | | |
| 2.1.7 Generation of IND / CIOMOS safety letter | X | | letter | 30 | 8,258 | 247,734 | | | |
| 2.1.8 Site Safety Report Submission | X | | | | | | | | |
| 2.1.9 Develop and maintain safety database | X | | | | | | | | |
| 2.1.10 Reconcile safety database with AE data base | X | | SAE | 300 | 151 | 45,231 | | | |
| 2.1.11 Distribute SAE and safety updates per GCP to sites | X | | | | | | | | |
| 2.1.12 DMC management/safety updates | X | | | | | | | | |
| 2.2 Quality Plan | X | | | | | | | | |
| 2.2.1 Vendor Audits | X | | | | | | | | |
| 2.2.2 Site Audits | X | | | | | | | | |
| 2.3 Records Archiving & Management | X | | | | | | | | |
| 3 Vendor Administration | X | | | | | | | | |
| 3.1 Drug packaging facility payment | X | | | | | | | | |
| 3.2 Central laboratory payments | X | | | | | | | | |
| 3.3 Assessment Payments | X | | | | | | | | |
| 3.4 Central Reader Payment | X | | | | | | | | |

Figure 13-Z

| DESCRIPTION | RESPONSIBILITIES | | | | ESTIMATED DIRECT COSTS | | | | | ESTIMATED PASSTHROUGH COSTS | | | | |
|---|---|---|---|---|---|---|---|---|---|---|---|---|---|---|
| | Sponsor | VENDER | Joint | n/a | Unit Type | Unit | ITEM TOTAL Price per Unit | ITEM TOTAL Item Total | SECTION SUB TOTAL | Unit Type | Unit | ITEM TOTAL Price per Unit | ITEM TOTAL Item Total | SECTION SUB TOTAL |
| 4 Study Start Up | X | X | X | X | | | | | 1,326,730 | | | | | 233,937 |
| 4.1 Investigator Brochure/ Pharmacy Brochure | | X | | | | | | | 47,431 | | | | | |
| 4.1.1 Draft or update IB | X | | | | | | | | | | | | | |
| 4.1.2 Review and Approve | X | | | | | | | | | | | | | |
| 4.1.3 Distribute to Sites; IRB/IEC | | X | | | site | 185 | 256 | 47,431 | | | | | | |
| 4.2 Protocol development | X | X | | | | | | | 18,794 | | | | | 18,467 |
| 4.2.1 Literature review, background research | X | | | | | | | | | | | | | |
| 4.2.2 Design and write protocol | X | | | | | | | | | | | | | |
| 4.2.3 Review Protocol | X | X | | | protocol | 1 | 6,142 | 6,142 | | | | | | |
| 4.2.4 Approve protocol | X | X | | | | | | | | | | | | |
| Direct Cost | | X | | | | | | | | | | | | |
| 4.2.6 Translate Protocol | | X | | | translation | 5 | 2,530 | 12,652 | | translation | 5 | 3,693 | 18,467 | |
| 4.2.7 Copy & Distribute Protocol to sites | | X | | | | | | | | | | | | |
| 4.2.8 Protocol Amendments | X | | | | | | | | | | | | | |
| 4.3 Informed Consent Development | X | X | X | | unit | 1 | 6,803 | 6,803 | 6,803 | | | | | |
| 4.3.1 Draft Informed Consent Template | X | | | | | | | | | | | | | |
| 4.3.2 IC Template review and approval | | | X | | | | | | | | | | | |
| 4.3.3 IC Translation | | X | | | | | | | | | | | | |

Figure 13-AA

| Task | | | | | Unit | | | | | Unit | | | | |
|---|---|---|---|---|---|---|---|---|---|---|---|---|---|---|
| 4.4 CRF (see also DM) | X | | | | | | | | | | | | | |
| 4.4.1 Approve CRFs and patient assessment booklets | | X | | | | | | | | | | | | |
| 4.4.2 CRF completion conventions | | | X | | | | | | | | | | | |
| 4.5 Regulatory Submissions | | X | | | | | | | 567,365 | site | 185 | 767 | 141,927 | 141,927 |
| 4.5.1 Manage regulatory submissions (based on FDA IND docs) | | X | | | site | 185 | 2,548 | 471,455 | | | | | | |
| 4.5.2 Manage regulatory updates | | X | | | site | 185 | 518 | 95,909 | | | | | | |
| 4.6 Investigator recruitment and Selection | X | ##### | | | | | | | 456,085 | | | | 27,480 | 27,480 |
| 4.6.1 Develop list of potential investigators | | X | | | site | 185 | 456 | 84,362 | | | | | | |
| 4.6.2 Qualification Telephone surveys | | X | | | site | 185 | 610 | 112,860 | | | | | | |
| 4.6.3 Pre-study Qualification Visits | | X | | | | | | | | | | | | |
| 4.6.3.1 Conduct site qualification visits | | X | | | site | 40 | 1,489 | 59,548 | | visit | 40 | 687 | | |
| 4.6.3.2 Provide written site evaluation report | | | X | | site | 40 | 612 | 24,464 | | | | | | |
| 4.6.4 Select sites | | | X | | | | | | | | | | | |
| 4.6.5 Prepare Investigator contract | X | | | | | | | | | | | | | |
| 4.6.6 Negotiate Investigator grants (site budgets) | X | | | | | | | | | | | | | |
| 4.6.7 Collect essential and reg documents | | X | | | site | 185 | 945 | 174,850 | | | | | | |

Figure 13-BB

| | | | | | | | |
|---|---|---|---|---|---|---|---|
| 4.8 Drug Supply | X | | | | | | |
| 4.8.1 Arrange drug packaging | X | | | | | | |
| 4.8.2 Arrange drug labeling | X | | | | | | |
| 4.8.3 Drug storage and distribution | X | | | | | | |
| 4.9 Patient randomization (IVRS?) (See Biostats) | | X | 1 | 2,388 | 2,388 | 2,388 | |
| 4.1 IRB/IEC | | X | | | | | |
| 4.10.1 Select Central IRB | | X | | | | | |
| 4.10.2 Manage Ethics Committee/IRBs submissinos | | X | | | | | |
| 4.10.3 Managage Regulatory Submissions | | X | | | | | |
| 4.11 Pk Assessments | | X | | | | | |
| 4.11.1 Identify Labs, NDA, RFP | X | | | | | | |
| 4.11.2 Vendor Audits | X | | | | | | |
| 4.11.3 Develop/Transfer procedures | X | | | | | | |
| 4.11.4 Per patient cost of Sample kits | X | | | | | | |
| 4.11.5 Shipping, testing, and storage procedures | X | | | | | | |
| 4.11.6 Sample archiving | X | | | | | | |
| 4.11.7 Electronic Data Collection | | X | | | | | |
| 4.11.8 Data Transfer | | X | | | | | |

Figure 13-CC

| | | | | | | | | | |
|---|---|---|---|---|---|---|---|---|---|
| 4.12 Central laboratory | X | | | | 23,905 | | | | |
| 4.12.1 Identify Labs, NDA, RFP | X | | | | | | | | |
| 4.12.2 Vendor Audits | | | | | | | | | |
| 4.12.3 Per patient cost of Sample kits | X | | | | | | | | |
| 4.12.4 Per patient cost of lab tests | X | | | | | | | | |
| 4.12.5 Sample archiving | X | | | | | | | | |
| 4.12.6 Electronic Data Collection | X | | timpoints | 6,300 | 4 | 23,905 | | | |
| 4.12.7 Data Transfer | X | | | | | | | | |
| 4.13 Site Study Binders | X | | | | | | | | | 9,768 |
| 4.13.1 Site Regulatory Binder | X | | | | | binder | 185 | 26 | 4,884 | |
| 4.13.2 Site Study Binder | X | | | | | binder | 185 | 26 | 4,884 | |
| 4.13.3 Site Pharmacy Binder | X | | | | | | | | | |
| 4.13.4 Site pK Binder | | | | | | | | | | |
| 4.14 Set Up CTMF | X | | | | | | | | | |
| 4.15 Recruit independent Data Monitoring committee | | X | | | | | | | | |
| 4.14 Investigator's meeting | X | | | | | 203,960 | | | | 36,294 |
| 4.14.1 Location | X | | | | | | | | | |
| 4.14.2 Agenda | | X | | | | | | | | |
| 4.14.3 Attendee list | | X | | | | | | | | |
| 4.14.4 Travel arrangements | | | | | | | | | | |
| 4.14.5 Run meeting | X | | | | | | | | | |
| 4.14.6 Presentations | X | | | 2 | 12,880 | 25,760 | | | | |
| 4.14.7 Meeting materials/Bindes | X | | | | | | | | | |
| 4.14.8 Attendance | X | | | 2 | 89,100 | 178,200 | | 2 | 18,147 | 36,294 |

Figure 13-DD

| DESCRIPTION | RESPONSIBILTIES ||||  ESTIMATED DIRECT COSTS |||| ESTIMATED PASSTHROUGH COSTS ||||
|---|---|---|---|---|---|---|---|---|---|---|---|---|
| | Sponsor | VENDER | Joint | n/a | Unit Type | Unit | Price per Unit | Item Total | SECTION SUB TOTAL | Unit Type | Unit | Price per Unit | Item Total | SECTION SUB TOTAL |
| 8 Drug Supply Management | X | X | X | | | | | | 53641 | | | | | |
| 8.1 Drug Supply Plan | X | X | X | | | | | | 53641 | | | | | |
| 8.1.1 Drug Supply | X | | | | | | | | | | | | | |
| 8.1.2 Packaging | X | | | | | | | | | | | | | |
| 8.1.3 Inventory Management | X | | | | | | | | | | | | | |
| 8.1.4 Randomization? | X | | | | | | | | | | | | | |
| 8.1.5 Pt level lot tracking | X | | | | | | | | | | | | | |
| 8.1.6 Distributor management | X | | | | | | | | | | | | | |
| 8.1.7 Country Specific Labels | X | | | | | | | | | | | | | |
| 8.1.8 Import licenses | X | X | | | license | 7 | 607 | 4,249 | | | | | | |
| Direct Cost | | | | | | | | | | | | | | |
| 8.1.10 Country Depots | X | | | | | | | | | | | | | |
| 8.1.8 Within Country Compartor Procurement | X | | | | | | | | | | | | | |
| 8.1.12 Shipping requirements (Hazardous?) | X | | | | | | | | | | | | | |
| 8.1.13 Shipper | X | | | | | | | | | | | | | |
| 8.1.14 Drug Distruction | | | X | | | 185 | 267 | 49,392 | | | | | | |
| 8.1.15 Final Reconciliation | | | X | | | | | | | | | | | |
| 8.1.16 Ancillary Supplies | X | | | | | | | | | | | | | |

Figure 13-EE

| | | | | | | | | | | | |
|---|---|---|---|---|---|---|---|---|---|---|---|
| 8.2 Supply Study Drug for packaging | x | x | | | | | | | | | |
| 8.2.1 Identify vendors for compators | x | | | | | | | | | | |
| 8.2.2 Import Licenses and Customs Clearance | | | x | | | | | | | | |
| 8.3 Package Study Drug | x | | | | | | | | | | |
| 8.4 Produce Randomization Code | x | | | | | | | | | | |
| 8.5 Label study drug | x | | | | | | | | | | |
| 8.6 Ship study drug to site | | | | x | | | | | | | |
| 8.7 Store study drug | | | | x | | | | | | | |
| 8.8 study drug accountability | | | | | | | | | | | |
| 8.9 Perform post-study drug accountability | | | x | | | | | | | | |
| 12 Study drug disposition & accountability | | | x | | | | | | | | |

Figure 13-FF

| DESCRIPTION | RESPONSIBILITIES ||| ESTIMATED DIRECT COSTS ||||| ESTIMATED PASSTHROUGH COSTS |||||
|---|---|---|---|---|---|---|---|---|---|---|---|---|
| | Sponsor | VENDER | Joint | n/a | Unit Type | ITEM TOTAL || SECTION SUB TOTAL | Unit Type | ITEM TOTAL || SECTION SUB TOTAL |
| | | | | | | Unit | Price per Unit | Item Total | | Unit | Price per Unit | Item Total |
| 9 Labs and Assessments | | | | | | | | | | | | |
| 9.1 Central lab | | | X | X | | | | | | | | |
| 9.1.1 per patient sampling kit cost | | | X | | | | | | | | | |
| 9.1.2 per patient testing cost | | | X | | | | | | | | | |
| 9.1.3 per patient shiping est. | | | X | | | | | | | | | |
| 9.1 pK Lab | | | | X | | | | | | | | |
| 9.1.1 Test Validation Charges | | | | | | | | | | | | |
| 9.1.2 per patient sampling kit cost | | | | | | | | | | | | |
| 9.1.3 per patient testing cost | | | | | | | | | | | | |
| 9.1.4 per patient shiping est. | | | | | | | | | | | | |
| Direct Cost | | | | | | | | | | | | |
| 9.2 Central Readers | | | | | | | | | | | | |

Figure 13-GG

| DESCRIPTION | RESPONSIBILITIES ||| ESTIMATED DIRECT COSTS |||||| ESTIMATED PASSTHROUGH COSTS ||||
|---|---|---|---|---|---|---|---|---|---|---|---|---|
| | Sponsor | VENDER | Joint | n/a | Unit Type | Unit | ITEM TOTAL Price per Unit | Item Total | SECTION SUB TOTAL | Unit Type | Unit | ITEM TOTAL Price per Unit | Item Total | SECTION SUB TOTAL |
| 6 Data Management | | | | | | | | | 935,535 | | | | | |
| 6.1 Data Project Management | X | X | | | | | | | | | | | | |
| 6.2 Develop Data Management and Quality Plan | | X | | | plan | 1 | 18,312 | 18,312 | 18,312 | | | | | |
| 6.2.1 Collaborate, review, and approve DM and DQ Plan | X | | | | | | | | | | | | | |
| 6.3 Status Reports CRFs; Data Entry; Queries | | X | | | page | 35,700 | 11 | 405,741 | 405,741 | | | | | |
| 6.4 Client Conference Calls | | | X | | | | | | | | | | | |
| 6.5 CRFs | | | X | | | | | | 31,217 | | | | | | 96,762 |
| CRFs/Paper or Electronic | | | | | | | | | | | | | | |
| 6.5.1.1 Provide Draft CRFs Direct Cost | | | | | page | 119 | 217 | 25,828 | | | | | | |
| 6.5.1.2 Design CRFs | | | | | | | | | | | | | | |
| 6.5.1.4 Approve CRFs | | | | | | | | | | | | | | |
| 6.5.2 Print CRFs | | | | | patient | 300 | 18 | 5,389 | | patient | 300 | 323 | 96,762 | |
| 6.5.3 Distribute CRFs to sites | | | | | | | | | | | | | | |
| 6.5.4 Electronic CRF | | X | | | | | | | | | | | | |
| 6.5.4.1 Server/Datase Configeration & Qualification | | X | | | | | | | | | | | | |
| 6.5.4.2 eCRF Design | | X | | | | | | | | | | | | |
| 6.5.4.3 eCRF Programming | | X | | | | | | | | | | | | |

Figure 13-HH

| | | | | | | | |
|---|---|---|---|---|---|---|---|
| 6.5.4.4 eCRF QC | | X | | | | | |
| 6.5.4.5 eCFR Approval | X | | | | | | |
| 6.5.4.6 eCRF Deployment | | X | | | | | |
| 6.5.4.7 eCRF Completion conventions | | | X | | | | |
| 6.6 Data Base Administration | X | X | X | | | 154,690 | |
| 6.6.1 Data Base Specification | | X | | | | | |
| 6.6.2 Data Base Design | | X | | database | 1 | 108,276 | 108,276 |
| 6.6.3 Approve DB Design | X | | | | | | |
| 6.6.4 Data Base QC | | X | X | QC | 2 | 16,408 | 32,816 |
| 6.6.5 Data Base Audit | | X | | | | | |
| 6.6.6 Data Base Documentation | | X | | listing | 30 | 453 | 13,598 |
| 6.7 Edit Checks | | X | | | | | |
| 6.7.1 Edit Check Specifications | | X | | | | | |
| 6.7.2 Edit Check Programing | | X | | | | | |
| 6.7.3 Edit Check QC | X | | X | page | 35,700 | 1 | 43,194 | 43,194 |
| 6.8 Self-Evident Edit Checks | | | | | | | 131,077 |
| 6.9 Data Entry | | X | | | | | |
| 6.9.1 eCRF at Site | | X | | | | | |
| 6.9.2 paper - Double Data entry | | | | page | 35,700 | 4 | 131,077 |
| 6.10.1 Dictionary Coding | | | X | | | | 62,005 |
| 6.10.1 SAE Coding | | | X | | | | |
| 6.10.2 Mediation Coding | | | X | patient | 300 | 207 | 62,005 |

Figure 13-II

| | | | | | | | | | | | |
|---|---|---|---|---|---|---|---|---|---|---|---|
| 6.11 CRF storage or imaging | | | | | | | | | | | |
| 6.12 Central Laboratory Data intergration | x | | | | | | | | | | |
| 6.12.1 Lab Normal Ranges | x | | | | | | | | | | |
| 6.13 Central Scan or X-ray data | x | | | | | | | | | | |
| 6.14 pK or -Special Assessment Data | x | | | | | | | | | | |
| 6.15 Query Generation and Query Management | x | x | | | | | | | 21,782 | | | |
| 6.15.1 Site generated Queries | x | | | | | | | | | | | |
| 6.15.2 CRA Generated Queries | | x | | | | | | | | | | |
| 6.15.3 Listing Review generated Queries | | x | | | | | | | | | | |
| 6.15.4 Central Reads generated queries | | | | | | | | | | | | |
| 6.15.5 SAE - AE reconciliation | x | | SAE | 300 | 73 | 21,782 | | | | | |
| 6.16 Monthly Transfer SAS datafiles | x | | transfer | 19 | 778 | 14,782 | 14,782 | | | | |
| 6.17 Track CRF, Queries, patients | x | | page | 35,700 | 1 | 52,735 | 52,735 | | | | |
| 6.18 Database Maintenance, Hosting and Support | x | | | | | | | | | | |

Figure 13-JJ

| DESCRIPTION | RESPONSIBILITIES ||||  ESTIMATED DIRECT COSTS |||||| ESTIMATED PASSTHROUGH COSTS ||||
| | Sponsor | VENDER | joint | n/a | Unit Type | ITEM TOTAL ||| SECTION SUB TOTAL | Unit Type | ITEM TOTAL ||| SECTION SUB TOTAL |
| | | | | | | Unit | Price per Unit | Item Total | | | Unit | Price per Unit | Item Total | |
|---|---|---|---|---|---|---|---|---|---|---|---|---|---|---|
| 5 Initiation and Monitoring | X | X | | | | | | | 16,085,324 | | | | | 2,896,096 |
| 5.1 Initiation | | X | | | | | | | 517,513 | | | | | 116,393 |
| 5.1.1 Prestudy Documentation | | X | | | site | 185 | 2,035 | 376,438 | | visit | 185 | 629 | 116,393 | |
| 5.1.3 Complete initiation visit report | | X | | | site | 185 | 763 | 141,075 | | | | | | |
| 5.2 Interim Monitoring | | X | | | | | | | 11,602,513 | | | | | 2,560,651 |
| 5.2.1 Conduct monitoring visits | | X | | | visit | 4,070 | 2,035 | 8,281,636 | | visit | 4,070 | 629 | 2,560,651 | |
| 5.2.2 Verify 100% of source documentation | | X | | | | | | | | | | | | |
| 5.2.3 Resolve edits/queries with site | | X | | | site | 185 | 378 | 69,920 | | | | | | |
| 5.2.4 Review drug records | | X | | | site | 185 | 796 | 147,308 | | | | | | |
| 5.2.5 Review lab storage | | X | | | | | | | | | | | | |
| Direct Cost | | X | | | | | | | | | | | | |
| 5.2.7 Interim Monitoring Visit report | | X | | | visit | 4,070 | 763 | 3,103,650 | | | | | | |
| 5.2.8 Complete interim monitoring report | | X | | | | | | | | | | | | |
| 5.3 Site Close-Out | X | X | | | | | | | 1,486,980 | | | | | 116,393 |
| 5.3.1 Conduct site close-out visits | | X | | | site | 185 | 2,035 | 376,438 | | visit | 185 | 629 | 116,393 | |
| 5.3.2 Site files complete; records archive | X | | | | month | 33 | 28,765 | 955,360 | | | | | | |
| 5.3.3 data queries resolved | | X | | | | | | | | | | | | |
| 5.3.4 sample archival discussed | | X | | | | | | | | | | | | |
| 5.3.5 drug reconciled | | X | | | | | | | | | | | | |
| 5.3.6 Survival | | X | | | | | | | | | | | | |
| 5.3.7 Provide close-out trip report | | X | | | site | 185 | 839 | 155,183 | | | | | | |

Figure 13-KK

| 5.4 Site General Administration | | | | | | | | | |
|---|---|---|---|---|---|---|---|---|---|
| | | | | | 2,478,317 | month | 33 | 3,091 | 102,659 |
| 5.4.1 Weekly telephone contact with sites | x | | week | 130 | 19,025 | 2,478,317 | | | |
| 5.4.2 Brief In-person site contact | x | | | | | | | | |
| 5.4.3 Investigator /institution grant administration | x | | | | | | | | |
| 5.4.4 Provide newsletters | x | | | | | | | | |
| 5.4.5 Provide helpdesk for study conduct (unrelated to eCRF) | x | | | | | | | | |
| | | | | | | | | 102,659 | |

Figure 13-LL

| DESCRIPTION | RESPONSIBILTIES ||||  | ESTIMATED DIRECT COSTS |||||  | ESTIMATED PASSTHROUGH COSTS ||||
|---|---|---|---|---|---|---|---|---|---|---|---|---|---|---|
| | Sponsor | VENDER | Joint | n/a | Unit Type | Unit | ITEM TOTAL || SECTION SUB TOTAL | Unit Type | Unit | ITEM TOTAL || SECTION SUB TOTAL |
| | | | | | | | Price per Unit | Item Total | | | | Price per Unit | Item Total | |
| 7 Statistical Analysis | X | | | | | | | | | | | | | |
| 7.1 Statistical Analysis Plan | X | | | | | | | | | | | | | |
| 7.1.1 Develop Analysis Plan | | | X | | | | | | | | | | | |
| 7.1.2 Review and Approve SAP | X | | | | | | | | | | | | | |
| 7.1.3 Number of tables (unique/total) | | | X | | | | | | | | | | | |
| 7.1.4 Number of Listings (unique/total) | | | X | | | | | | | | | | | |
| 7.1.5 Number of figures (unique/total) | | | X | | | | | | | | | | | |
| 7.2 Randomization Plan (IVRS?) | X | | | | | | | | | | | | | |
| 7.3 Data Monitoring Committee | | | | | | | | | | | | | | |
| 7.4 Table, Listing, and figure Programing | X | | | | | | | | | | | | | |
| Direct Cost | X | | | | | | | | | | | | | |
| 7.7 Query Generation | X | | | | | | | | | | | | | |
| 7.7 Interm Analysis | X | | | | | | | | | | | | | |
| 7.8 Draft T/L/F | X | | | | | | | | | | | | | |
| 7.9 Blinded/ Mock T/L/F | X | | | | | | | | | | | | | |

Figure 13-MM

| PROPOSED STUDY TARGET DATES | | |
|---|---|---|
| | Study Start Date | Q1-Q2 2007 |
| | Site Initiation (study set up 4 months) | March 2007 for site selection start |
| | Enrollment Period: | March/April 2007-December 2008 (18-24 months) |
| | | |
| | First Patient In | March/April 2007 (token USA pt) |
| | Last Patient In | March 2009 |
| | Treatment Period: | up to 6 cycles |
| | Last Patient Out | Sept 2009 |
| | Follow-up Period: | ~6 months |
| | Survival Follow up | SAA |
| | Interim Analysis | yes |
| | Last CRF in | TBD |
| | Clean Database Lock | Sept/Oct 2009 |
| | Statistical Analysis | TBD |
| | Clinical Study Report | Q4-2009 |
| | | |
| | | |

Figure 13-NN

| PROJECT OVERVIEW | | |
|---|---|---|
| | Compound Name | Xyotax |
| | Program Phase | Phase III |
| | Dosage Form | IV |
| | Indication | NSCLC, E+ female only |
| | Study Design | Randomized, Comparative |
| | Patient Population | • Locally advanced or recurrent disease previously treated with radiation and/or surgery, or stage IIIB or IV |
| | Number of Patients | 300 total |
| | World Regions (US; EU; ** May need to greatly increase number of sites in these countries. These are the only countries we will consider) | Spain, France, Belgium, Germany, USA, Canada, Australia, Czech, UK, |
| | Number of Investigators | 150-180 |
| | Approximate Number of Patients Per Site | 1-2 subjects/site |
| | Enrolment Rate | .5-1 patient per site every month |
| | Duration of Patient Participation | upto 6 cycles plus follow up period ~1 year |
| | -Screening/Run-In | <28 days |
| | - # of cycles | 6 |
| | -Follow-Up | 6 months |
| | -Survival Follow-Up | SAA |
| | Number of Protocol Summary Translations | French, Italian, Spanish, German, Danish, 3-5 Eastern Europe Translations, Mexico. |
| | Number of Full Protocol Translations | SAA |
| | Number of Informed Consent Translations | SAA |
| | Number of Investigators' Meetings | 1 per region |

Figure 13-OO

| Clincal Information | | |
|---|---|---|
| | Total Number of Monitoring Visits | Monitoring frequency every 6-8 weeks. |
| | -Potential sites Identified | |
| | -Pre-Study Evaluation (<1.2 X # ctrs) | 40 |
| | -Initiation (1 X # ctrs) | 150 |
| | -Interim Monitoring (IM) | every 6-8 weeks |
| | - IM Freq (enrollment) | within 3 weeks of FPI or sooner |
| | - IM Freq (treatment) | every 6-8 weeks |
| | - IM Freq (followup) | 2-3 months |
| | Number of Co-Monitoring Visits | 20 |
| | -Close-Out | 150 |
| | Total Number of Monitoring & close out Visits | |
| | Duration of Monitoring Visits (Hours) | 6 hours |
| | -Initiation | 24 (including travel/prep time) |
| | -Interim | 24 (including travel/prep time) |
| | -Close-Out | 24 (including travel/prep time) |
| | | |
| Project Management | | |
| | Number of COMPANY/CRO Project Team Meetings | Quarterly meetings |
| | Number of internal face-to-face CRO Project Team Meetings (1 kick-off meeting) | 6 |
| | COMPANY/CRO Project Team Teleconferences | Weekly |
| | Internal CRO project team teleconferences | TBD |
| Central Lab / Readers/ Special Assessments | | |
| | Central lab (Estrogen, LDH) | All labs |
| | | |
| | Local Labs: | Chem/cbc |

Figure 13-PP

| Data Management | | |
|---|---|---|
| | # of Unique CRF Pages | 33 |
| | # of CRF Pages/ Completed Patient | 209 |
| | # of CRF Pages/ Screen Failure Patients | None |
| | Will Screen Fail CRFs Be Processed (yes/no) | None |
| | # of CRF Pages/ Early Withdrawal | 23+(16xC), C=# of cycles |
| | Total # of CRFs to be Processed by Data Management | |
| | # of Queries/ Patient | 20 |
| | # of Manually Coded Items/ Patient | None |
| | # of Other Electronic Data Sources | One, central lab |
| | Data Transfers: | |
| | # of Cumulative Dirty DB Transfers | Twelve |
| | # of Cumulative Clean DB Transfers | Six |
| | # of Incrementally Clean DB Transfers | None |
| | Interim Analysis | |
| | # of Interim Analyses | 1 |
| | # of Interim Analyses to Support Planned Interim Analyses | 1 |
| | | |
| | Will there be an SAE Reconciliation to the Clinical Database (yes/no) | yes |
| | DSMC (yes/no) | no |
| | # of Times DSMC will Meet | |
| | Annual IND Filing (yes/no) | yes |

Figure 13-QQ

| DESCRIPTION | RESPONSIBILITIES | | | | ESTIMATED DIRECT COSTS | | | | | | ESTIMATED PASS-THROUGH COSTS | | | | |
|---|---|---|---|---|---|---|---|---|---|---|---|---|---|---|---|
| | Sponsor | VENDER | Joint | n/a | Unit Type | # Units | Price per Unit | Item Total | SECTION SUB TOTAL | Unit Type | # Units | Price per Unit | Item Total | SECTION SUB TOTAL | |
| 1 Project Management | X | X | X | | | | | | 7,544,609 | | | | | 148,149 | |
| 1.1 Time Line Management | X | X | X | | month | 33 | 131,828 | 4,378,411 | 4,378,411 | month | 33 | 2,773 | 92,085 | 92,085 | |
| 1.2 Team Management | X | X | X | | | | | | 2,988,989 | | | | | 29,100 | |
| 1.2.1 Status Reports | | X | | | week | 133 | 1,487 | 197,837 | | | | | | | |
| 1.2.1.1 Essential Doc. Version Tracking (approved. Prot; ICF; CRF; IB) | | X | | | | | | | | | | | | | |
| 1.2.1.2 Initiation (Ess. Doc tracking by country and site) | | X | | | | | | | | | | | | | |
| 1.2.1.3 Pt Recruitment | | X | | | | | | | | | | | | | |
| 1.2.1.4 Monitoring (Visits and reports) | X | X | | | report | 3,776 | 174 | 658,592 | | | | | | | |
| 1.2.1.5 CRF retrieval | | X | | | | | | | | | | | | | |
| 1.2.1.6 Queries (rate; closed; pending) | | X | | | | | | | | | | | | | |
| Direct Cost | | X | | | | | | | | | | | | | |
| 1.2.1.8 SAE | | X | | | | | | | | | | | | | |
| 1.2.1.9 Invest Grant payment | | | X | | payment per site | 2,590 | 119 | 307,024 | | | | | | | |
| 1.2.1.10 Vender payments | | X | X | | vendor | 4 | 23,225 | 92,901 | | | | | | | |
| 1.2.1.11 other | | X | | | | | | | | | | | | | |
| 1.2.2 Task List (Wkly Updates) | | X | | | | | | | | | | | | | |
| 1.2.3 Issues/Decision Log (Wkly Updates) | | X | | | | | | | | | | | | | |
| 1.2.4 CTI/ CRO Meeting Telecon. Agenda; Minutes (wkly) | | X | | | week | 143 | 3,405 | 486,940 | | teleconference | 143 | 203 | 29,100 | | |

Figure 13-RR

| Task | | | Unit | Qty | | | | | | | | | |
|---|---|---|---|---|---|---|---|---|---|---|---|---|---|
| 1.2.5 Weekly Monitoring Team Meetings | X | | week | 143 | 7,795 | 1,114,705 | | | | | | | |
| 1.2.6 Frequently Asked Questions for sites (Wkly) | X | | | | | | | | | | | | |
| 1.2.7 Study News Letter-(Mo/Qtr) (CRF completion updates; Protocol Clarifications; Freq Asked Questions; AE coding help) | X | | newsletter | 42 | 3,119 | 130,991 | | | | | | | |
| 1.3 Training | X | X | | | | | 177,208 | | | | | 26,963 | |
| 1.3.1 Project Familization | | X | meeting | 1 | 31,822 | 31,822 | | | | | | | |
| 1.3.2 CRO Kick Off Mtg | X | X | meeting | 1 | 35,136 | 35,136 | | meeting | | 1 | 5,947 | 5,947 | |
| 1.3.3 CTI/CRO Face to Face | | X | meeting | 5 | 22,050 | 110,250 | | meeting | | 5 | 4,203 | 21,017 | |
| 1.4 Recruitment Plan | X | | | | | | | | | | | | |
| 2 Medical Management | X | X | | | | | 663,153 | | | | | | |
| 2.1 Medical Monitoring/ PV | X | X | | | | | 663,153 | | | | | | |
| 2.1.1 Medical Monitor | X | | | | | | | | | | | | |
| 2.1.2 SAE Initial &Follow-up Reports | X | | SAE | 300 | 1,218 | 365,500 | | | | | | | |
| 2.1.3 SAE Narrative as part of SAE Rpt | X | | | | | | | | | | | | |
| 2.1.4 24 hr Med non SAE coverage | X | | | | | | | | | | | | |
| 2.1.5 Reportable Determination | X | | | | | | | | | | | | |
| 2.1.6 CRF or Table/Listing Safety | X | | | | | | | | | | | | |
| 2.1.7 Generation of IND / CIOMOS safety letter | X | | letter | 30 | 8,384 | 251,522 | | | | | | | |
| 2.1.8 Site Safety Report Submission | | X | | | | | | | | | | | |
| 2.1.9 Develop and maintain safety database | X | | | | | | | | | | | | |
| 2.1.10 Reconcile safety database with AE data base | | X | SAE | 300 | 154 | 46,131 | | | | | | | |

| | | | | | | | | | | | |
|---|---|---|---|---|---|---|---|---|---|---|---|
| 2.1.11 Distribute SAE and safety updates per GCP to sites | | | | X | | | | | | | |
| 2.1.12 DMC management/safety updates | X | | | | | | | | | | |
| 2.2 Quality Plan | X | | | | | | | | | | |
| 2.2.1 Vendor Audits | X | | | | | | | | | | |
| 2.2.2 Site Audits | X | | | | | | | | | | |
| 2.3 Records Archiving & Management | | | | | | | | | | | |
| 3 Vendor Administration | X | | | | | | | | | | |
| 3.1 Drug packaging facility payment | X | | | | | | | | | | |
| 3.2 Central laboratory payments | X | | | | | | | | | | |
| 3.3 Assessment Payments | X | | | | | | | | | | |
| 3.4 Central Reader Payment | X | | | | | | | | | | |

| DESCRIPTION | RESPONSIBILITIES | | | | Unit Type | ESTIMATED DIRECT COSTS | | | | ESTIMATED PASSTHROUGH COSTS | | | | |
|---|---|---|---|---|---|---|---|---|---|---|---|---|---|---|
| | Sponsor | VENDER | Joint | n/a | | ITEM TOTAL | | | SECTION SUB TOTAL | Unit Type | ITEM TOTAL | | | SECTION SUB TOTAL |
| | | | | | | Unit | Price per Unit | Item Total | | | Unit | Price per Unit | Item Total | |
| 4 Study Start Up | X | X | X | X | | | | | 1,358,663 | | | | | 233,937 |
| 4.1 Investigator Brochure/ Pharmacy Brochure | | X | | | | | | | 48,465 | | | | | |
| 4.1.1 Draft or update IB | X | | | | | | | | | | | | | |
| 4.1.2 Review and Approve | X | | | | | | | | | | | | | |
| 4.1.3 Distribute to Sites; IRB/IEC | | X | | | site | 185 | 262 | 48,465 | | | | | | |
| 4.2 Protocol development | X | X | | | | | | | 19,219 | | | | | 18,467 |
| 4.2.1 Literature review, background research | X | | | | | | | | | | | | | |
| 4.2.2 Design and write protocol | X | | | | | | | | | | | | | |
| 4.2.3 Review Protocol | X | | | | protocol | 1 | 6,272 | 6,272 | | | | | | |
| 4.2.4 Approve protocol | X | | | | | | | | | | | | | |
| Direct Cost | | X | | | | | | | | | | | | |
| 4.2.6 Translate Protocol | | X | | | translation | 5 | 2,589 | 12,947 | | translation | 5 | 3,693 | 18,467 | |
| 4.2.7 Copy & Distribute Protocol to sites | | X | | | | | | | | | | | | |
| 4.2.8 Protocol Amendments | X | | | | | | | | | | | | | |

Figure 13-UU

| Task | | | | | | | | | | | | | |
|---|---|---|---|---|---|---|---|---|---|---|---|---|---|
| 4.3 Informed Consent Development | x | x | x | | | | | | | | | | |
| 4.3.1 Draft Informed Consent Template | x | | | | unit | 1 | 6,956 | 6,956 | | | | | |
| 4.3.2 IC Template review and approval | | | x | | | | | | | | | | |
| 4.3.3 IC Translation | | x | | | | | | | | | | | |
| 4.4 CRF (see also DM) | x | x | | | | | | | | | | | |
| 4.4.1 Approve CRFs and patient assessment booklets | x | | | | | | | | | | | | |
| 4.4.2 CRF completion conventions | | | x | | | | | | | | | | |
| 4.5 Regulatory Submissions | | x | | | | | | | 583,383 | | | | 141,927 |
| 4.5.1 Manage regulatory submissions (based on FDA IND docs) | | x | | | site | 185 | 2,603 | 481,578 | | site | 185 | 767 | 141,927 |
| 4.5.2 Manage regulatory updates | | x | | | site | 185 | 550 | 101,805 | | | | | |
| 4.6 Investigator recruitment and Selection | x | #### | x | | | 185 | 465 | | 465,663 | | | | 27,480 |
| 4.6.1 Develop list of potential investigators | | | x | | site | 185 | 465 | 86,113 | | | | | |
| 4.6.2 Qualification Telephone surveys | | x | | | site | 185 | 622 | 115,080 | | | | | |
| 4.6.3 Pre-study Qualification Visits | | x | | | | | | | | | | | |
| 4.6.3.1 Conduct site qualification visits | | x | | | site | 40 | 1,518 | 60,710 | | visit | 40 | 687 | 27,480 |
| 4.6.3.2 Provide written site evaluation report | | | x | | site | 40 | 624 | 24,944 | | | | | |
| 4.6.4 Select sites | | | x | | | | | | | | | | |
| 4.6.5 Prepare Investigator contract | x | | | | | | | | | | | | |
| 4.6.6 Negotiate Investigator grants (site budgets) | x | | | | | | | | | | | | |

Figure 13-VV

| | | | site | 185 | 967 | 178,815 | | | | | | | | | | | | |
|---|---|---|---|---|---|---|---|---|---|---|---|---|---|---|---|---|---|---|
| 4.6.7 Collect essential and reg documents | | x | | | | | | | | | | | | | | | | |
| 4.8 Drug Supply | x | | | | | | | | | | | | | | | | | |
| 4.8.1 Arrange drug packaging | x | | | | | | | | | | | | | | | | | |
| 4.8.2 Arrange drug labeling | x | | | | | | | | | | | | | | | | | |
| 4.8.3 Drug storage and distribution | x | | | | | | | | | | | | | | | | | |
| 4.9 Patient randomization (IVRS?) (See Biostats) | | | | 1 | 2,436 | 2,436 | 2,436 | | | | | | | | | | | |
| 4.1 IRB/IEC | | x | | | | | | | | | | | | | | | | |
| 4.10.1 Select Central IRB | | x | | | | | | | | | | | | | | | | |
| 4.10.2 Manage Ethics Committee/IRBs submissinos | x | | | | | | | | | | | | | | | | | |
| 4.10.3 Managage Regulatory Submissions | x | | | | | | | | | | | | | | | | | |
| 4.11 Pk Assessments | x | | | | | | | | | | | | | | | | | |
| 4.11.1 Identify Labs, NDA, RFP | x | | | | | | | | | | | | | | | | | |
| 4.11.2 Vendor Audits | x | | | | | | | | | | | | | | | | | |
| 4.11.3 Develop/Transfer procedures | x | | | | | | | | | | | | | | | | | |
| 4.11.4 Per patient cost of Sample kits | x | | | | | | | | | | | | | | | | | |
| 4.11.5 Shipping, testing, and storage procedures | x | | | | | | | | | | | | | | | | | |
| 4.11.6 Sample archiving | x | | | | | | | | | | | | | | | | | |
| 4.11.7 Electronic Data Collection | | x | | | | | | | | | | | | | | | | |

Figure 13-WW

| | | | | | | | | | |
|---|---|---|---|---|---|---|---|---|---|
| 4.11.8 Data Transfer | x | | | | | | | | |
| 4.12 Central laboratory | x | | | 24,395 | | | | | |
| 4.12.1 Identify Labs, NDA, RFP | | x | | | | | | | |
| 4.12.2 Vendor Audits | | | | | | | | | |
| 4.12.3 Per patient cost of Sample kits | x | | | | | | | | |
| 4.12.4 Per patient cost of lab tests | x | | | | | | | | |
| 4.12.5 Sample archiving | x | | | | | | | | |
| 4.12.6 Electronic Data Collection | x | | timpoints | 6,300 | 4 | 24,395 | | | |
| 4.12.7 Data Transfer | x | | | | | | | | |
| 4.13 Site Study Binders | x | | | | | | | | 9,768 |
| 4.13.1 Site Regulatory Binder | x | | | | | | binder | 185 | 26 | 4,884 |
| 4.13.2 Site Study Binder | x | | | | | | binder | 185 | 26 | 4,884 |
| 4.13.3 Site Pharmacy Binder | x | | | | | | | | | |
| 4.13.4 Site pK Binder | | | | | | | | | | |
| 4.14 Set Up CTMF | x | | | | | | | | | |
| 4.15 Recruit independent Data Monitoring committee | | x | | | | | | | | |
| 4.14 Investigator's meeting | x | x | | | | 208,148 | | | | 36,294 |
| 4.14.1 Location | x | | | | | | | | | |
| 4.14.2 Agenda | | x | | | | | | | | |
| 4.14.3 Attendee list | | x | | | | | | | | |
| 4.14.4 Travel arrangements | x | | | | | | | | | |
| 4.14.5 Run meeting | x | | | | | | | | | |
| 4.14.6 Presentations | x | | | 2 | 13,144 | 26,288 | | | | |
| 4.14.7 Meeting materials/Bindes | x | | | | | | | | | |
| 4.14.8 Attendance | x | | | 2 | 90,930 | 181,860 | | 2 | 18,147 | 36,294 |

Figure 13-XX

| DESCRIPTION | RESPONSIBILITIES ||||| Unit Type | ESTIMATED DIRECT COSTS ITEM TOTAL |||| Unit Type | ESTIMATED PASSTHROUGH COSTS ITEM TOTAL ||||
|---|---|---|---|---|---|---|---|---|---|---|---|---|---|---|---|
| | Sponsor | VENDER | Joint | n/a | | | Unit | Price per Unit | Item Total | SECTION SUB TOTAL | | Unit | Price per Unit | Item Total | SECTION SUB TOTAL |
| 8 Drug Supply Management | X | X | X | | | | | | | 54842 | | | | | |
| 8.1 Drug Supply Plan | X | X | X | | | | | | | 54842 | | | | | |
| 8.1.1 Drug Supply | X | | | | | | | | | | | | | | |
| 8.1.2 Packaging | X | | | | | | | | | | | | | | |
| 8.1.3 Inventory Management | X | | | | | | | | | | | | | | |
| 8.1.4 Randomization? | X | | | | | | | | | | | | | | |
| 8.1.5 Pt level lot tracking | X | | | | | | | | | | | | | | |
| 8.1.6 Distributor management | X | | | | | | | | | | | | | | |
| 8.1.7 Country Specific Labels | X | | | | | | | | | | | | | | |
| 8.1.8 Import licenses | | X | | | license | | 7 | 620 | 4,340 | | | | | | |
| Direct Cost | X | | | | | | | | | | | | | | |
| 8.1.10 Country Depots | X | | | | | | | | | | | | | | |
| 8.1.8 Within Country Compartor Procurement | X | | | | | | | | | | | | | | |
| 8.1.12 Shipping requirements (Hazardous?) | X | | | | | | | | | | | | | | |
| 8.1.13 Shipper | X | | | | | | | | | | | | | | |
| 8.1.14 Drug Distruction | | | X | | | | 185 | 273 | 50,502 | | | | | | |
| 8.1.15 Final Reconciliation | | | X | | | | | | | | | | | | |
| 8.1.16 Ancillary Supplies | X | | | | | | | | | | | | | | |

Figure 13-YY

| | | | | | | | | | | | |
|---|---|---|---|---|---|---|---|---|---|---|---|
| 8.2 Supply Study Drug for packaging | x | | | | | | | | | | |
| 8.2.1 Identify vendors for compators | x | | | | | | | | | | |
| 8.2.2 Import Licenses and Customs Clearance | | x | | | | | | | | | |
| 8.3 Package Study Drug | x | | | | | | | | | | |
| 8.4 Produce Randomization Code | x | | | | | | | | | | |
| 8.5 Label study drug | x | | | | | | | | | | |
| 8.6 Ship study drug to site | x | | | | | | | | | | |
| 8.7 Store study drug | | | x | | | | | | | | |
| 8.8 study drug accountability | | | x | | | | | | | | |
| 8.9 Perform post-study drug accountability | | | x | | | | | | | | |
| 12 Study drug disposition & accountability | | | x | | | | | | | | |

Figure 13-ZZ

| DESCRIPTION | RESPONSIBILITIES ||||  ESTIMATED DIRECT COSTS |||||| ESTIMATED PASSTHROUGH COSTS |||||
|---|---|---|---|---|---|---|---|---|---|---|---|---|---|---|
| | Sponsor | VENDER | Joint | n/a | Unit Type | ITEM TOTAL ||| SECTION SUB TOTAL | Unit Type | ITEM TOTAL ||| SECTION SUB TOTAL |
| | | | | | | Unit | Price per Unit | Item Total | | | Unit | Price per Unit | Item Total | |
| 9 Labs and Assessments | | | | | | | | | | | | | | |
| 9.1 Central lab | | | X | X | | | | | | | | | | |
| 9.1.1 per patient sampling kit cost | | | X | | | | | | | | | | | |
| 9.1.2 per patient testing cost | | | X | | | | | | | | | | | |
| 9.1.3 per patient shiping est. | | | X | | | | | | | | | | | |
| 9.1 pK Lab | | | | X | | | | | | | | | | |
| 9.1.1 Test Validation Charges | | | | | | | | | | | | | | |
| 9.1.2 per patient sampling kit cost | | | | | | | | | | | | | | |
| 9.1.3 per patient testing cost | | | | | | | | | | | | | | |
| 9.1.4 per patient shiping est. | | | | | | | | | | | | | | |
| Direct Cost | | | | | | | | | | | | | | |
| 9.2 Central Readers | | | | | | | | | | | | | | |

Figure 13-AAA

| DESCRIPTION | RESPONSIBILITIES | | | | ESTIMATED DIRECT COSTS | | | | | ESTIMATED PASSTHROUGH COSTS | | | | |
|---|---|---|---|---|---|---|---|---|---|---|---|---|---|---|
| | Sponsor | VENDER | Joint | n/a | Unit Type | ITEM TOTAL | | | SECTION SUB TOTAL | Unit Type | ITEM TOTAL | | | SECTION SUB TOTAL |
| | | | | | | Unit | Price per Unit | Item Total | | | Unit | Price per Unit | Item Total | |
| 6 Data Management | X | | X | | | | | | 957,059 | | | | | |
| 6.1 Data Project Management | | | | | | | | | | | | | | |
| 6.2 Develop Data Management and Quality Plan | X | X | | | plan | 1 | 18,682 | 18,682 | 18,682 | | | | | |
| 6.2.1 Collaborate, review, and approve DM and DQ Plan | X | | | | | | | | | | | | | |
| 6.3 Status Reports CRFs; Data Entry; Queries | | X | | | page | 35,700 | 12 | 415,159 | 415,159 | | | | | |
| 6.4 Client Conference Calls | | | X | | | | | | | | | | | |
| 6.5 CRFs | | | X | | | | | | 31,830 | | | | | 96,762 |
| CRFs/Paper or Electronic | | | | | | | | | | | | | | |
| 6.5.1.1 Provide Draft CRFs | | | | | | | | | | | | | | |
| 6.5.1.2 Design CRFs | | | | | page | 119 | 221 | 26,327 | | | | | | |
| Direct Cost | | | | | | | | | | | | | | |
| 6.5.1.4 Approve CRFs | | | | | | | | | | | | | | |
| 6.5.2 Print CRFs | | X | | | patient | 300 | 18 | 5,503 | | patient | 300 | 323 | 96,762 | |
| 6.5.3 Distribute CRFs to sites | | X | | | | | | | | | | | | |
| 6.5.4 Electronic CRF | | | | | | | | | | | | | | |
| 6.5.4.1 Server/Datase Configeration & Qualification | | X | | | | | | | | | | | | |
| 6.5.4.2 eCRF Design | | | | | | | | | | | | | | |
| 6.5.4.3 eCRF Programming | | X | | | | | | | | | | | | |

Figure 13-BBB

| | | | | | | |
|---|---|---|---|---|---|---|
| 6.5.4.4 eCRF QC | x | | | | | |
| 6.5.4.5 eCRF Approval | x | | | | | |
| 6.5.4.6 eCRF Deployment | | x | | | | |
| 6.5.4.7 eCRF Completion conventions | | x | | | | |
| 6.6 Data Base Administration | x | x | | | | |
| 6.6.1 Data Base Specification | | x | | | | |
| 6.6.2 Data Base Design | x | | database | 1 | 110,557 | |
| 6.6.3 Approve DB Design | | x | | | | |
| 6.6.4 Data Base QC | x | | QC | 2 | 16,758 | 33,515 |
| 6.6.5 Data Base Audit | x | | | | | |
| 6.6.6 Data Base Documentation | x | | listing | 30 | 464 | 13,930 |
| 6.7 Edit Checks | x | | | | | |
| 6.7.1 Edit Check Specifications | x | | | | | |
| 6.7.2 Edit Check Programing | x | | | | | |
| 6.7.3 Edit Check QC | | x | | | | |
| 6.8 Self-Evident Edit Checks | x | | page | 35,700 | 1 | 44,086 |
| 6.9 Data Entry | x | | | | 44,086 | |
| 6.9.1 eCRF at Site | x | | | | 134,647 | 134,647 |
| 6.9.2 paper - Double Data entry | | | page | 35,700 | 4 | |
| 6.1 Dictionary Coding | | x | | | | |
| 6.10.1 SAE Coding | | x | | | | 63,238 |
| 6.10.2 Mediation Coding | | x | patient | 300 | 211 | 63,238 |
| 6.11 CRF storage or imaging | | | | | | |
| 6.12 Central Laboratory Data intergration | x | | | | | |
| 6.12.1 Lab Normal Ranges | x | | | | | |

Figure 13-CCC

| | | | | | | | | | |
|---|---|---|---|---|---|---|---|---|---|
| 6.13 Central Scan or X-ray data | X | | | | | | | | |
| 6.14 pK or -Special Assessment Data | X | | | | | | | | |
| 6.15 Query Generation and Query Management | X | X | | | | | | 22,232 | |
| 6.15.1 Site generated Queries | X | | | | | | | | |
| 6.15.2 CRA Generated Queries | | X | | | | | | | |
| 6.15.3 Listing Review generated Queries | | X | | | | | | | |
| 6.15.4 Central Reads generated queries | | | | | | | | | |
| 6.15.5 SAE - AE reconciliation | | X | SAE | 300 | 74 | | 22,232 | | |
| 6.16 Monthly Transfer SAS datafiles | X | | transfer | 19 | 793 | | 15,067 | 15,067 | |
| 6.17 Track CRF, Queries, patients | X | | page | 35,700 | 2 | | 54,115 | 54,115 | |
| 6.18 Database Maintenance, Hosting and Support | X | | | | | | | | |

Figure 13-DDD

| DESCRIPTION | RESPONSIBILITIES | | | ESTIMATED DIRECT COSTS | | | | | ESTIMATED PASSTHROUGH COSTS | | | | |
|---|---|---|---|---|---|---|---|---|---|---|---|---|---|
| | Sponsor | VENDER | Joint | n/a | Unit Type | ITEM TOTAL | | | SECTION SUB TOTAL | Unit Type | ITEM TOTAL | | SECTION SUB TOTAL |
| | | | | | | Unit | Price per Unit | Item Total | | | Unit | Price per Unit | Item Total | |
| 5 Initiation and Monitoring | X | X | | | | | | | 17,989,562 | | | | | 3,128,882 |
| 5.1 Initiation | | X | | | | | | | 527,668 | | | | | 116,393 |
| 5.1.1 Prestudy Documentation | | X | | | site | 185 | 2,075 | 383,818 | | visit | 185 | 629 | 116,393 | |
| 5.1.3 Complete initiation visit report | | X | | | site | 185 | 778 | 143,850 | | | | | | |
| 5.2 Interim Monitoring | | X | | | | | | | 12,885,496 | | | | | 2,793,437 |
| 5.2.1 Conduct monitoring visits | | X | | | visit | 4,440 | 2,075 | 9,211,632 | | visit | 4,440 | 629 | 2,793,437 | |
| 5.2.2 Verify 100% of source documentation | | X | | | | | | | | | | | | |
| 5.2.3 Resolve edits/queries with site | | X | | | site | 185 | 385 | 71,282 | | | | | | |
| 5.2.4 Review drug records | | X | | | site | 185 | 812 | 150,183 | | | | | | |
| 5.2.5 Review lab storage | | X | | | | | | | | | | | | |
| Direct Cost | | | | | | | | | | | | | | |
| 5.2.7 Interim Monitoring Visit report | | X | | | visit | 4,440 | 778 | 3,452,400 | | | | | | |
| 5.2.8 Complete interim monitoring report | | X | | | | | | | | | | | | |
| 5.3 Site Close-Out | X | X | | | | | | | 1,673,021 | | | | | |
| 5.4 Site General Administration | | X | | | | | | | 2,903,377 | | | | | 102,659 |
| 5.4.1 Weekly telephone contact with sites | | X | | | week | 130 | 22,288 | 2,903,377 | | month | 33 | 3,091 | 102,659 | |
| 5.4.2 Brief In-person site contact | | X | | | | | | | | | | | | |
| 5.4.3 Investigator/institution grant administration | | X | | | | | | | | | | | | |
| 5.4.4 Provide newsletters | | X | | | | | | | | | | | | |
| 5.4.5 Provide helpdesk for study conduct (unrelated to eCRF) | | X | | | | | | | | | | | | |

Figure 13-EEE

| DESCRIPTION | RESPONSIBILITIES ||||  | ESTIMATED DIRECT COSTS |||| | ESTIMATED PASSTHROUGH COSTS |||| |
|---|---|---|---|---|---|---|---|---|---|---|---|---|---|---|
| | Sponsor | VENDER | Joint | n/a | Unit Type | ITEM TOTAL ||| SECTION SUB TOTAL | Unit Type | ITEM TOTAL ||| SECTION SUB TOTAL |
| | | | | | | Unit | Price per Unit | Item Total | | | Unit | Price per Unit | Item Total | |
| 7 Statistical Analysis | X | | | | | | | | | | | | | |
| 7.1 Statistical Analysis Plan | X | | | | | | | | | | | | | |
| 7.1.1 Develop Analysis Plan | X | | | | | | | | | | | | | |
| 7.1.2 Review and Approve SAP | X | | | | | | | | | | | | | |
| 7.1.3 Number of tables (unique/total) | X | | | | | | | | | | | | | |
| 7.1.4 Number of Listings (unique/total) | X | | | | | | | | | | | | | |
| 7.1.5 Number of figures (unique/total) | X | | | | | | | | | | | | | |
| 7.2 Randomization Plan (IVRS?) | X | | | | | | | | | | | | | |
| 7.3 Data Monitoring Committee | | | | | | | | | | | | | | |
| 7.4 Table,Listing, and figure Programing | X | | | | | | | | | | | | | |
| Direct Cost | X | | | | | | | | | | | | | |
| 7.7 Query Generation | X | | | | | | | | | | | | | |
| 7.7 Interim Analysis | X | | | | | | | | | | | | | |
| 7.8 Draft T/L/F | X | | | | | | | | | | | | | |
| 7.9 Blinded/ Mock T/L/F | X | | | | | | | | | | | | | |

Figure 14
Excerpt from CRO 1 Proposal

A. have recently had a site qualification visit performed by XXX, or received a qualification visit from XXXXXXX® within the last year, may not require a qualification visit. XXXXXXX® will advise XXX of sites that may not require a qualification visit. XXX shall make the final decision regarding waiver of a site's qualification visit. The amount of time allotted for conduct of the visit agenda, travel time and in-house time is described in the Study Budget, under Task Description.

The areas that will be covered during the qualification visit include:

- Qualifications of the investigator(s) and research staff
- Adequacy of the facilities
- Adequacy of time/interest/resources
- Appropriate patient population
- Understanding of study (e.g., study design, objectives, eligibility criteria, test parameters and visit schedule)
- Compliance with regulations (e.g., understanding of regulatory requirements and willingness to adhere to regulations)
- Appropriate secured area for drug storage (if relevant)
- Ongoing studies/competing protocols
- Confirm budget acceptance B. Conduct one (1) study initiation visit to each study site by a member of our senior staff. Senior staff refers to project managers and lead clinical research associate. The amount of time allotted for conduct of the visit agenda, travel time and in-house time is described in the Study Budget, under Task Description.

C. Conduct routine monitoring visits following enrollment of the first patient. Monitoring visits will be conducted in compliance with the monitoring plan that is prepared prior to the start of the study. In general, <u>monitoring visits will be conducted approximately every six to eight (8) weeks,</u> provided that a patient has been enrolled at the site and is either actively on-study or newly off-study. Study sites with a significant number of patients or outstanding issues will be monitored more frequently than the sites with fewer patients and issues. It is anticipated that at least 5% of the sites will be monitored more frequently than every eight (8) weeks. The following are the activities that XXXXXXX® will complete in accordance with the Monitoring Plan:

- Review 100% of all informed consent forms
- Assure all SAEs have been reported
- Review regulatory binder (e.g., Investigator Study Manual)
- Verify patient registration 100% CRF review against source documentation unless a lesser amount of source document verification is agreed upon with the XXX prior to the start of the study

Figure 15

| DESCRIPTION | RESPONSIBILITIES ||| ESTIMATED DIRECT COSTS ||||| ESTIMATED PASSTHROUGH COSTS |||||
|---|---|---|---|---|---|---|---|---|---|---|---|---|---|
| | Sponsor | VENDER | Joint | n/a | Unit Type | ITEM TOTAL |||SECTION SUB TOTAL | Unit Type | ITEM TOTAL ||| SECTION SUB TOTAL |
| | | | | | | Unit | Price per Unit | Item Total | | | Unit | Price per Unit | Item Total | |
| 5 Initiation and Monitoring | X | X | | | | | | | 3683632.5 | | | | | 540000 |
| 5.1 Initiation | | X | | | site | 150 | 3365 | | 504750 | | | | | 180000 |
| 5.1.1 Prestudy Documentation | | X | | | site | 150 | 560 | 84000 | | site | 150 | 1200 | 180000 | |
| 5.1.2 Conduct site initiation visits | | X | | | site | 150 | 2240 | 336000 | | | | | | |
| 5.1.3 Complete initiation visit report | | X | | | site | 150 | 565 | 84750 | | | | | | |
| 5.2 Interim Monitoring | | X | | | RMVs | 453 | 3392.5 | | 1536802.5 | | | | | 180000 |
| 5.2.1 Conduct monitoring visits | | X | | | RMVs | 453 | 1820 | 824460 | | RMVs | 150 | 1200 | 180000 | |
| 5.2.2 Verify 100% of source documentation | | X | | | RMVs | 453 | 280 | 126840 | | | | | | |
| 5.2.3 Resolve edits/queries with site | | X | | | RMVs | 453 | 280 | 126840 | | | | | | |
| 5.2.4 Review drug records | | X | | | RMVs | 453 | 280 | 126840 | | | | | | |
| 5.2.5 Review lab storage | | X | | | RMVs | 453 | 280 | 126840 | | | | | | |
| Direct Cost | | X | | | | | | | | | | | | |
| 5.2.7 Interim Monitoring Visit report | | X | | | RMVs | 453 | 452.5 | 204982.5 | | | | | | |
| 5.2.8 Complete interim monitoring report | | X | | | | | | | | | | | | |
| 5.3 Site Close-Out | X | X | | | site | 150 | 3365 | | 504750 | | | | | 180000 |

Figure 16-A

| | A | B | C | D | E | F | G | H | I |
|---|---|---|---|---|---|---|---|---|---|
| 1 | Date: | | 4/25/2007 | | | | | | |
| 2 | Compound: | | | | | | | | |
| 3 | Sponsor: | | | | | | | | |
| 4 | Contact: | | | | | | | | |
| 5 | Study Phase: | | | | | | | | |
| 6 | Study Title: | | | | | | | | |
| 7 | Protocol Number: | | | | | | | | |
| 8 | Contract Initiation Date | | May-07 | | | | | | |
| 9 | First Patient Enrolled | | Jul-07 | | | | | | |
| 10 | Completion of Contract | | Mar-10 | | | | | | |
| 11 | | | | | | | | | |
| 12 | RFP Specifications: | | | | RFP Services Requested: | | | Vendor Services: | 0=No, 1=Yes |
| 13 | Total Sites | | 150 | x | Integrations | $950,617 | | Data Management | |
| 14 | Sites US | | 0 | x | Integrations | 1 | | Central Lab Downloads | 30 |
| 15 | Sites ROW | | 150 | x | Reconciliations | 1 | | Database Transfers | 2 |
| 16 | Patients Screened | | 1500 | x | Logistics | 1 | | Total CRFs | 85,899 |
| 17 | Screened to Enrolled Ratio | | 5.000 | x | Portal | 1 | | Electronic Transfers | 177 |
| 18 | Patients Enrolled | | 300 | x | Project Accounting | 1 | | Client Templates for CRFs | 0 |
| 19 | Enrolled to Completed Ratio | | 1.000 | | Systems | $1,107,593 | | E-Diary Transfers | 0 |
| 20 | Patients Completed | | 300 | x | IVRS/ IWR | 1 | | Study Start Up Required | 1 |
| 21 | Start Up Period | | 3 | x | IVRS/ Diary | 0 | | Quarters | 11.5 |
| 22 | Enrollment Period (Months) | | 24 | x | ESSDS Safety | 1 | | Central IRB sites | 1 |
| 23 | Treatment Period (Months) | | 6 | x | Site Compliance tools | 1 | | Local IRB sites | 0 |
| 24 | Close Out Period (Months) | | 2 | x | Screening Enrollment tools | 1 | | Regulatory Doc. Binders | 150 |
| 25 | Total Study Length (Months) | | 34.5 | x | Reporting and Document MGT | 1 | | Study Manuals | 300 |
| 26 | Treatment Period (Weeks) | | 24 | x | Monitoring System | 1 | | Study Team | 18 |
| 27 | Monitoring/Live Period (Weeks) | | 128 | x | Activities of Staff | $4,005,621 | | Safety Required | 1 |
| 28 | Study Length (Weeks) | | 149 | x | Protocol and Study Documents | 1 | | Expedited Reports | 30 |
| 29 | Unique CRFs per Patient | | 33 | x | Project Management | 1 | | Patient Narratives | 30 |
| 30 | Repeat CRFs per Patient | | 176 | x | Data Management | 1 | | Monitoring Required | 1 |
| 31 | Total CRF per Patient | | 209 | x | CRF Design | 1 | | Interim Visits Freq. (Weeks) | 6 |
| 32 | CRAs (US) | | 0 | x | Database Design | 1 | | Initiation Teleconference | 0 |
| 33 | CRAs (ROW) | | 45 | x | Develop Data Management Plan | 1 | | Pharmacy Visits | 0 |
| 34 | Users | | 375 | x | Setup Database | 1 | | Qualification Visits | 40 |
| 35 | Tablets/pda | | 152 | x | Develop Edit Check and Coding Programs | 1 | | Initiation Visits | 150 |
| 36 | Inv Mtgs US | | 1 | x | Data Entry/Cleaning | 0 | | Interim Visits--Paper CRFs | 3193 |
| 37 | Inv Mtgs ROW | | 2 | x | Run Database Cleaning | 1 | | Close-Out Visits | 150 |
| 38 | Total Inv. Mtgs | | 3 | x | Database Audit | 1 | | Total Monitoring Visits | 3533 |
| 39 | Kick off Mtgs US | | 1 | x | TOTAL | $6,063,832 | | Audits Required | 1 |
| 40 | Kick off Mtgs ROW | | 0 | x | | | | Site Audits | 15 |

Figure 16-B

| | A | B | C | D | E | F | G | H | I |
|---|---|---|---|---|---|---|---|---|---|
| | | | | | MULTIPLIERS | | | | |
| 41 | | Total Kick off Mtgs | 1 | x | | | | GCP Audits | 1 |
| 42 | | IM/Trainning Staff | 1 | x | Start Up, Regulatory & Site Management | | | Study File Audit | 1 |
| 43 | | Support Staff | 1 | x | Monitoring | 1.00 | | Biostats Required? | 0 |
| 44 | | Vendor Ini. visits US | 11 | | Project Management | 1.00 | | Number of Tables/Appendices | 0 |
| 45 | | Vendor Ini. visits ROW | 11 | | Data Management | 1.00 | | SAP | 0 |
| 46 | | Query Rate | 0.03 | x | Safety, Medical & Scientific Services | 1.00 | | Unique Listings | 0 |
| 47 | | Estimated Queries | 6,000 | x | Biostatistics & Medical Writing | 1.00 | | Unique Summaries | 0 |
| 48 | | Edit Checks | 264 | x | Integrations | 2.00 | | Final Graphs | 0 |
| 49 | | Edit Checks per page | 8 | x | Reconciliations | 2.00 | | Subset Summaries | 0 |
| 50 | | Integrations | 3 | x | Logistics | 2.00 | | Subset Listings | 0 |
| 51 | | Cust Rpts | 0 | x | Portal | 1.00 | | Final Analysis | 0 |
| 52 | | Standard | 0 | x | Project Accounting | 1.00 | | PM Required? | 1 |
| 53 | | Configured | 0 | x | IVRS/IWR | 1.00 | | Training Meeting | 3 |
| 54 | | Meds per Patient | 10 | x | IVRS/Diary | 1.00 | | Client Meetings | 3 |
| 55 | | Disease/Pt | 10 | x | ESSDS Safety | 1.00 | | Vendor to Manage | 1 |
| 56 | | Coded Terms per Patient (AEs) | 10 | x | Site Compliance tools | 1.00 | | Project Mngt Hours Week | 90 |
| 57 | | Total Coded Terms | 45,000 | x | Screening Enrollment tools | 2.00 | | Study Material | 1 |
| 58 | | SAEs | 30 | x | Reporting and Document Mgt | 1.00 | | SAE Form | 0 |
| 59 | | SafetyDB | 1 | x | Monitoring System | 1.00 | | Informed Consent Form | 0 |
| 60 | | SAS Transfers (out) | 3 | x | | | | CRF Design | 0 |
| 61 | | Interim Analysis/Locks | 1 | x | | | | Investigator Brochure | 0 |
| 62 | | IVR Required? | 1 | x | Just in time Delivery | TRUE | | CRF Review and Comm. | 0 |
| 63 | | Treatment arms | 2 | x | Drug | - | | Additional Study Material | 1 |
| 64 | | Calls/pt | 1 | x | Labs/pt | - | | Protocol Review and Comm. | 0 |
| 65 | | Call Duration | 2.5 | x | ECG | - | | Document Translations | 0 |
| 66 | | IVRS Calls for Randomization | 450 | x | Glucometers | - | | Document Management | 0 |
| 67 | | Number of Randomization Arms | | x | Diary Device | - | | Protocol Preparation | 0 |
| 68 | | Countries | 9 | x | Others | | | DCMs | 1 |
| 69 | | IVRS (Invt. Meeting) Attendance | 1 | x | Total | | | DCIs | 0 |
| 70 | | SIV (US) | | x | | | | Lab Panels (Screens) | 0 |
| 71 | | SIV (ROW) | 45 | x | IVRS/IWR - LEVEL | 1.00 | | | 0 |
| 72 | | Audited CRFs | 8589.9 | x | $ | 26,250 | | Clinical Team | 15 |
| 73 | | Vendor Audits US | 0 | x | | | | | 0 |
| 74 | | Vendor Audits ROW | 0 | x | TOOLS - LEVEL | 1.00 | | | |
| 75 | | Sub Contractors | 3 | x | $ | 15,750 | | | |
| 76 | | IVRS Patients Diary | 0 | x | | | | | |
| 77 | | # Diary Calls Per Patient | 0 | x | INTEGRATIONS - LEVEL | 1.00 | | | |
| 78 | | Adm. Grants Paym. | 0 | x | $ | 15,750 | | | |

Figure 17

| | I | J | K | L | M | N |
|---|---|---|---|---|---|---|
| 1 | XXX | | $4,536,766 | | | |
| 2 | | | | | | |
| 3 | Professional Fees | | | | | |
| 4 | Start Up | Monitoring | PM | DM | Safety | Biostats |
| 5 | | | | 52,824 | 150,000 | - |
| 6 | 32,456 | 1,140,000 | 414,224 | 23,136 | | - |
| 7 | 7,500 | 225,000 | | 8,712 | - | - |
| 8 | 7,500 | 337,500 | 647,500 | 16,896 | - | - |
| 9 | 318,750 | - | 150,000 | 7,232 | | - |
| 10 | 187,500 | - | 150,000 | 9,323 | | - |
| 11 | 154,500 | - | - | 30,492 | | - |
| 12 | | - | - | 11,639 | | |
| 13 | | - | - | 194,840 | - | - |
| 14 | | - | - | 194,762 | | - |
| 15 | | | | 39,600 | | |
| 16 | | | | 15,640 | | |
| 17 | | | | 9,240 | | |
| 18 | | | | | | |
| 19 | | | | | | |
| 20 | | | | | | |
| 21 | | | | | | |
| 22 | | | | | | |
| 23 | | | | | | |
| 24 | | | | | | |
| 25 | | | | | | |
| 26 | | | | | | |
| 27 | | | | | | |
| 28 | | | | | | |
| 29 | | | | | | |
| 30 | | | | | | |
| 31 | | | | | | |
| 32 | | | | | | |
| 33 | | | | | | |
| 34 | | | | | | |
| 35 | | | | | | |
| 36 | | | | | | |
| 37 | | | | | | |
| 38 | | | | | | |
| 39 | | | | | | |
| 40 | | | | | | |
| 41 | | | | | | |
| 42 | | | | | | |
| 43 | - | - | - | - | | |
| 44 | - | - | - | - | | |
| 45 | - | - | - | - | | |
| 46 | - | - | - | - | | - |
| 47 | - | - | - | - | | - |
| 48 | - | - | - | - | | - |
| 49 | - | - | - | - | - | - |
| 50 | - | - | - | - | | |
| 51 | | | | | | |
| 52 | $ 708,206 | $ 1,702,500 | $ 1,361,724 | $ 614,336 | $ 150,000 | $ - |

Figure 18

| | B | C | D | E | F | G |
|---|---|---|---|---|---|---|
| 55 | XX | | $25,008,616 | | | |
| 56 | | | | | | |
| 57 | Professional Fees | | | | | |
| 58 | Start Up | Monitoring | PM | DM | Safety | Biostats |
| 59 | 6,142 | 24,464 | 2,478,317 | 12,928 | 9,001 | |
| 60 | 49,209 | 35,084 | 109,980 | 20,541 | 2,312 | |
| 61 | 18,312 | 24,464 | 194,113 | 4,992 | 316,617 | |
| 62 | 5,600 | 225,720 | 950,854 | 1,248 | 25,619 | |
| 63 | 2,388 | | 415,566 | 16,224 | 247,734 | |
| 64 | 63,325 | 141,075 | 108,058 | 10,366 | 45,231 | |
| 65 | 84,362 | 4,965,840 | 2,996,570 | 52,735 | 4,968 | |
| 66 | 25,828 | | 599,699 | 65,538 | | |
| 67 | 5,389 | 3,103,650 | | 65,538 | | |
| 68 | 47,431 | 225,720 | | 43,194 | | |
| 69 | 6,803 | | | 182,668 | | |
| 70 | 11,503 | 155,183 | | 170,338 | | |
| 71 | 112,860 | | | 21,782 | | |
| 72 | | 2,714,090 | | 5,809 | | |
| 73 | | | | 18,096 | | |
| 74 | 41,880 | | | 14,782 | | |
| 75 | 34,460 | | | 52,735 | | |
| 76 | 31,180 | | | 62,005 | | |
| 77 | 379,469 | | | 9,614 | | |
| 78 | 35,886 | | | 32,364 | | |
| 79 | 174,850 | | | 13,707 | | |
| 80 | 91,986 | | | 19,109 | | |
| 81 | 920,316 | | | 13,598 | | |
| 82 | 258,333 | | | 69,920 | | |
| 83 | 60,024 | | | 161,820 | | |
| 84 | 920,198 | | | | | |
| 85 | 91,001 | | | | | |
| 86 | 160,395 | | | | | |
| 87 | 107,908 | | | | | |
| 88 | | | | | | |
| 89 | | | | | | |
| 90 | | | | | | |
| 91 | | | | | | |
| 92 | | | | | | |
| 93 | | | | | | |
| 94 | | | | | | |
| 95 | | | | | | |
| 96 | | | | | | |
| 97 | | - | - | - | - | - |
| 98 | - | - | - | - | - | - |
| 99 | - | - | - | - | - | - |
| 100 | - | - | - | - | - | - |
| 101 | - | - | - | - | - | - |
| 102 | - | - | - | - | - | - |
| 103 | - | - | - | - | - | - |
| 104 | - | - | - | - | - | - |
| 105 | | | | | | |
| 106 | $ 3,747,037 | $ 11,615,290 | $ 7,853,157 | $ 1,141,651 | $ 651,482 | $ - |

Figure 19

| | B | C | D | E | F | G | H |
|---|---|---|---|---|---|---|---|
| | | | | | CRO 2 | CRO 4 | Benchmark |
| 110 | Professional Fees | | | | | | |
| 111 | Start Up, Regulatory & Site Management | | | | 708,206 | 3,747,037 | 1,280,322 |
| 112 | Monitoring | | | | 1,702,500 | 11,615,290 | 10,418,556 |
| 113 | Project Management | | | | 1,361,724 | 7,853,157 | 2,869,318 |
| 114 | Data Management | | | | 614,336 | 1,141,651 | 1,158,618 |
| 115 | Safety, Medical & Scientific Services | | | | 150,000 | 651,482 | 861,398 |
| 116 | Biostatistics & Medical Writing | | | | | | |
| 117 | Total Professional Fees | | | | 4,536,766 | 25,008,616 | 16,588,211 |
| 118 | Tools and Systems | | | | | | |
| 119 | IVRS | | | | Not Included | | Not Included |
| 120 | IVRS Diary Activities | | | | NA | NA | |
| 121 | Screening and Enrollment Tools | | | | Not Included | 308,711 | |
| 122 | Site Compliance Tools (EDC Included Free) | | | | Not Included | Not Included | |
| 123 | Integrated, Web-Based Monitoring System (with Centralized Trip Reports) | | | | Not Included | Not Included | |
| 124 | Real Time Reporting Tools (with Document Management System) | | | | Not Included | Not Included | |
| 125 | Single Portal Connecting to Interoperable Neural Network of Suppliers | | | | Not Included | Not Included | |
| 126 | All Custom Complete Integration and Interoperability | | | | Not Included | Not Included | |
| 127 | Ongoing Consolidation and Reconciliation | | | | Not Included | Not Included | |
| 128 | Early Safety Signal Detection System | | | | Not Included | Not Included | |
| 129 | Interoperable System for Supplies and Re-Supply Logistics Management | | | | Not Included | Not Included | |
| 130 | Project Accounting | | | | Not Included | Not Included | |
| 131 | Total Tools and Systems | | | | $ - | $ 308,711 | $ - |
| 132 | Pass-Through Expenses | | | | | | |
| 133 | EDC | | | | | | |
| 134 | Investigator Meetings | | | | 239,100 | 203,960 | |
| 135 | Investigator Fees | | | | TBD | | |
| 136 | Monitor Travel | | | | TBD | 3,616,152 | |
| 137 | Travel to Training Meetings | | | | | | |
| 138 | Travel to Client Meetings | | | | | 63,257 | |
| 139 | Travel for Audit Visits | | | | | | |
| 140 | Drug | | | | 87,300 | 224,489 | |
| 141 | Shipping, Printing and others | | | | | 326,624 | |
| 142 | Diagnostics | | | | 76,350 | | |
| 143 | Translation | | | | | 12,652 | |
| 144 | LABS | | | | | | |
| 145 | ECG | | | | | | |
| 146 | Total Pass-Through Expenses | | | | $ 402,750 | $ 4,447,134 | $ - |
| 147 | Total Project Cost | | | | $ 4,939,516 | $ 29,764,461 | $ 16,588,211 |

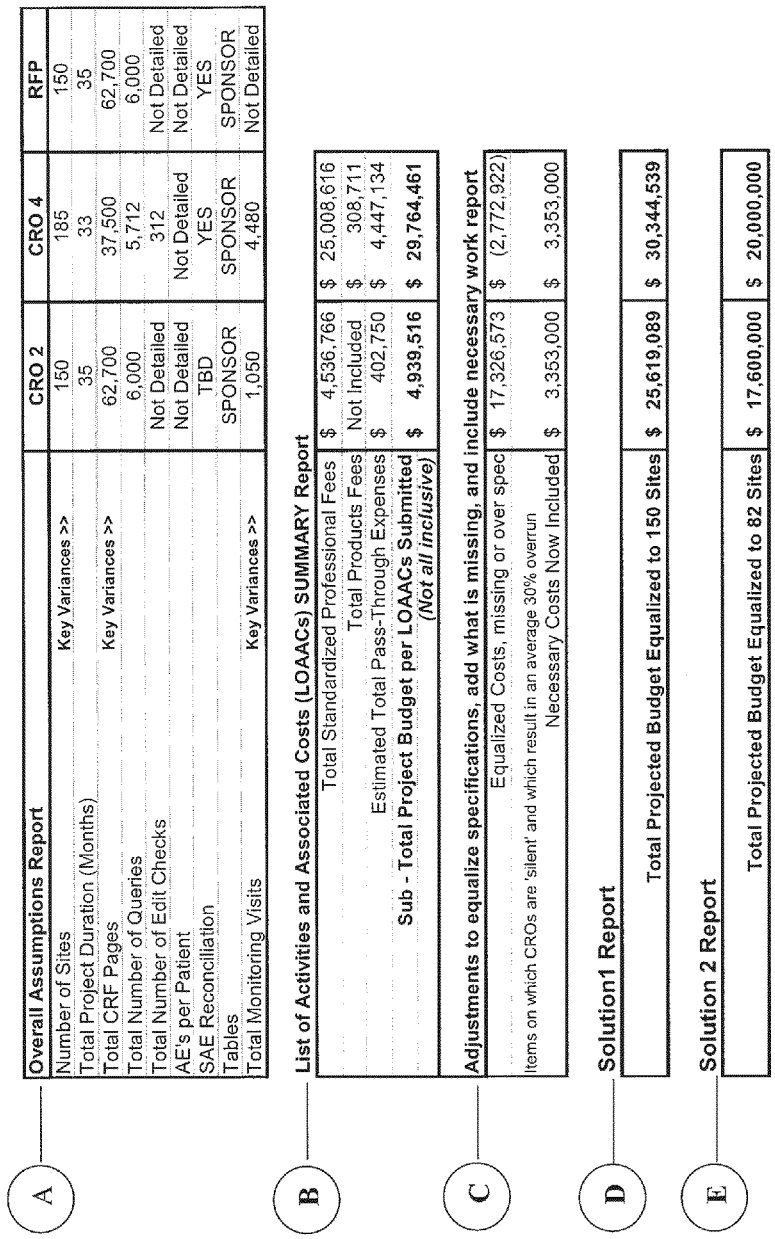

Figure 21
Detail Of Differences Reports - Metrics

Comparison of major assumptions, and the associated professional fees and passthrough costs, in detail taken from the List of Activities and Associated Costs (LOAACs) and RFP

| | CRO 2 | CRO 4 | RFP |
|---|---|---|---|
| Overall Assumptions Report | | | |
| Sites | 150 | 185 | 150 |
| Patients Screened | Not Detailed | 400 | 1,500 |
| Patients Enrolled | Not Detailed | 300 | 300 |
| Patients Completed | 300 | 300 | 300 |
| Countries | 9 | Not Detailed | 9 |
| Startup (Months) | 4.0 | 3.0 | 3.0 |
| Recruitment (Months) | 24.0 | 22.0 | 24.0 |
| Treatment (Months) | 6.0 | 5.5 | 5.5 |
| Closeout (Months) | 1.0 | 2.5 | 2.0 |
| Total Project Duration (Months) | 35.0 | 33.0 | 34.5 |
| | | | |
| Project Management Assumptions Report | | | |
| Status Reports | Monthly | 133 | Not Detailed |
| Newsletters | Not Detailed | 36 | Not Detailed |
| | | | |
| Total CRF Pages | 62,700 | 37,500 | 62,700 |
| Interim Analysis | 1 | Not Included | 1 |
| Con Meds per Patient | Not Detailed | Not Detailed | Not Detailed |
| Disease per Patient | Not Detailed | Not Detailed | Not Detailed |
| | | | |
| Safety Report | | | |
| SAE's | Not Detailed | 300 | Not Detailed |
| Safety Database | Not Detailed | YES | YES |

Figure 22-A
Detail of Differences Reports – Financial

Comparison of major assumptions, and the associated professional fees and passthrough costs, in detail token from the List of Activities and Associated Costs (LOAACs)

| Overall Assumptions Report | CRO 2 | CRO 4 |
|---|---|---|
| Start Up, Regulatory & Site Management | 708,206 | 3,747,037 |
| Monitoring | 1,702,500 | 11,615,290 |
| Project Management | 1,361,724 | 7,853,157 |
| Data Management | 614,336 | 1,141,651 |
| Safety, Medical & Scientific Services | 150,000 | 651,482 |
| Biostatistics & Medical Writing | - | - |
| Total Standardized Professional Fees | $ 4,536,766 | $ 25,008,616 |

| Project Management Assumptions Report | CRO 2 | CRO 4 |
|---|---|---|
| Screening and Enrollment Tools | Not Included | Not Included |
| Site Compliance Tools (EDC Included Free) | Not Included | Not Included |
| Integrated, Web-Based Monitoring System (with Centralized Trip Reports) | Not Included | Not Included |
| Real Time Reporting Tools (with Document Management System) | Not Included | Not Included |
| Single Portal Connecting to Interoperable Neural Network of Suppliers | Not Included | Not Included |
| All Custom Complete Integration and Interoperability | Not Included | Not Included |
| Ongoing Consolidation and Reconciliation | Not Included | Not Included |
| Early Safety Signal Detection System | Not Included | Not Included |
| Interoperable System for Supplies and Re-Supply Logistics Management | Not Included | Not Included |
| Project Accounting | Not Included | Not Included |
| IVRS | Not Included | 308,711 |
| IVRS Diary Activities | NA | NA |
| TOTAL | $ - | $ 308,711 |

| | | |
|---|---|---|
| Total Standardized Professional and Product Fees | $ 4,536,766 | $ 25,317,327 |

Figure 22-B
Detail of Differences Reports – Financial (continued)

| PASS-THROUGH EXPENSES REPORT | | |
|---|---:|---:|
| EDC | - | - |
| Investigator Meetings | 239,100 | 203,960 |
| Investigator Fees | TBD | - |
| Monitor Travel | TBD | 3,616,152 |
| Travel to Training Meetings | - | - |
| Travel to Client Meetings | - | 63,257 |
| Travel for Audit Visits | - | - |
| Drug | 87,300 | 224,489 |
| Shipping, Printing and others | - | 326,624 |
| Diagnostics | 76,350 | - |
| Translation | - | 12,652 |
| LABS | - | - |
| ECG | - | - |
| Estimated Total Pass-Through Costs | $ 402,750 | $ 4,447,134 |

| Total Project Budget Per LOAACs | $ 4,939,516 | $ 29,764,461 |
|---|---:|---:|

Figure 23
Normalized Comparator Information of LOAACs Reports

This report classifies costs and numbers of activities into buckets such as 'cost per patient', 'cost per site', 'cost per page', 'cost per month', and 'cost per monitoring visit'. This is an important guideline for watching for overruns, and points for further discussion. Also note monitoring intervals.

| SUMMARY REPORT | CRO 2 | CRO 4 | RFP Equalizer |
|---|---|---|---|
| Sub - Total Project Budget per LOAACs Submitted (Including Pass Throughs) | $ 4,939,516 | $ 29,764,461 | |
| Total Project Duration | 35.0 | 33.0 | 35.0 |
| Patients Completed | 300 | 300 | 300 |
| Professional Fees per Patient | $ 16,465 | $ 99,215 | |
| Number of Sites | 150 | 185 | 150 |
| Professional Fees per Site | $ 32,930 | $ 160,889 | |

| START UP, REGULATORY & SITE MANAGEMENT | | | |
|---|---|---|---|
| Total Startup Costs | $ 708,206 | $ 3,747,037 | |
| Number of Sites | 150 | 185 | 150 |
| Startup Costs per Site | $ 4,721 | $ 20,254 | |
| Monitoring Pass Through Costs per Visit | TBD | 807 | |

| PROJECT MANAGEMENT | | | |
|---|---|---|---|
| Total Project Management Cost | $ 1,361,724 | $ 7,853,157 | |
| Number of Sites | 150 | 185 | 150 |
| Project Management Cost per Site | $ 9,078 | $ 42,449 | |
| Project Duration (in months) | 35 | 33 | 35 |
| Project Management Cost per Month | $ 38,906 | $ 237,974 | |
| Hours Project Management spends with site per month | 1 | 6 | |

| DATA MANAGEMENT | | | |
|---|---|---|---|
| Total Data Management Costs | $ 614,336 | $ 1,141,651 | |
| Total CRF Pages | 62,700 | 37,500 | 62,700 |
| Data Management Cost per CRF page | $ 10 | $ 30 | |

Report of Hardware

Figure 25-A1

B. Summary of Supplier Differences Report and Analysis

This report is an over-arching comparison of differences in assumptions, standardized professional fees, pass-through expenses, missing costs, all inclusive costs and finally the total budget

| Overall Assumptions | |
|---|---|
| Number of Sites | Key Variances >> |
| Total Project Duration (Months) | |
| Total CRF Pages | Key Variances >> |
| Total Number of Queries | |
| Total Number of Edit Checks | |
| AE's per Patient | |
| SAE Reconciliation | |
| Tables | |
| Total Monitoring Visits | Key Variances >> |

Standardized Professional Fees
List of Activities and Associated Costs (LOAACs) SUMMARY

|   |
|---|
| Total Standardized Professional Fees |
| Total Products Fees |
| Estimated Total Pass-Through Expenses |
| Sub - Total Project Budget per LOAACs Submitted |
| *(Not all inclusive)* |

| Check Calculation (USE INTERNAL ONLY) |
|---|
| Total Standardized Professional Fees |
| Total Products Fees |
| Estimated Total Pass-Through Expenses |
| Sub - Total Project Budget per LOAACs Submitted |

Adjustments to equalize specifications, add what is missing, and include necessary work

|   |
|---|
| Equalized Costs, missing or over spec |
| Total with Missing Items added |
| Items on which CROs are 'silent' and which result in an average 30% overrun |
| Necessary Costs Now Included |

Solution 1

|   |
|---|
| Total Projected Budget Equalized to XXX Sites |

Solution 2

|   |
|---|
| Total Projected Budget Equalized to XXX Sites |

*See the Commentary (section A) for definition of terms*

Figure 25 – A2

| ='LOAACS Standardization'!I130 | ='LOAACS Standardization'!J130 |
|---|---|
| ='LOAACS Standardization'!I132 | ='LOAACS Standardization'!J132 |
| ='LOAACS Standardization'!I141 | ='LOAACS Standardization'!J141 |
| ='LOAACS Standardization'!I157 | ='LOAACS Standardization'!J157 |
| ='LOAACS Standardization'!I158 | ='LOAACS Standardization'!J158 |
| ='LOAACS Standardization'!I165 | ='LOAACS Standardization'!J165 |
| ='LOAACS Standardization'!I162 | ='LOAACS Standardization'!J162 |
| ='LOAACS Standardization'!I164 | ='LOAACS Standardization'!J164 |
| ='LOAACS Standardization'!I171 | ='LOAACS Standardization'!J171 |
| ='LOAACS Standardization'!I152 | ='LOAACS Standardization'!J152 |

| ='LOAACS Standardization'!I190 | ='LOAACS Standardization'!J190 |
|---|---|
| =IF(SUM('LOAACS Standardization'!I193:I204)=0,"Not Included",SUM('LOAACS Standardization'!I193:I204)) | =IF(SUM('LOAACS Standardization'!J193:J204)=0,"Not Included",SUM('LOAACS Standardization'!J193:J204)) |
| ='LOAACS Standardization'!I226 | ='LOAACS Standardization'!J226 |
| =SUM(F17:F19) | =SUM(G17:G19) |

| =IF(F17-'LOAACS Standardization'!I190<>0,"ERROR"," ") | =IF(G17-'LOAACS Standardization'!J190<>0,"ERROR"," ") |
|---|---|
| =IF(F18='LOAACS Standardization'!I205,"","ERROR") | =IF(G18='LOAACS Standardization'!J205,"","ERROR") |
| =IF(F19-'LOAACS Standardization'!I226<>0,"ERROR"," ") | =IF(G19-'LOAACS Standardization'!J226<>0,"ERROR"," ") |
| =IF(F20-'LOAACS Standardization'!I228<>0,"ERROR"," ") | =IF(G20-'LOAACS Standardization'!J228<>0,"ERROR"," ") |

| =F32+F20 | =G32+G20 |
|---|---|

| =F33+F35 | =G33+G35 |
|---|---|

|   |   |
|---|---|

Figure 25-B1

B. Analysis Summary of Supplier Cost Differences Report

A high-level comparison of major assumptions, and the associated professional fees and passthrough costs

| Overall Assumptions |
|---|
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |

| Professional Fees and Numoda Portal and Tool Fees |
|---|
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |

Total Professional Fees and Numoda Portal and Tool Fees

| Pass Through Costs |
|---|
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |

Pass Through Cost

Total Project Fees and Cost

Figure 25- B2

| ='LOAACS Standardization'!#REF! | ='LOAACS Standardization'!#REF! |
|---|---|
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |

| ='LOAACS Standardization'!#REF! | ='LOAACS Standardization'!#REF! |
|---|---|
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| =SUM(F61:F73) | =SUM(G61:G73) |

| ='LOAACS Standardization'!#REF! | ='LOAACS Standardization'!#REF! |
|---|---|
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| =SUM(F77:F94) | =SUM(G77:G94) |

=F95+F74
=IF(F97-F200<>0,"ERROR"," ")

=G95+G74
=IF(G97-G200<>0,"ERROR"," ")

Figure 25-C1

C. Detail Of Differences Report - Metrics
Comparison of major assumptions, and the associated professional fees and passthrough costs, in detail

| Overall Assumptions |
|---|
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |

| PM Assumptions |
|---|
| ='LOAACS Standardization'!#REF! |
| ='LOAACS Standardization'!#REF! |

| Monitoring Assumptions |
|---|
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |

| Data Management Assumptions |
|---|
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |

| Biostats Assumptions |
|---|
| ='LOAACS Standardization'!#REF! |
| ='LOAACS Standardization'!#REF! |
| ='LOAACS Standardization'!#REF! |

| Safety |
|---|
| ='LOAACS Standardization'!#REF! |
| ='LOAACS Standardization'!#REF! |

Figure 25-C2

| | |
|---|---|
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |

| | |
|---|---|
| ='LOAACS Standardization'!#REF! | ='LOAACS Standardization'!#REF! |
| ='LOAACS Standardization'!#REF! | ='LOAACS Standardization'!#REF! |

| | |
|---|---|
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |

| | |
|---|---|
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |

| | |
|---|---|
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |

| | |
|---|---|
| ='LOAACS Standardization'!#REF! | ='LOAACS Standardization'!#REF! |
| ='LOAACS Standardization'!#REF! | ='LOAACS Standardization'!#REF! |

Figure 25-D1

C. Detail Of Differences Report - Financial
Comparison of major assumptions, and the associated professional fees and passthrough costs, in detail

| PROFESSIONAL FEES |
|---|
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| SubTotal Professional Fees |

| TOOLS AND SYSTEMS |
|---|
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| SubTotal Tools and Systems |

TOTAL PROFESSIONAL AND SYSTEM FEES

| PASS THROUGH EXPENSES |
|---|
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| ='LOAACS Standardization'!#REF! |
| TOTAL PASS THROUGH EXPENSES |

| TOTAL PROJECT FEES |
|---|

Figure 25-D2

| ='LOAACS Standardization'!#REF! | ='LOAACS Standardization'!#REF! |
|---|---|
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| =SUM(F153:F158) | =SUM(G153:G158) |

| ='LOAACS Standardization'!#REF! | ='LOAACS Standardization'!#REF! |
|---|---|
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| =SUM(F161:F173) | =SUM(G161:G173) |

=SUM(F159+F174)  =SUM(G159+G174)

| ='LOAACS Standardization'!#REF! | ='LOAACS Standardization'!#REF! |
|---|---|
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| =SUM(F178:F197) | =SUM(G178:G197) |

| =F176+F198 | =G176+G198 |
|---|---|

=IF(F200-'LOAACS Standardization'!#REF!<>0,"EF

Figure 25-E1

D. Normalized Comparator Information

This is a report that was compiled by matching all activities (which were named differently in each proposal) into a unified list. This normalization is necessary for a thorough comparator analysis.

SUMMARY
- ='LOAACS Standardization'!#REF!
- ='LOAACS Standardization'!#REF!
- ='LOAACS Standardization'!#REF!
- Professional Fees per Patient
- ='LOAACS Standardization'!#REF!
- Standardized Professional Fees per Site

=UPPER(B153)
- Total Startup Costs
- ='LOAACS Standardization'!#REF!
- ='LOAACS Standardization'!#REF!
- Startup Costs per Site

=UPPER(B154)
- Total Monitoring Costs
- ='LOAACS Standardization'!#REF!
- Monitoring Costs per Visit

=UPPER(B155)
- Total Project Management Cost
- ='LOAACS Standardization'!#REF!
- ='LOAACS Standardization'!#REF!
- Project Management Cost per Site
- Project Duration (in months)
- Project Management Cost per Month

=UPPER(B156)
- Total Data Management Costs
- ='LOAACS Standardization'!#REF!
- Data Management Cost per CRF page

Figure 25-E2

| ='LOAACS Standardization'!#REF! | ='LOAACS Standardization'!#REF! |
|---|---|
| ='LOAACS Standardization'!#REF! | ='LOAACS Standardization'!#REF! |
| ='LOAACS Standardization'!#REF! | ='LOAACS Standardization'!#REF! |
| ='LOAACS Standardization'!#REF! | ='LOAACS Standardization'!#REF! |
| =+F206/F207/F208 | =+G206/G207/G208 |
| ='LOAACS Standardization'!#REF! | ='LOAACS Standardization'!#REF! |
| =+F206/F207/F210 | =+G206/G207/G210 |

| ='LOAACS Standardization'!#REF! | ='LOAACS Standardization'!#REF! |
|---|---|
| ='LOAACS Standardization'!#REF! | ='LOAACS Standardization'!#REF! |
| =+F214/F216/F215 | =+G214/G216/G215 |

| ='LOAACS Standardization'!#REF! | ='LOAACS Standardization'!#REF! |
|---|---|
| =+F220/F221 | =+G220/G221 |

| ='LOAACS Standardization'!#REF! | ='LOAACS Standardization'!#REF! |
|---|---|
| ='LOAACS Standardization'!#REF! | ='LOAACS Standardization'!#REF! |
| ='LOAACS Standardization'!#REF! | ='LOAACS Standardization'!#REF! |
| =+F225/F227/F226 | =+G225/G227/G226 |
| =F207 | =G207 |
| =+F225/F229 | =+G225/G229 |

| ='LOAACS Standardization'!#REF! | ='LOAACS Standardization'!#REF! |
|---|---|
| =+F233/F234 | =+G233/G234 |

Figure 25-F

| 1. Category Standardization Report | | | | | |
|---|---|---|---|---|---|
| CRO 2 | | =SUM(B33:G33) | | | |
| Professional Fees | | | | | |
| Start Up | Monitoring | PM | DM | Safety | Biostats |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| =SUM(B8:B32) | =SUM(C8:C32) | =SUM(D8:D32) | =SUM(E8:E32) | =SUM(F8:F32) | =SUM(G8:G32) |

| CRO 4 | | =SUM(B66:G66) | | | |
|---|---|---|---|---|---|
| Professional Fees | | | | | |
| Start Up | Monitoring | PM | DM | Safety | Biostats |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| 0 | 0 | 0 | 0 | 0 | 0 |
| =SUM(B41:B65) | =SUM(C41:C65) | =SUM(D41:D65) | =SUM(E41:E65) | =SUM(F41:F65) | =SUM(G41:G65) |

Figure 25-G1

2. Specifications/Assumptions Standardization Report

| | =B34 | =B97 |
|---|---|---|
| Overall Assumptions | | |
| Number of Sites | | |
| Patients Screened | | |
| Patients Enrolled | | |
| Patients Completed | | |
| Countries | | |
| Startup (Months) | | |
| Recruitment (Months) | | |
| Treatment (Months) | | |
| Closeout (Months) | | |
| Total Project Duration (Months) | =SUM(G137:G140) | =SUM(I137:I140) |
| Project Management Assumptions | | |
| Status Reports | | |
| Newsletters | | |
| Monitoring Assumptions | | |
| Qualification Visits | | |
| Initiation Visits | | |
| Interim Visits | | |
| Closeout Visits | | |
| Total Monitoring Visits | =SUM(G148:G151) | =SUM(I148:I151) |
| Data Management Assumptions | | |
| Total CRF Pages per Patient | | |
| Unique CRF Pages per Patient | | |
| Total CRF Pages | | |
| Total Number of Queries | | |
| Interim Analysis | | |
| Con Meds per Patient | | |
| Disease per Patient | | |
| AE's per Patient | | |
| Total Coded Terms | =SUM(G160:G162)*G134 | =SUM(I160:I162)*I134 |
| SAE Reconciliation | | |
| Total Number of Edit Checks | | |
| Lab Transfer | | |
| Diary Transfer | | |
| Databases to be Reconciled - Integrated | | |
| Biostats Assumptions | | |
| Tables | | |
| Listings | | |
| Figures | | |
| Safety | | |
| SAE's | | |
| Safety Database | | |

Figure 25-G2

3. Financial Standardization Report

| | =B34 | | =B97 | |
|---|---|---|---|---|
| Standardized Professional Fees | | | | |
| Start Up, Regulatory & Site Management | =+B63 | | =+B126 | |
| Monitoring | =+C63 | | =+C126 | |
| Project Management | =+D63 | | =+D126 | |
| Data Management | =+E63 | | =+E126 | |
| Safety, Medical & Scientific Services | =+F63 | | =+F126 | |
| Biostatistics & Medical Writing | =+G63 | | =+G126 | |
| | =SUM(G184:G189) | | =SUM(I184:I189) | |
| | =IF(SUM(G184:G189)-D34<>0,"ERROR"," ") | | =IF(SUM(I184:I189)-D97<>0,"ERR | |
| Products | | | | |
| Screening and Enrollment System | | Not Included | | Not Included |
| Site Compliance Tools (EDC Included Free) | | Not Included | | Not Included |
| Integrated, Web-Based Monitoring System (with Centralized Trip Reports) | | Not Included | | Not Included |
| Real Time Reporting Tools (with Document Management System) | | Not Included | | Not Included |
| Single Portal Connecting to Interoperable Neural Network | | Not Included | | Not Included |
| All Custom Complete Integration and Interoperability | | Not Included | | Not Included |
| Ongoing Consolidation and Reconciliation | | Not Included | | Not Included |
| Early Safety Signal Detection System | | Not Included | | Not Included |
| Interoperable System for Supplies and Re-Supply Logistics Management | | Not Included | | Not Included |
| Clinical Project Accounting System | | Not Included | | Not Included |
| IVRS | | | | |
| IVRS Diary Activities | | | | |
| | =IF(SUM(G193:G204)=0,"Not Included",SUM("LOAACS St | | =IF(SUM(I193:I204)=0,"Not Included",SI | |
| Pass-Through Expenses | | | | |
| EDC | | | | |
| Investigator Fees | | | | |
| Investigator Meeting Organization | | | | |
| Investigator Meeting Travel | | | | |
| Monitor Travel | | | | |
| Travel to Training Meetings | | | | |
| Travel to Client Meetings | | | | |
| Travel for Audit Visits | | | | |
| Meetings and Teleconferences | | | | |
| IVRS Expenses | | | | |
| Printing, Shipping and Other | | | | |
| Regulatory and EC Fees | | | | |
| Translation | | | | |
| Lab Fees | | | | |
| Drug Supply | | | | |
| ECG Fees | | | | |
| Advertising | | | | |
| Other | | | | |
| | =SUM(G208:G225) | | =SUM(I208:I225) | |
| Total Project Cost | =SUM(G190+SUM(G193:G204)+G226) | | =SUM(I190+SUM(I193:I204)+I226) | |

Figure 26
CPA/BAU Case Study

| | | | Numoda | Norm |
|---|---|---|---|---|

| Study 1 | Study with 20 sites | | | |
|---|---|---|---|---|
| | Original Cost | $5,808,693.00 | | |
| | NUMODA Final/Actual | $4,188,532.00 | | |
| | Cost Avoided | $1,620,107.00 | 28% Costs Avoided | Overrun |

| Study 2 | Study with 12 Sites | | | |
|---|---|---|---|---|
| | Original Cost | £1,055,082.00 | | |
| | NUMODA Final/Actual | £725,387.00 | | |
| | Cost Avoided | £329,695.00 | 31% Costs Avoided | Overrun |

| Study 3 | Study with 50 Sites | | | |
|---|---|---|---|---|
| | Original Cost | $3,733,000.00 | | |
| | NUMODA Final/Actual | $2,620,000.00 | | |
| | Cost Avoided | $1,113,000.00 | 30% Costs Avoided | Overrun |

Figure 27
**Numoda Business Analysis Unit
Financial Report**
To Provide: A Double-Blind, Randomized, Parallel,
Placebo-Controlled, Multicenter Study
Evaluating the Effect of
Protocol Number:
Prepared For:
Submitted by:   Numoda Corporation
601 Walnut Street, 9th Floor
Philadelphia, PA 19106
Phone: 215.238.8881
Fax:   215.238.9995

Figure 28
The Bottom Line

NUMODA

BOTTOM LINE

| | WITH NUMODA | WITHOUT NUMODA |
|---|---|---|
| Draft 1 Report Shell to Client | | |
| Draft 2 Report Shell to Client | | |
| Update Final Report Shell | | |
| Draft 2 Internal Senior Review of Final Report Shell | | |
| Draft 1 Internal Senior Review of Final Report Shell | | |
| Final Report Shell to Client | | |
| FINAL ANALYSIS | | |
| Evaluability Determinations (Includes Review with Client) | | |
| Blinded : Run Draft Tables | | |
| Request/Receive/Upload/Verify Unblinding Code | | |
| Unblinded: Update/Re-run Final tables | | |
| Run/Assess/Interpret Final Analyses | | |
| FINAL CLINICAL STATISTICAL REPORT | | |
| Incorporate Patient Narratives | | |
| Write Draft 1 Report | | |
| Internal Senior Review of Draft 1 Report | | |
| Draft 1 Report to client | | |
| Prepare Draft 2 Incorporating Sponsor changes | | |
| Draft 2 Report to client | | |
| Prepare Final Report Incorporating Sponsor Changes | | |
| Internal Senior of Final Report | | |
| Final report to client | | |
| Total Professional Fees | $ 2,440,433 | $ 2,862,828 |

TOTAL NUMODA INVESTMENT FOR THIS STUDY  $ 422,395

| | |
|---|---|
| Sites | 50 |
| Patients | 360 |
| Countries | 2 |
| Duration | 18 |
| CRF Pages | 51 |

Risk Analysis

Figure 30
Risk Matrix Calculation

NUMODA

RISK MATRIX CALCULATION

| Management Components | Length of Trial | Drug Supply Difficulty | Data Complexity | Monitoring for Compliance | Total Score |
|---|---|---|---|---|---|
| 272 sites, wide geographic dispersion | 2.5 years duration | Complex, only one year shelf life | Very ill patients | Complex to comply | 90% risk of significant delay or failure |
| 99 | 95 | 90 | 80 | 90 | 454 |

Legend and notes - Maximum risk is a score of 500
Risk of Significant Delay or Failure

| | |
|---|---|
| 1-100 | 25% |
| 100-200 | 33% |
| 200-300 | 50% |
| 300-400 | 75% |
| 400-500 | 90% |

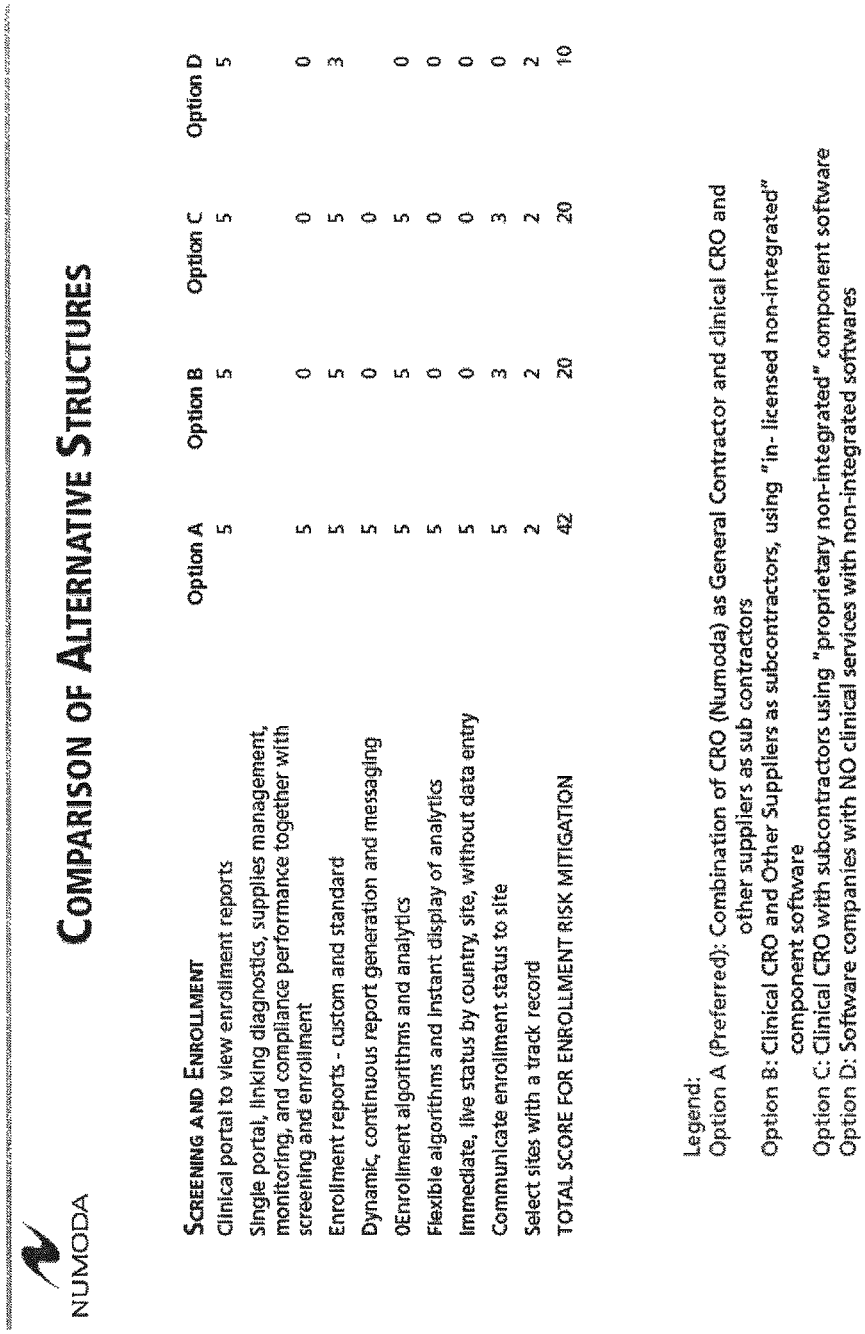

Figure 32

DETAIL OF DIFFERENCES - METRICS

| | CRO1 USA | CRO 1 USA/ZA | CRO 2 EDC | CRO 2 Paper |
|---|---|---|---|---|
| Overall Assumptions | | | | |
| Sites | 50 | 50 | 30 | 30 |
| Patients Screened | 720 | 720 | Not Detailed | Not Detailed |
| Patients Enrolled | 360 | 360 | 360 | 360 |
| Patients Completed | 360 | 360 | 338 | 338 |
| Countries | 1 | 2 | 1 | 1 |
| Startup (Months) | 5 | 5 | 2 | 2 |
| Recruitment (Months) | 8 | 6 | 4 | 4 |
| Treatment (Months) | 4 | 4 | 3 | 3 |
| Closeout (Months) | 4 | 4 | 3 | 2.5 |
| Total Project Duration (Months) | 20 | 18 | 12 | 11.5 |
| PM Assumptions | | | | |
| Status Reports | Not Detailed | Not Detailed | Not Detailed | Not Detailed |
| Newsletters | Not Detailed | Not Detailed | Not Detailed | Not Detailed |
| Monitoring Assumptions | | | | |
| Qualification Visits | Not Detailed | Not Detailed | 30 | 30 |
| Initiation Visits | Not Detailed | Not Detailed | 30 | 30 |
| Interim Visits | Not Detailed | Not Detailed | 300 | 150 |
| Closeout Visits | Not Detailed | Not Detailed | 30 | 30 |
| Total Monitoring Visits | 350 | 300 | 390 | 240 |
| Data Management Assumptions | | | | |
| Total CRF Pages per Patient | Not Detailed | Not Detailed | 51 | 51 |
| Unique CRF Pages per Patient | Not Detailed | Not Detailed | 22 | 22 |
| Total CRF Pages | Not Detailed | Not Detailed | 42,120 | 18,360 |
| Total Number of Queries | Not Detailed | Not Detailed | 42,120 | Not Detailed |
| Interim Analysis | Not Detailed | Not Detailed | Not Detailed | Not Detailed |
| Con Meds per Patient | Not Detailed | Not Detailed | Not Detailed | Not Detailed |
| Disease per Patient | Not Detailed | Not Detailed | Not Detailed | Not Detailed |
| AE's per Patient | Not Detailed | Not Detailed | Not Detailed | Not Detailed |
| SAE Reconciliation | Not Detailed | Not Detailed | Not Detailed | Not Detailed |
| Total Number of Edit Checks | Not Detailed | Not Detailed | Not Detailed | Not Detailed |
| Lab Transfer | Not Detailed | Not Detailed | Not Detailed | Not Detailed |
| Diary Transfer | Not Detailed | Not Detailed | Not Detailed | Not Detailed |
| Biostats Assumptions | | | | |
| Tables | Not Detailed | Not Detailed | 35 | 35 |
| Listings | Not Detailed | Not Detailed | 25 | 25 |
| Figures | Not Detailed | Not Detailed | 5 | 5 |

Figure 33

DETAIL OF DIFFERENCES - FINANCIAL

| | CRO1 USA | CRO 1 USA/ZA | CRO 2 EDC | CRO 2 Paper |
|---|---|---|---|---|
| FINANCIAL SUMMARY | | | | |
| START UP, REGULATORY & SITE MANAGEMENT ACTIVITIES | $ 312,500 | $ 343,500 | $ 280,033 | $ 266,432 |
| MONITORING ACTIVITIES | 1,179,000 | 1,054,000 | 454,740 | 599,343 |
| PROJECT MANAGEMENT ACTIVITIES | 300,000 | 350,00 | 205,453 | 222,006 |
| DATA MANAGEMENT ACTIVITIES | 462,280 | 464,280 | 192,514 | 448,987 |
| SAFETY, MEDICAL & SCIENTIFIC SERVICES ACTIVITIES | 48,000 | 48,000 | 92,568 | 92,642 |
| BIOSTATISTICS & MEDICAL WRITING ACTIVITIES | 180,000 | 180,000 | 135,790 | 136,159 |
| SUBTOTAL PROFESSIONAL FEES | 2,483,780 | 2,439,780 | 1,311,098 | 1,765,560 |
| IVRS SYSTEM RANDOMIZATION | 44,048 | 44,048 | Included | 69,425 |
| Diary | 135,000 | 135,000 | 460,015 | None |
| SUBTOTAL IVRS FEES | 179,048 | 179,048 | 460,015 | 69,425 |
| Screening, Enrollment Tools and Reporting Tools | Not included | Not included | Not Included | Not Included |
| Site Compliance Tools and Reporting Tools | Not included | Not included | Not Included | Not Included |
| Monitoring System and Reporting Tools | Not included | Not included | Not Included | Not Included |
| Single Portal connecting to Interoperable Neural Network | Not included | Not included | Not Included | Not Included |
| All Custom Complete Integration and Interoperability through a Neural Network | Not Included | Not Included | Not Included | Not Included |
| Ongoing Consolidation and Reconciliation | Not Included | Not Included | Not Included | Not Included |
| Early Safety Signal Detection System | Not Included | Not Included | Not Included | Not Included |
| Interoperable System for Supplies and Re-supply logistics Management | Not Included | Not Included | Not Included | Not Included |
| SUBTOTAL SYSTEMS, PORTAL, INEGERATIONS, REPORTING TOOLS AND TOOLS | Not Included | Not Included | Not Included | Not Included |
| | | | | |
| TOTAL PROFESSIONAL FEES | $ 2,662,828 | $ 2,618,828 | $ 1,821,113 | $ 1,834,985 |
| Drug | 90,091 | 90,091 | 31,950 | 31,950 |
| Lab | 135,000 | 155,000 | 57,319 | 57,319 |
| Advertisment | 175,000 | 157,500 | 60,000 | 60,000 |
| Monitoring travel | 360,000 | 320,000 | 180,000 | 214,500 |
| Investigator Meeting travel | 220,000 | 220,000 | 121,500 | 121,500 |
| Investigator Fees | 2,229,840 | 2,108,502 | 3,186,000 | 3,186,000 |
| IRB Costs | Not Detailed | Not Detailed | 60,000 | 60,000 |
| Other Passthroughs | 92,427 | 91,427 | NONE | 30,060 |
| EDC | NONE | NONE | 149,562 | NONE |
| SUBTOTAL PASS THROUGH FEES | $ 3,302,358 | $ 3,142,520 | $ 3,846,295 | $ 3,302,358 |
| | | | | |
| TOTAL PROJECT BUDGET | $ 5,965,186 | $ 5,761,348 | $ 5,667,408 | $ 5,596,314 |

Figure 34

NUMODA

COMMENTARY ON THE COMPARISON

The following includes some commentary based on the benchmark financials.

ENROLLMENT

It would be worth investing in the minimal cost (see the summary) of systems and tools for enrollment for this study, since enrollment will be a challenge with the study's particular inclusion/exclusion criteria. For the cost you see listed, systems and tools would be implemented at the site level (screening and enrollment and compliance tools) and at the team level (reporting tools), giving complete coverage for identifying the correct patients speedily, tracking enrollment, and rapid identification of problems. In addition, these tools help identify the need to adapt the trial, and they have the flexibility to change (in hours to days) in order to accommodate an identified adaptive approach.

CLINICAL MONITORING

Benchmarking metrics have revealed that sponsors spend a lot of time and money and use many clinical resources to analyze reports from the multiple suppliers. For the price listed in the financial summary, Numoda will consolidate those reports, reconcile any missing information, and display information in a way that will be extremely useful to all suppliers, groups and participants. One example of this occurred, where a sponsor was saved from reconciling the diagnostic reports of three different labs – not too dissimilar to the multiple data sources and points that that you are facing. The Numoda portal provided the necessary analytics that saved a virologist four to six hours a day in analysis prep work.

The Numoda services will also provide the data reconciliation work that needs to be done at the end of the study. Benchmarking metrics show that CROs are 'silent' on the responsibility of reconciling the multiple databases from separate suppliers, because the work is extremely difficult to do, time consuming and costly. Numoda is able to perform this work very cost effectively, freeing the internal sponsor group from this work's burden and significantly shortening the time to data lock.

PROJECT MANAGEMENT

We also save suppliers significant time in this area. As much as thirty percent of supplier employees' time is spent in data entering information for tracking their work completed to submit billing metrics data to their superiors – and this is time they are not spending on your behalf. For another client we saved 25% of their total time by taking over project accounting and billing verification activities – and they got much more accurate project accounting. This project accounting is essential for orchestrating a successful clinical trial and managing the budget. Even though you hire a global project manager, the time spent doing this project accounting, prevents them from focusing on enrollment.

Figure 35

NORMALIZED COMPARATOR INFORMATION

NUMODA

| | CRO 1 US Only | CRO 2 USA/ZA | CRO2 EDC | CRO2 Paper |
|---|---|---|---|---|
| Summary Metrics | | | | |
| Total Professional Fee | 2,483,780 | 2,439,780 | 1,361,098 | 1,765,560 |
| IVRS/EDC Technology | 44,048 | 44,048 | 149,526 | 69,425 |
| Diary | 135,000 | 135,000 | 460,015 | |
| Adjusted total to Include IVRS and Diary | 2,662,828 | 2,618,828 | 1,970,639 | 1,834,985 |
| Number of Sites | 50 | 50 | 30 | 30 |
| Total Professional Fee Per Site | 53,257 | 52,377 | 65,688 | 61,166 |
| Startup, Regulatory and Site Management Activities | | | | |
| Startup, Regulatory and Site Management Activities | 312,500 | 343,500 | 280,033 | 266,423 |
| Sites | 50 | 50 | 30 | 30 |
| Cost per Site Enrolled | 6,250 | 6,870 | 9,334 | 8,881 |
| Monitoring | | | | |
| Total Monitoring Cost | 1,179,000 | 1,054,000 | 454,740 | 599,343 |
| Monitoring Visits | 350 | 300 | 240 | 390 |
| Gross Monitoring Cost per Visit | 3,369 | 3,513 | 1,895 | 1,537 |
| Monitoring Travel Cost | 360,000 | 320,000 | 180,000 | 214,500 |
| Monitoring Travel Cost per Visit | 1,029 | 1,067 | 750 | 550 |
| Project Management | | | | |
| Project Management | 300,000 | 350,000 | 205,453 | 222,006 |
| Cost Per Site | 6,000 | 7,000 | 6,848 | 7,400 |
| Study Duration (Months) | 20 | 18 | 12 | 11.5 |
| Project Management cost per month | 15,000 | 19,444 | 17,121 | 19,305 |
| Investigator Meeting Travel | 220,000 | 220,000 | 121,500 | 121,500 |
| Investigator Meeting Travel Cost per Site | 4,400 | 4,400 | 4,050 | 4,050 |
| Data Management / IVRS / Diary / EDC | | | | |
| Total DM | 464,280 | 454,280 | 192,514 | 464,987 |
| IVRS/EDC Technology | 44,048 | 44,048 | 149,526 | 69,425 |
| Diary | 135,000 | 135,000 | 460,015 | |
| Total Data Management / IVRS / Diary / EDC | 643,328 | 633,328 | 802,055 | 518,412 |
| Patients | 360 | 360 | 360 | 360 |
| Data Management Cost Per Patient | 1,787 | 1,759 | 2,228 | 1,440 |

Figure 36

BUSINESS ANALYSIS UNIT'S FINANCIAL SUMMARY

| NUMODA | NUMODA SYSTEMS & Clinical Services | CRO1 | Other Contractors (EST) | NUMODA General Contractor |
|---|---|---|---|---|
| NECESSARY PRODUCTS AND SERVICES FOR TRIAL SUCCESS | | | | |
| Professional Fees | | | | |
| START UP, REGULATORY & SITE MANAGEMENT ACTIVITIES | | 281,250 | | 281,250 |
| MONITORING ACTIVITIES | | 884,250 | | 884,250 |
| PROJECT MANAGEMENT ACTIVITIES | 210,000 | | | 210,000 |
| DATA MANAGEMENT ACTIVITIES | 450,456 | | | 450,456 |
| SAFETY, MEDICAL & SCIENTIFIC SERVICES ACTIVITIES | 36,000 | | | 36,000 |
| BIOSTATISTICS & MEDICAL WRITING ACTIVITIES | | 180,000 | | 180,000 |
| IVRS SYSTEM - RANDOMIZATION | 81,761 | | | 81,761 |
| DIARY | 87,919 | | | 87,919 |
| SUBTOTAL PROFESSIONAL FEES | 696,456 | 1,345,500 | | 2,211,636 |
| Screening and Enrollment Tools | 8,766 | | | 8,766 |
| Site Compliance Tools (EDC Included Free) | 15,320 | | | 15,320 |
| Integrated, Web-Based Monitoring System (with Centralized Trip Reports) | 29,218 | | | 29,218 |
| Real Time Reporting Tools (with Document Management System) | 20,453 | | | 20,453 |
| Integrated Portal Connecting to a Neural Network of Suppliers | 78,600 | | | 78,800 |
| All Custom Complete Integration and Interoperability | 25,200 | | | 25,200 |
| Ongoing Consolidation and Reconciliation | 22,440 | | | 22,440 |
| Early Safety Signal Detection System | 19,000 | | | 19,000 |
| Interoperable System For Supplies and Re-Supply Logistic Management | 9,800 | | | 9,800 |
| SUBTOTAL NUMODA SYSTEMS, PORTAL INTEGRATIONS, REPORTING TOOLS | 228,797 | | | 228,797 |
| TOTAL PROFESSIONAL FEES | 925,253 | 1,345,500 | | 2,440,433 |
| Value Added Supplies Items | | | | |
| Drug | | | 90,091 | 90,091 |
| Lab | | | 155,000 | 155,000 |
| Advertisement | | | 157,500 | 157,500 |
| Monitoring Travel | | 320,000 | | 320,000 |
| Investigator Meeting Travel | 5,000 | 215,000 | | 220,000 |
| Investigator Fees | 2,108,502 | | | 2,108,502 |
| IRB Costs | | 60,000 | | 60,000 |
| Other Passthroughs | 15,000 | | 76,427 | 91,427 |
| EDC | INCLUDED | | | INCLUDED |
| TOTAL ESTIMATED PASS THROUGH COSTS | 2,128,502 | 595,000 | 479,018 | 3,202,520 |
| TOTAL PROJECT FEES | 3,053,755 | 1,940,500 | 479,018 | 5,642,953 |

METHOD AND ARTICLE OF MANUFACTURE FOR PERFORMING CLINICAL TRIAL BUDGET ANALYSIS

CROSS-REFERENCE TO RELATED APPLICATIONS

This application is a continuation of copending U.S. application Ser. No. 12/121,822 filed May 16, 2008, which is incorporated by reference herein.

This application claims the benefit of U.S. Provisional Application No. 60/939,059 filed May 19, 2007 entitled "Clinical Trial Budget Analysis."

BACKGROUND OF THE INVENTION

1. Field of the Invention

This invention relates generally to the analysis of clinical trial budgets. More particularly, this invention relates to a computer-implemented method for analyzing budgets for clinical trials.

2. Background

The life sciences industry includes pharmaceutical and biotechnology companies that are required to perform various phases of clinical trials (also referred to as clinical studies) on new drugs, compounds and medical devices before they can obtain marketing approval from the U.S. Food and Drug Administration or a foreign counterpart. Clinical trials are expensive to conduct and require effective budgeting processes in order to keep costs under control and obtain the best return on investment. The budgeting process for conducting a clinical trial is complex since is often requires the pharmaceutical or biotechnology company, known as the "sponsor" of the trial, to use many different vendor suppliers in addition to its own resources. The process used to select between potential vendor suppliers can profoundly affect a sponsor's clinical trial budget since vendor suppliers can price the same services in significantly different ways and amounts, and the budgeting processes currently used by sponsors cannot identify these pricing differences without significant time and expense as is described below in greater detail.

FIG. 1 illustrates the following example of the flow of budget information into a biotechnology company, which is not intended to be limiting in any way. Several different lists of activities and associated costs (LOAACS) shown on FIG. 1 contain many itemized activities and costs that are proposed in order to complete a clinical trial under a set of specification assumptions. According to an embodiment of the invention, this set of specification assumptions include number of sites, number of patients, number of countries, and the like, that are estimated to be necessary to complete a specific clinical trial. A vendor supplier (a Contract Research Organization or CRO for this example) or an in-house team is given a set of assumption specifications with a list of requested activities by the biotechnology company in the form of a document called a "Request for Proposal" (RFP). The RFP sets forth the specification assumptions and the list of requested activities from which a responder must prepare a budget containing the costs for the activities under the specification assumptions. CROs respond to an RFP in their own standard format and send a number of standard and non-standard documents to the biotechnology company, which is then responsible for analysis of the budget information to properly cost and then perform a clinical trial.

A "budget" as described herein, may be an internal project budget or a bid for outsourced work.

Although the biotechnology company carefully designs the RFP and the CROs or in-house teams might carefully prepare the RFP responses, it is very difficult and time consuming to analyze the budgets provided. This happens because of many different reasons: many activities are necessary to conduct a trial including teleconferences, training, meeting time, and the like; there is no standard terminology; there are no standard categorizations for these activities. For example, one person preparing a budget might use the term "teleconference" for a training session because that is the way the training is conducted, while another person reserves the term "teleconference" for weekly meetings conducted on the telephone. To further add to the confusion, the categories for these activities are not standardized. For example, one person analyzing a budget might classify the "teleconference-training" activity under the category "initial study set up," while another person will categorize the same activity under the category of "monitoring" because the training is being done for the monitors who will monitor the trial. As there are hundreds of activities and multiple categories, confusion and misunderstandings can quickly multiply.

Similar budget process problems can and do occur within a pharmaceutical company or other companies in the life sciences industry. While this example shows the flow of information in the industry to obtain budget proposals from vendor suppliers such as Contract Research Organizations (CROs), a similar process is used to formulate budgets for other types of vendor suppliers and for in-house resources. Again, a similar process is used if a combination of in-house and vendor resources are used.

In order to try to reduce the confusion, some biotechnology and pharmaceutical companies write detailed RFPs, which provide standard categories and standard terms for activities. Persons who prepare budgets are asked to provide detailed information for the budget within the RFP. A goal of this is to make the analysis process simpler, so that the budgets can be compared, contrasted, and costs understood easily if there is a change in any of the assumption specifications. However, completing and comparing budgets within an RFP has not solved the problem. The reasons that confusion and errors still exist are due to many factors including the following factors:

1. No benchmark libraries of standard terms, costs, categories, activities are easily available.
2. There are few staff that have the detailed financial and operational expertise to do a proper analysis.
3. There are little or no performance metrics linked to cost metrics.
4. Teams and supplier vendors may unintentionally or purposefully leave gaps in the lists of activities needed to complete a clinical trial.
5. Supplier vendors are unable to conform their internal costing, pricing and budgeting to the many different RFPs that their clients expect them to complete.

Unfortunately, the result of the confusion surrounding the analysis of budgets is that the biotechnology companies and others managing the budgets cannot, for example, make accurate pricing comparisons or compile accurate budgets. These mistakes cause a biotechnology company to pay more than is necessary for some activities. Another problem is that budget overruns are high due to gaps in activities that have not been budgeted. In addition, with the lack of proper budget analysis, the clinical trial often suffers from poor performance, delays and failure.

SUMMARY OF THE INVENTION

The present invention overcomes the drawbacks of the prior art through a computer-implemented method of analyzing budgets for clinical trials. In one embodiment of the present invention, a person analyzing a budget for a clinical trial may accept the budget in any format, using any common terminology in the industry and any common categorization. The present invention may accept this information, process it through a series of steps, and produce reports that make the analysis simple and accurate. There is no limitation to the reports that can be produced by the present invention, and several examples are provided below. In one embodiment, the present invention organizes and analyzes the budgets using libraries of benchmark metrics for costs, terminology, categorization, and the like. Algorithms may take into account the complexity of the clinical trials, the therapeutic area (e.g., cardiology, neurology, and the like). Furthermore, the information can be analyzed according to phases of clinical development, adaptive trials, and the like, that are done in any country around the globe.

The present invention also provides a biotechnology company with an analysis, reports and recommendations for selecting a clinical research organization to conduct a clinical trial. Pharmaceutical and biotechnology companies can also attain an "apples to apples comparison" of budget options and supplier options.

The present invention may be used to assists companies that perform clinical trials in understanding what may be the most efficient and cost-effective way for running a given trial—whether it be using internal resources, or outsourcing, or a combination of both.

In one preferred embodiment, the present invention inputs one or more clinical trial budgets into a processor. The budget may include activities such as monitoring activities, data management activities, and biostatistical activities, and the like, that are conducted during clinical trials. The budgets may also include prices and costs associated with these activities. Costs can be analyzed in dollars, pounds, or any other currency.

In an embodiment of the present invention, reports are produced that compare and reference assumptions and their associated costs. These referenced assumptions may be contained in libraries of benchmarking information on cost metrics, service metrics, performance metrics, time to perform activities, standard terminology for activities, staffing rates, and the like. The reports may include a series of financial and operational analyses showing where the discrepancies are within any submitted vendor/supplier budgets or proposals, or within client's internal or resource plan.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

FIG. 2 shows a sample of reports provided in accordance with preferred embodiments of the present invention.

FIGS. 5A-5G, taken together, show the calculation of monitoring visits based on time (frequency of visits) according to a reference specification assumption in accordance with one preferred embodiment of the present invention.

FIGS. 9A-9P, taken together, is a request for proposal (RFP) provided by a biotechnology company.

FIGS. 10A-10B, taken together, show a response sent back to the biotechnology company by a particular Clinical Research Organization (CRO) in response to the RFP.

FIG. 11A-FIG. 11U shows the RFP response that was given to the biotechnology company by a CRO.

FIGS. 12A-12P, taken together, show a list of activities and associated costs that were given to the same biotechnology company by a different CRO FIGS. 13A-13EEE, taken together, show three sets of CRO responses.

FIG. 14 shows an excerpt from a CRO proposal that highlights a discrepancy in their proposal.

FIG. 15 shows a spreadsheet that relates to the discrepancy highlighted in FIG. 14.

FIGS. 16A-16B and 17-19 show spreadsheets related to RFP services.

FIGS. 20-21, 22A-22B and 23 show summary reports related to RFP's.

FIGS. 25A1-25G2, taken together, list algorithms and formulas used to calculate and produce reports.

FIG. 26 shows a summary report of a business analysis case study performed in accordance with a preferred embodiment of the present invention.

FIGS. 27-36 show a sample financial report associated with the business analysis case study.

DETAILED DESCRIPTION OF THE INVENTION

For purposes of explaining the present invention, specific embodiments will be described. These embodiments are exemplary only, and are not intended to limit the scope of the invention.

FIG. 2 shows a sample of reports provided by the present invention and demonstrates what the reports provide compared to the current process of analysis. Providing an easy way for companies to analyze budgets for conducting clinical trials has proven to play a large part in saving time and money, has taken the risk out of the clinical trial process, and has reduced the length of time needed to conduct a clinical trial.

Figure 1:
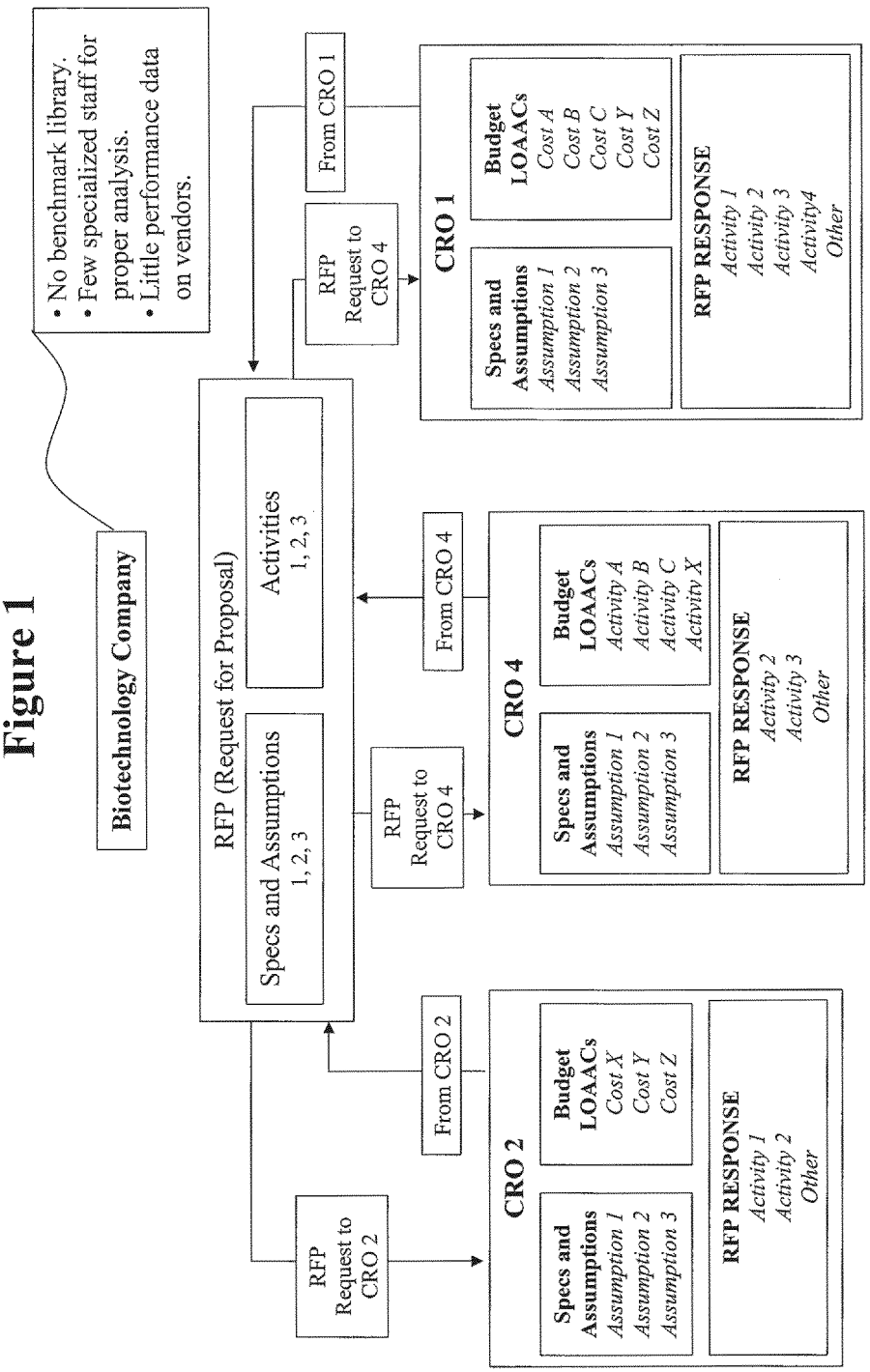
FIG. 1 shows an example of the flow of budget information into a biotechnology company for a clinical trial.
Figure 3:
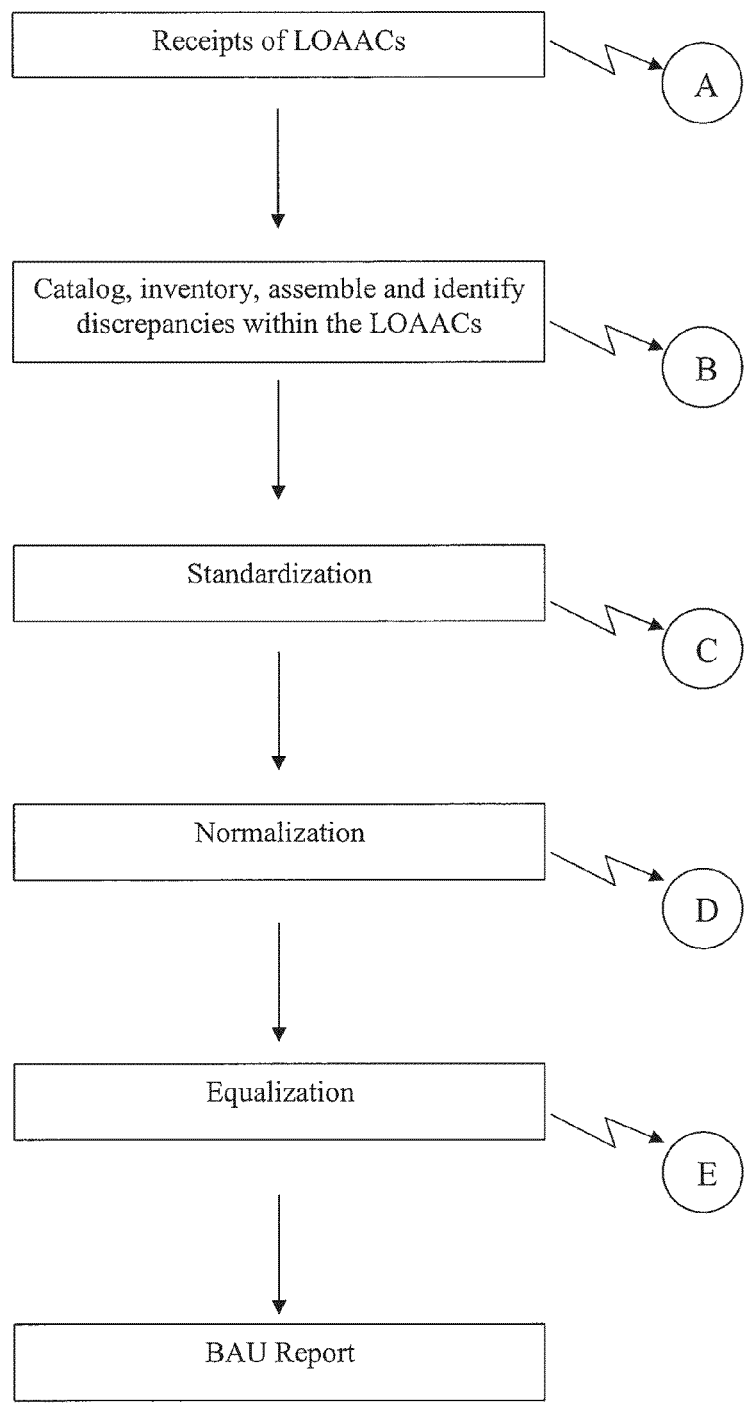
FIG. 3 is a flow diagram of the entire process that is performed by one preferred embodiment of the present invention.

FIG. 3 is a flow diagram of the entire process that is performed by an embodiment of the invention. This process occurs by inputting clinical trial budget information into a processor, including assumption specifications, activities and associated costs. As seen in FIG. 3, the data flow is as follows according to an embodiment of the invention: when the budget and information—LOAACs (Lists of Activities and Associated Costs), RFP, RFP responses, and any accompanying material that is part of the process are received, shown in A, they are inputted into the processor, shown in B. The many different ways for imputing such information into a processor are well known to those skilled in the art, including through a user interface, downloading from the web, importing an electronic files, scanning, and the like. In an example selected to illustrate an embodiment of the invention, FIGS. 9A-9P, taken together, is an RFP provided by a biotechnology company. As can be seen from this example, these RFPs are very detailed and exacting as to how the Biotechnology Company wants to see the responses returned. The RFP contains information about the trial. FIG. 9A shows the information about the trial protocol, such as the indication and objectives. FIG. 9B shows the timelines (dates). FIG. 9C-9F lists all of the assumption specifications. The RFP also provides a very specific structure for the activities and the cost of the activities as seen in FIG. 9G-9P. In the illustrated example, there five proposals were sent in against the RFP and three were used in this example. Lists of Activities and Associated Costs (LOAACS) are often sent instead of, or in conjunction with, the RFP response. FIG. 10A-10B shows the LOAACs (consisting of just two summary pages) that were sent back to the biotechnology company by Clinical Research Organization number 2 (CRO2) in response to the request for a proposal to conduct a specific clinical trial. FIG. 11A-FIG. 11U shows the RFP response that was given to the biotechnology company by CRO2 that were sent with the LOAACs. FIG. 11E line 1.1 shows how CRO2 has filled in one of the boxes on the RFP with dollar amounts, units, and the like.

FIGS. 12A-12P, taken together, show the LOAACs that were given to the same biotechnology company by a different Clinical Research Organization (CRO4) in response to the same request for a proposal to conduct the same clinical trial. The LOAACs from CRO4 contain much detailed information, which one would think would help the biotechnology company make a decision, however, it just makes the analysis and comparison more difficult. To add to the confusion, CRO4 provided a lot more information than requested and added other types of information that were not requested. For example, FIGS. 12A-12D show columns for the activities and assumption specifications for a 'one month follow-up', a 'six month follow-up', and a 'one year follow-up'. This information is entirely different than any of the CROs provided. FIGS. 12E-12P show the activities and costs, but do not exactly match the assumptions on the prior figure. Extra information, although it might seem to be useful, is often confusing and difficult to analyze and compare with other information. FIGS. 13A-13EEE, taken together, show three sets of CRO4 RFP responses, namely, FIGS. 13A-13S, FIGS. 13T-13LL, and FIGS. 13MM-13EEE. These sets of figures show three different RFP responses that correspond to the proposed 'one month follow-up', 'six month follow-up', and 'one year follow-up' scenarios proposed by CRO4. The most confusing aspect of these three responses is that, as can be seen on FIG. 13A, FIG. 13T and FIG. 13MM, the line for 'follow up period' shows as 6 months. However on FIG. 13E, the costs for item 1. Project Management is $140,499. This is the cost associated with the 6 months assumption specification shown on FIG. 13A. Yet in FIG. 13X, the costs for item 1. Project Management is $144,399. This cost is for the 6 months assumption specification shown on FIG. 13T. Yet again, FIG. 13QQ shows that the costs for item 1. Project Management is $148,149. This cost is for the 6 months assumption specification shown on FIG. 13MM. Preferred embodiments of the present invention identify such discrepancies.

The trial sponsor did not specifically request this information, but often a CRO includes other options and budgets from those requested. It is important to note that one of the important problems that the current embodiment of the invention solves, is that a non-clinical member of the biotechnology team has clinical data about the trial that is translated into understandable financial information to make a better decision. The clinical member of the team also gets financial information translated into clinical information, so it is easy for them to understand. This type of invention solves the problem that it is rare and costly to find clinical resources with financial backgrounds and financial resources with clinical problems.

Only two CROs are discussed in this example used to illustrate one of several possible embodiments of the invention. However, there is no limit to the amount or size of information that the present invention can analyze.

Standardization Process

Figure 4:
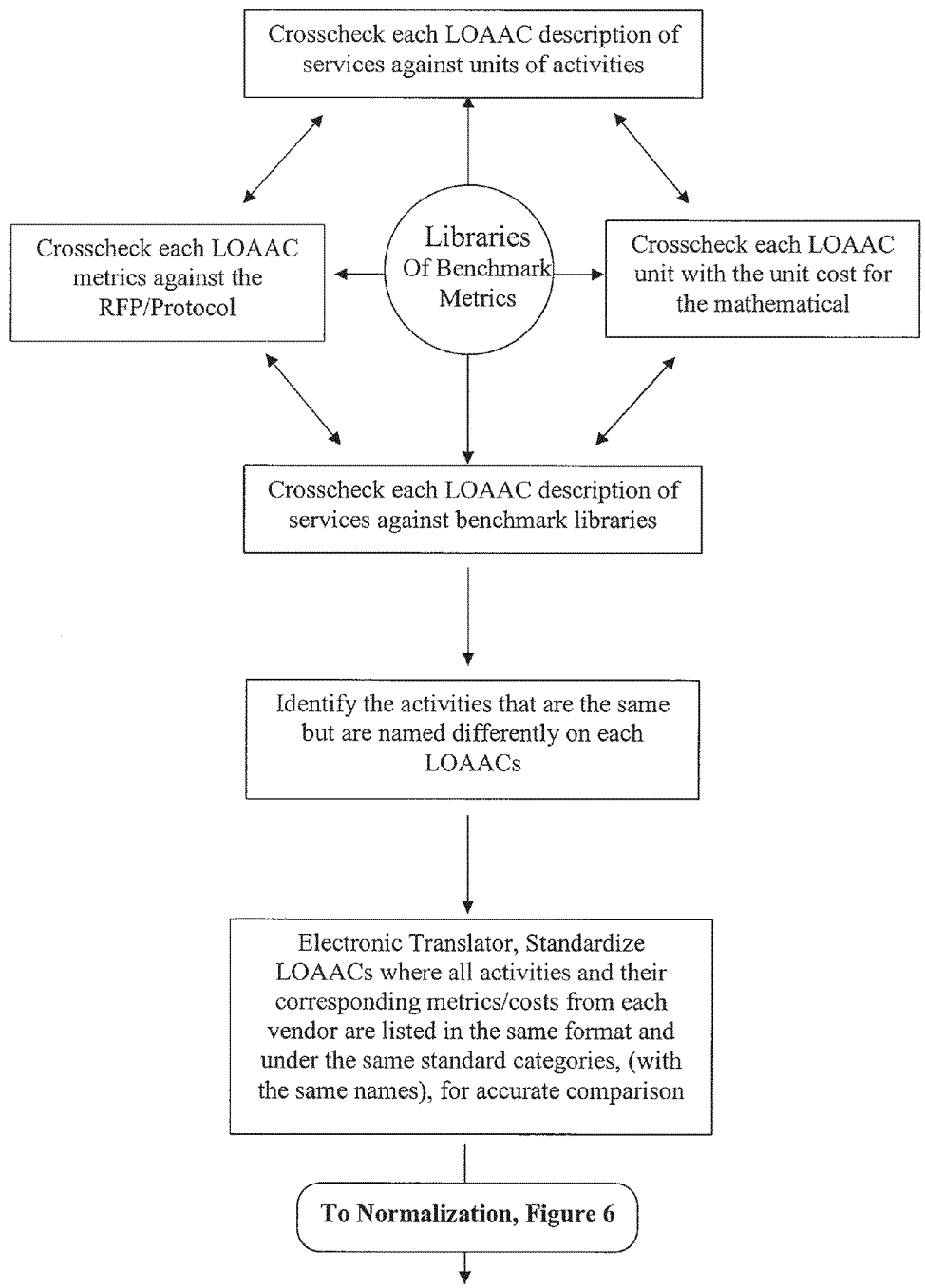
FIG. 4 illustrates a standardization process according to one preferred embodiment of the present invention.

Standardization is the process of classifying the activities into a set of standardized service categories. FIG. 4 illustrates the standardization process according to an embodiment of the invention, which can be done automatically, by the processor. This can be an important process because all of the accompanying materials received may be preferably reconciled and crosschecked, and discrepancies may be preferably logged into the libraries of benchmark metrics. The standardization process may preferably identify discrepancies within the materials (RFP response, LOAACs) sent to the biotechnology company. This may be done in an essentially "blinded" way so that bias is removed in the process. The LOAAC's description of services are crosschecked against the unit of activities, checked against the metric (assumption specification) in the RFP and the protocol and checked mathematically for accuracy in calculations of units and costs. The services that are named in the LOAACs are checked against the benchmark libraries of terminology. The next step identifies the activities that are named differently on each LOAAC, yet are actually the same activity. An electronic translator automatically performs some or all of the classification. The electronic translator includes a dictionary of activities and their associated standardized service categories so that it can then categorize all the services named on the LOAACs into standard categorizes, for comparison.

According to an embodiment of the invention, the process of inputting the clinical trial budget information into the processor may preferably include the cataloging, inventorying, and assembly of all materials that have been received, and then adding them to the libraries of benchmark metrics. The budget includes activities and associated costs.

An example of a discrepancy is illustrated in FIG. 14, which is an excerpt of the information sent to a biotechnology company by CRO1. Besides the RFP response and the LOAACs, CRO1, has included additional information in paragraph form, as seen in this FIG. 14. In paragraph C, the underlined sentence explains that CRO1 will provide the monitoring visit activities every six weeks. This is discrepant with what CRO1 has shown in their LOAACs related to monitoring visits on FIG. 15. On line 5.2.1, CRO1 is budgeting for 453 visits. These two pieces of information are contradictions, but not easy to spot, because they are in different forms. This embodiment of the invention will identify and display the discrepancies, as well as the correct number of monitoring visits needed for a clinical trial that has a specification assumption of 36 months for the trial timeline, and a specification assumption for frequency of monitoring visits at every six weeks. The correct number of monitoring visits would be 3,900 visits. The gap in the activity of monitoring visits is 3,447. This calculation is embedded in FIG. 5F in the line item called "Interim visits—paper CRFs" in row 36, with the formula shown in far right of column I.

FIGS. 5A-5G, taken together, show the calculation of monitoring visits based on time (frequency of visits) according to the reference specification assumptions (e.g., RFP from sponsor).

This embodiment of the invention discovers these errors without needing trained project staff and finance experts to dig deeply into three different documents and cross-reference all calculations, costs, activities and assumption specifications. Some of these steps in the process may be done simultaneously or, depending on the situation, skipped entirely, according to an embodiment of the invention.

According to an embodiment of the invention, FIG. 4 includes the steps that the processor makes in order to classify the activities into a set of standardized service categories such as "data management," "project management," "safety," and the processor allocating the associated activity costs with the respective standardized service category. An electronic translator can be used that references dictionaries of terms within the processor to match activities to the nearest similar term.

According to an embodiment of the invention, details regarding the units and costs for the trial's specification assumptions, as shown in a screen shot in FIGS. 16A and 16B, specification assumptions are inputted during the standardization process. FIG. 16A shows the first 40 lines and FIG. 16B shows the rest. The input may reflect the specification assumptions from the request for proposal from the biotechnology company, in this example. This step is done to generate within an embodiment of the invention, the benchmark specification assumptions and costs in standard categories of professional fees, as seen in FIG. 17 for CRO2 and in FIG. 18 for CRO4. The processor calculates the standardized activities together with their associated costs, based on the specification assumptions from the LOAACs from CRO2 and CRO4. The standardized items and their dollar amounts per standardized category are then generated according to an embodiment of the invention as shown in FIG. 19. This standardization process may include services and costs that are associated with the activities, sorted into the same standard categories. This may all be done based on libraries of activities terminology, libraries of category terminology, and libraries of cost and pricing methods that are used to compare and find common terms and categories, and the like. There is no limit to the libraries, and provisions can be made for continuous update of all libraries of benchmark metrics and algorithms used.

According to an embodiment of the invention, the standardization process may preferably complete crosschecks. These crosschecks may preferably compare each LOAAC against the RFP for a specific trial. Activities may be identified that are the same in meaning but are named differently in each LOAAC. At the end of this step, the new, standardized LOAACs may display all of the activities and the corresponding units and costs metrics itemized for CRO2 and CRO4. There is no limitation to the number of CROs, the activities listed, the costs, and the like, that can be processed by this embodiment of the invention. A result of this standardization process is that all of the activities may be in the same format, using naming terminology that is now common to CRO2 and CRO4. All costs may be listed under commonly named categories, enabling accurate comparison of specification assumptions and costs.

Normalization Process

Figure 6:
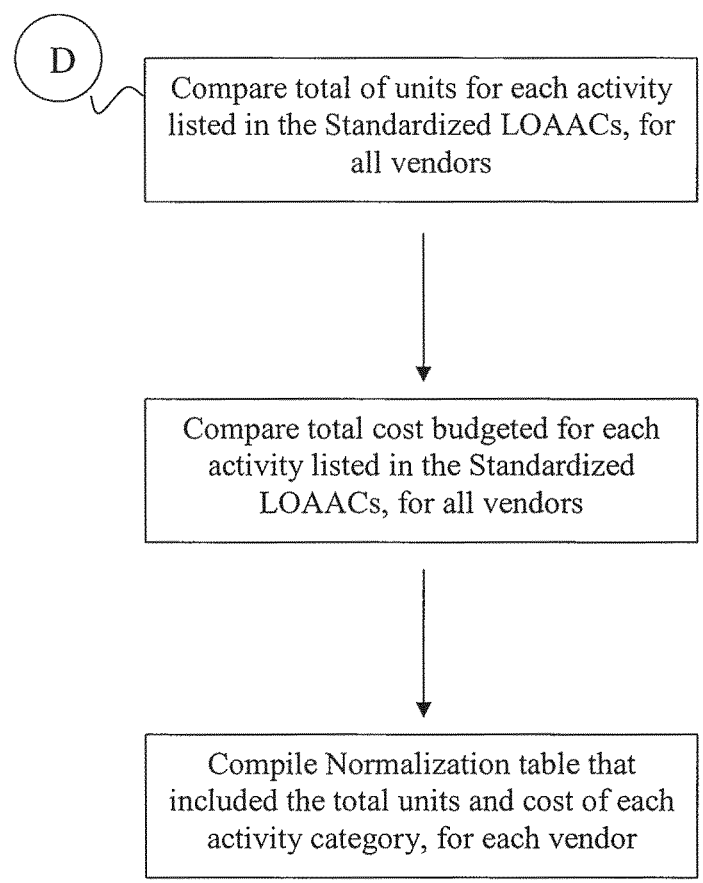
FIG. 6 illustrates a normalization process according to one preferred embodiment of the present invention.

According to an embodiment of the invention, the next step in FIG. 3 is the normalization process that provides per unit costs, to compare the activities and associated activity costs to reference assumptions. The processor can calculate per unit costs of the assumptions specifications. The preferable components of this step are illustrated in FIG. 6. A clinical trial will have assumption specifications (e.g., number of patients, number of sites, number of months to complete enrollment, total number of months for the trial, number of countries). One or more of the assumption specifications are input into the processor, which then calculates per unit costs of the assumption specifications.

According to an embodiment of the invention, this step crosschecks each LOAAC assumption specification against reference assumptions—e.g., the RFP, another iteration of a budget. Discrepancies are then preferably highlighted and deltas reported (differences between the RFP and LOAACs, for example). In addition, the normalization process may crosscheck each LOAAC unit with the unit costs, and identify discrepancies and report the deltas of the level of services. The normalization process may also crosscheck each LOAAC description of services against the units proposed to identify discrepancies and report the deltas in costs.

According to an embodiment of the invention, the normalization process then performs the following: (1) check on the feasibility of the units of activities and the costs against benchmark metrics for trials of similar size, scope, and therapeutic area; (2) reconcile all totals of units and financials—check the entire math, now that everything is standardized, calculate; and (3) display the costs and numbers of activities into units such as "cost per patient," "cost per site," "cost per page," "cost per month," and "cost per monitoring visit." This discloses that if CRO2 adds sites, for example, it will cost 'X' per site. If the trial requires more monitoring visits, the amount this will cost with each CRO, based on the LOAACs, becomes known.

According to an embodiment of the invention, the normalization report may preferably classify costs and numbers of activities into buckets such as "cost per patient," "cost per site," "cost per page," "cost per month," and "cost per monitoring visit." This can be an important guideline for watching for overruns and points for further discussion. This report may also point out differences in monitoring intervals.

According to an embodiment of the invention, the normalization process may preferably compare the total cost for the sum of activities listed in the standardized LOAACs, standard categories, for CRO2 and CRO4. A comparison may be made of the total cost budgeted for each standard category listed in the standardized LOAACs. The normalization process then preferably calculates the per unit costs so that a biotechnology company will have immediate information on the changes in the budgets that will occur based on any change in the number of units. The units are changed often in clinical trials, and a biotechnology company is usually unable to understand the resultant budget change because so many activities and associated costs are affected by a change in the trial.

Equalization Process

Figure 7:
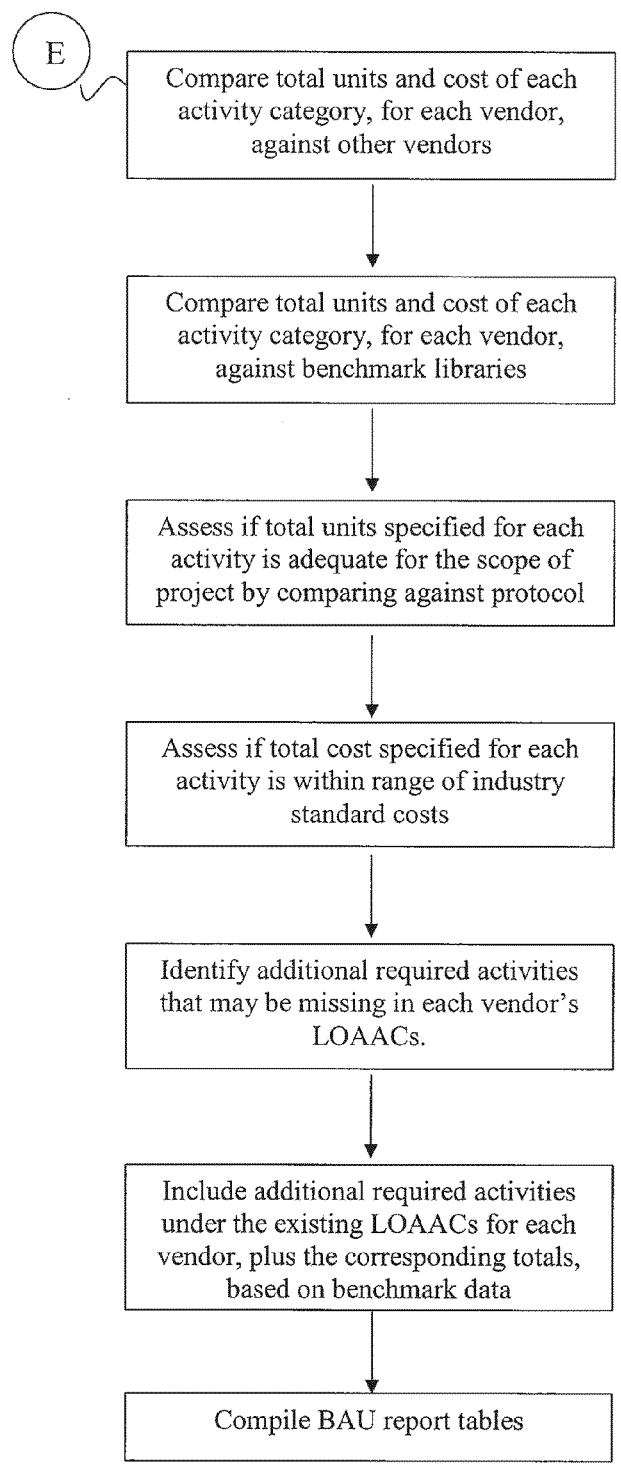
FIG. 7 illustrates an equalization process according to one preferred embodiment of the present invention.

According to an embodiment of the invention, the next step is the equalization process referenced in FIG. 3E, which equalizes the activities and the associated activity costs against reference assumption specifications (e.g., benchmark metrics, RFP, one of the CRO LOAACs), using at least the per unit costs. The preferable components of this step are illustrated in FIG. 7. The equalization process may preferably equalize the activities and the associated activity costs (LOAACs specification assumptions and costs) against reference assumption specifications, using at least the per unit costs. These reference specifications can be the RFP or benchmark specification assumptions for a trial of the same scope and therapeutic area. This step allows an accurate comparison between CRO2 and CRO4. An embodiment of the invention also provides more accurate information about the total budget because gaps in services have been identified and added to the total, as appropriate. An embodiment of the invention also has the ability to provide budget information under different budget scenarios. For example, both CRO2 and CRO4 can be equalized to any specification assumptions. A value of this capability is that reports may be provided that are preferably adjusted for other specification assumptions without having to request new cost information from CRO2 and CRO4, which can save weeks on the process.

According to an embodiment of the invention, the equalization process may preferably compare the total units and cost of each activity and category for CRO2 and CRO4 against each other. The equalization process may also compare CRO2 against benchmark metrics, as well as CRO4 against benchmark metrics. Assessment is made in an embodiment of the invention to check that activity is within the range of industry norms. The equalization process may then identify additionally required activities that may be missing in the CRO2 and CRO4 LOAACs. The cost for these additionally required activities plus the corresponding totals can then be calculated and displayed in the reports. This protects biotechnology and other companies from budget overruns later in a trial, when the surprising extra cost can adversely affect the stability of the company.

Summarizing this step of the process according to an embodiment of the invention, the activities and the associated activity costs are preferably "equalized" against reference assumptions such as benchmark metrics, using the per unit costs. These per unit costs may then be used by an embodiment of the invention to automatically compare the activities and the associated costs with the reference specifications.

In addition, according to an embodiment of the invention, normalization and equalization can be used without standardization. For example, the clinical trial budget, including assumption specifications and associated activity costs, could be analyzed by input into the process either by data entry or in an electronic format. Per unit costs of the assumption specifications are calculated by the processor, and the activities and associated costs are compared against reference assumption specifications using the per unit costs. This equalization is done if there are missing activities, or activities that are under-budgeted. The equalization evens out the budgets for comparison, such as when one budget has different factors from another budget. This may include, for example, differences in length of trial.

Reporting Process

According to an embodiment of the invention, reports that may provide information about the analysis of the budgets and comparisons of budgets are generated automatically. With the completion of each step of the process, reports may be generated based on algorithms that can preferably compare and contrast the specification assumptions and costs. Algorithms may be preferably combined with information from LOAACs to produce reports that present information that may not otherwise be attainable without significant time and expense.

Many algorithms and mathematical formulas are used during the process. Examples of these algorithms are shown in the accompanying application. There are libraries of algorithms and all formulas are enhanced as new information is added related to industry pricing, costing, and other metrics. There is no limit to the number of algorithms that the processor uses to perform the functions.

Figure 8:
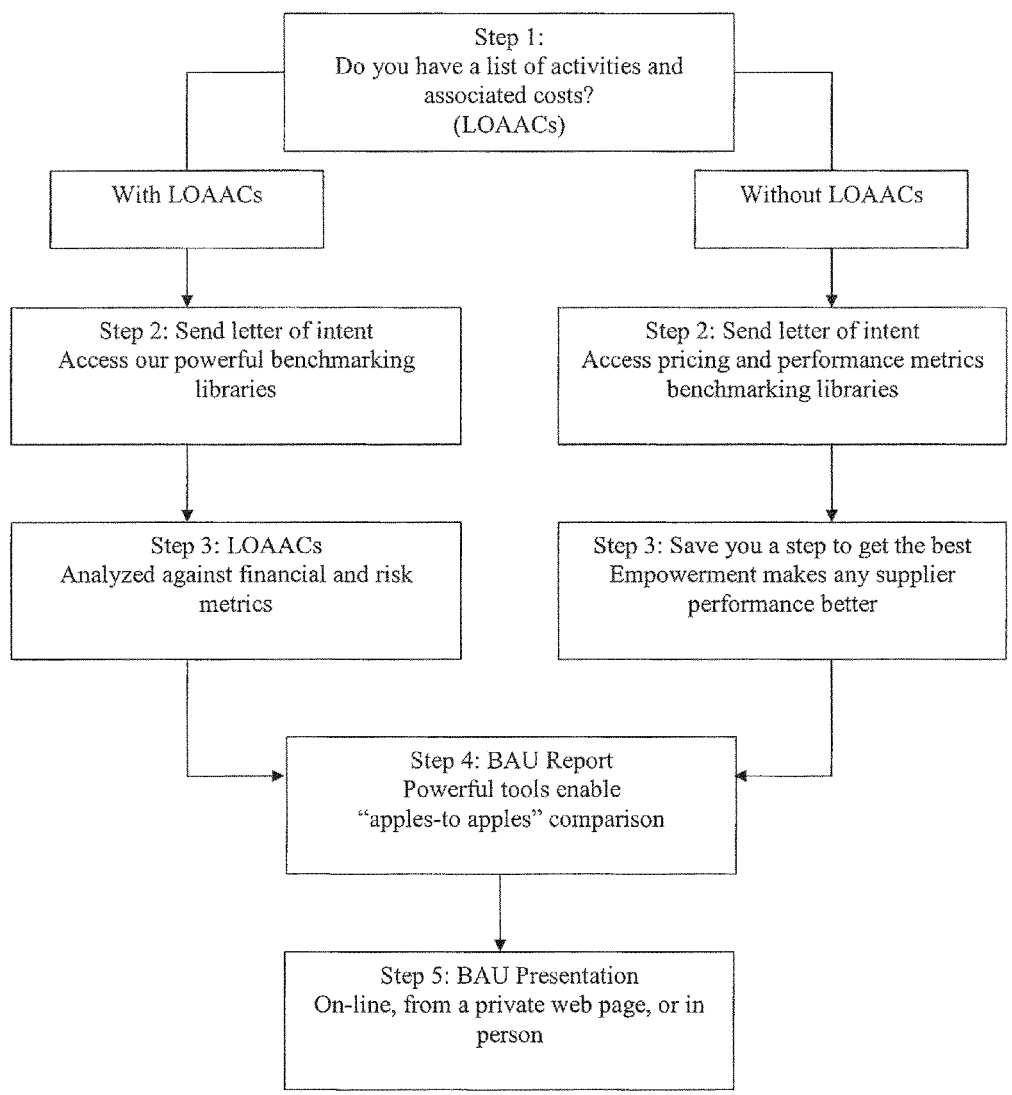
FIG. 8 is a flowchart of a process used to create a business analysis according to one preferred embodiment of the present invention.

According to an embodiment of the invention, it is not necessary for a biotechnology company to have received budgets, responses to RFPs, and LOAACs in order to perform an analysis of the budget needs for a clinical trial. FIG. 8 illustrates the direction the process takes if LOAACs are available, or when the biotechnology company wishes to use an embodiment of the invention to determine which suppliers and budgets or specifications might be appropriate for its protocol. FIG. 8 illustrates the process when the biotechnology company has available LOAACS and when it does not.

FIGS. 20, 21, 22 and 23 show examples of reports that may be produced by preferred embodiments of the present invention.

FIG. 20 is a summary of supplier differences report and analysis. The report of findings is blinded on the List Of Activities and Associated Costs to remove bias (no CRO name is included). This information is summarized for the first time. All have advantages and disadvantages, but the key is to understand these advantages and disadvantages. Scope differences, missing items, and errors in the budgets are the reason for the major discrepancy between the suppliers.

FIG. 20 report A shows a side-by-side comparison of CRO2 and CRO4 assumption specifications compared to the RFP. This report is extremely helpful to a biotech company because it highlights the assumptions that are not detailed and highlights the differences. In report A of FIG. 20, Key Variances are important deltas of differences between the RFP and LOAACs. "Not detailed" means that there is a dollar amount and some discussion of the work, but no exact specifications. This report provides information that highlights that there were no exact number of edit checks to be done, iterations of them, changes, or unit prices found by the processor in CRO2's LOAAC. There was just a dollar amount for the main activity of data management. There is no dollar amount associated with the activity, nor is there any discussion or activities mentioned in the LOAACs. 'Yes'—means activity is included, as per the costs, yet there is no number of units/specifications for the item.

Classifying costs into equivalent categories in order to enable comparability forms standardized professional fees shown in Report B of FIG. 20. The subtotal shows a huge difference in cost. The report also highlights that the costs are not inclusive. The questions that this report answers are helpful to a biotechnology company in understanding if they are getting a really good value at that low price, a really bad job, or if there is simply a misunderstanding or error about the assumptions specifications.

Report C in FIG. 20 shows adjustments to equalize specifications. The algorithms have calculations that add what is missing, and include necessary work as requested by the RFP. This section adds the activities to correct the budgets, and add the cost of activities that CROs do not include, because the work is very difficult to perform cost effectively. These activities include integrating all the information into a single, analyzable database, and the reconciliations of the data once everything is together. Reports D and E in FIG. 20 are different alternative sets of specification assumptions to run this clinical trial. These reports illustrate how the invention can quickly display the cost that would be charged by either of the CROs, if the assumption specifications were adjusted.

FIG. 21 shows the detail of differences in metrics (specification assumptions for CRO 2 and CRO 4 and as stated in the RFP. The first table in this report standardizes specifications into major categories as seen in column one: Overall Assumptions, Project Management Assumptions, Monitoring Assumptions, Data Management Assumptions, Biostats Assumptions, and Safety. These are the categories of activities that are necessary to complete the trial. This standardization and categorization sorts all supplier items into common terms so that you can compare the specifications more accurately.

The number of items, and a note where items are 'not detailed' are shown in the column for any supplier. These columns let you quickly see what is not included, or not detailed within the LOAACs. These items that are not mentioned by the supplier may be important to the trial and will be discussed more fully with them. Other items are not included in the budget, but will be needed for the trial, are listed as well. The last column in this table shows the RFP specifications.

FIG. 22A provides a report on the financial comparison, showing the dollar amounts for CRO2 and CRO4. FIG. 22B shows other expenses and their totals lined up side-by-side in the standardized categories. With these reports, a biotech can see how the dollars compare for the standard categories. Once the differences are identified, further analysis of the activities, the cost of the activities, and the assumption specifications is performed and the results are displayed in a report that details normalized costs. The normalized costs identifies that the difference in cost is because there is a very specific difference in a specific assumption specifications.

FIG. 23 shows a report that details the normalized comparator information, taken directly from the LOAACs. This report classifies costs and numbers of activities into buckets such as 'fees (costs) per patient', 'cost per site', 'cost per page', 'cost per month', and 'cost per monitoring visit'. This is an important guideline for watching for overruns, and points for further discussion. This report also points out differences in monitoring intervals and the like.

It is not clear in supplier proposals that one supplier is actually providing a lower cost project than the other. For example, looking at the fee per site, fee per patient, and fee per month (normalized) one supplier may appear higher or lower, but this may not actually be true. Monitoring visit metrics might not detail the hours per visit; therefore a complete comparison cannot be made.

Figure 24:
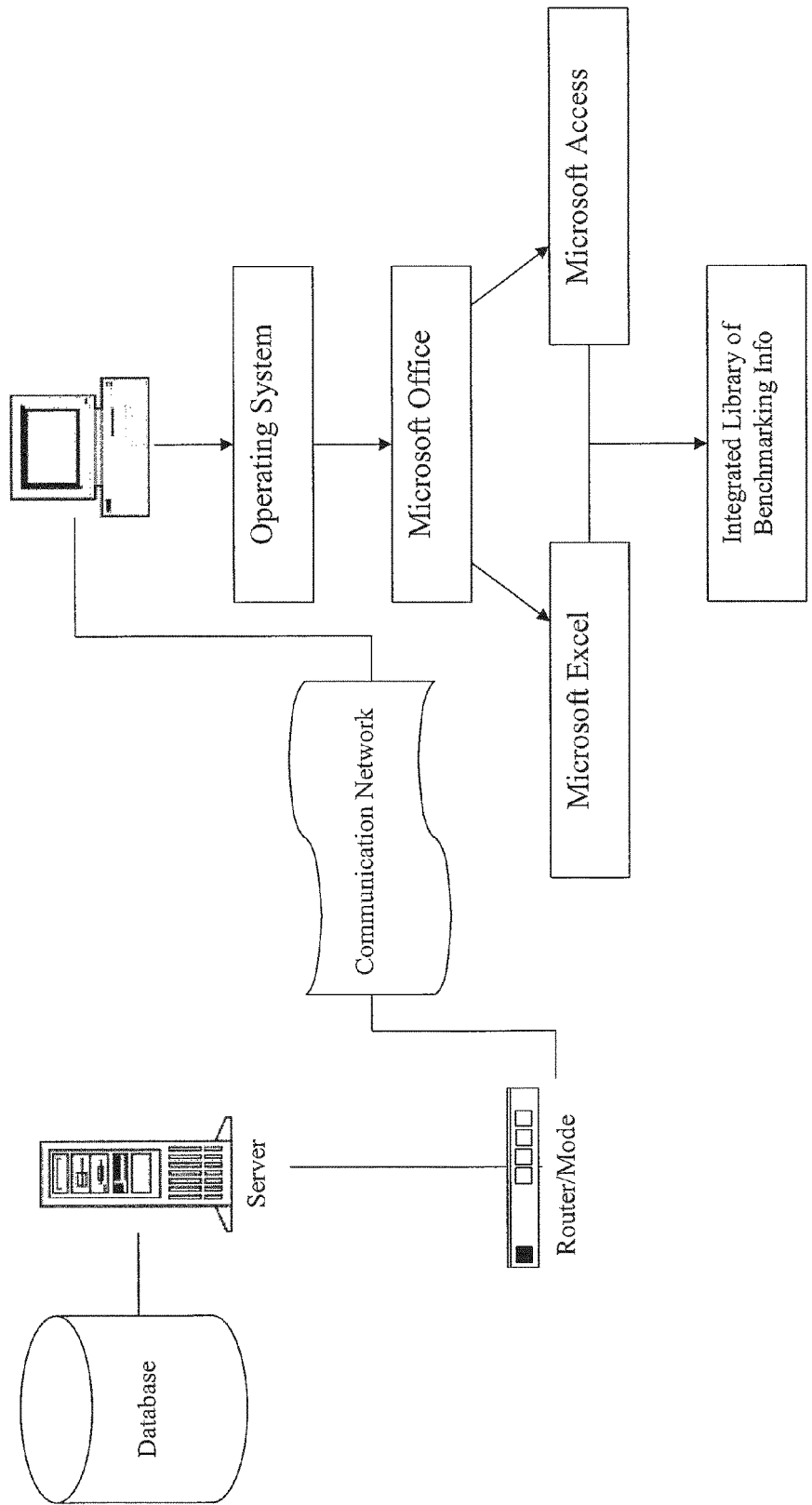
FIG. 24 is a hardware configuration diagram in accordance with one preferred embodiment of the present invention.

FIG. 24 is a hardware configuration diagram for the current embodiment of the invention.

FIGS. 25A1-25G2, taken together, list the algorithms and the formulas used by the processor to calculate and produce all of the information in the reports and the formatted reports as well. These formulas and algorithms allow the processor to accept input and calculate and display standardized comparisons of the CRO LOAACs or RFP responses with the reference specifications (e.g., benchmark metrics and benchmarking metrics). Reference activities and costs are also calculated and displayed for analysis and comparisons for costs and assumption specification references. The preferred embodiment of the present invention also provides the assumptions specifications and the costs, both normalized and equalized. FIG. 25A is illustrated in two parts, FIGS. 25A1 and 25A2, indicating that this figure is larger than the page.

According to an embodiment of the invention, the content of a complete generated report may comprises one or more of the following:

Clinical Operations Information
 1. Risk management analysis
 2. Responsibilities clearly delineated
Data Consolidation
 1. Integration control charts
 2. Reporting controls
 3. Performance metric tracking
 4. Replacement of faulty suppliers
Financial Risk Analysis & Controls
 1. Analysis Summary of Supplier Cost Differences
 2. Normalized Costs Comparator Information—Apples-to-Apples
 3. Details of Best-of-Breed suppliers and activities
 4. Recommendations to avoid delays and budget overruns
 5. Forms the basis of time and cost guarantees
Case Study As seen in FIG. 26, the analysis and reports have a tremendous impact on the project budget. This figure shows three actual examples from recent actual clinical trials completed. The magnitude of the cost avoided is significant and this process has been able to consistently demonstrate where there are substantial cost savings (averaging over 30%) attainable.

FIG. 27 shows an example of the cover page of output in accordance with one preferred embodiment of the present invention.

FIG. 28 is an excerpt of the output that illustrates money saved by performing this process. This process saves time and eliminates waste and inefficiencies. The biotechnology company is assured that they get speed and protection, with no additional costs.

Figure 29:
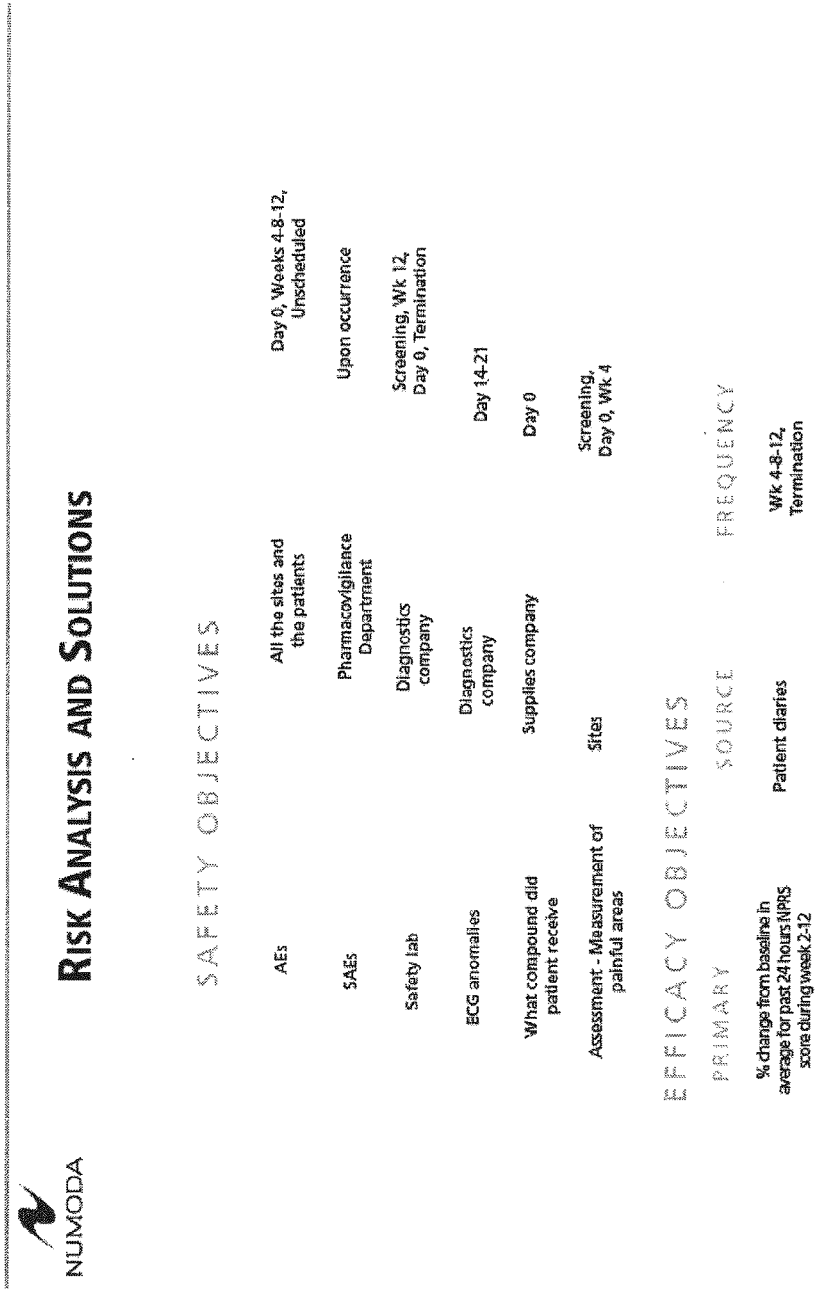

FIG. 29 shows an output that includes an analysis of risk based on the objectives of a particular trial using benchmark metrics.

The analysis includes a risk matrix calculation that provides the comfort and security that levels of exposure have been identified and analyzed. This analysis is specific to the points of risk of the trial and is seen in FIG. 30.

FIG. 31 gives the biotechnology company a calculation of several options and their effect on risk mitigation in enrollment, drug supply inventory, and the like.

FIG. 32 shows the comparison, of four alternatives in standardized categories as seen on the left. For example: Overall Assumptions, Project Management, Monitoring. Columns to the right quantifies units for each category. This reveals what is not included or not detailed. This standardization is not easy to make. The current embodiment of the invention provides this information. Importantly, reducing the scope, or reducing protections does not accomplish cost savings.

FIG. 33 shows dollars reclassified into standardized categories. This report revealed that although the total project budget appears similar, there are huge discrepancies within the categories. For example, monitoring activities vary from $454,000 to $1.2 million. There is an almost $1 million difference between the highest and lowest costs. Different suppliers treat passthrough costs (another category of activity costs) very differently, which can result in budget overruns.

FIG. 34 is an example of commentary and recommendations that accompany the other financial and risk reports.

FIG. 35 shows a report with per unit costs that compares vendors based on normalized costs. The gross monitoring cost per visit varies greatly between CRO1 and CRO2 EDC (electronic data capture). There are significant differences between the supplier who bid with less sites and/or a high unit cost. This lets the biotechnology company know how unit costs vary and who offers the best value.

FIG. 36 is a report of responsibilities and costs. It shows precisely who is doing what activities and itemizes each component and the responsible party. This shows the total budget with total transparency. These reports tie in to the reconciliations of costs during the conduct of the trial.

The present invention may be implemented with any combination of hardware and software. If implemented as a computer-implemented apparatus, the present invention is implemented using means for performing all of the steps and functions described above.

The present invention can be included in an article of manufacture (e.g., one or more computer program products) having, for instance, computer useable media. The media is encoded with, for instance, computer readable program code means for providing and facilitating the mechanisms of the present invention. The article of manufacture can be included as part of a computer system or sold separately.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

What is claimed is:

1. An electronic method of analyzing budgets for clinical trials, the method comprising:
    (a) inputting a previously defined clinical trial budget into a processor, the previously defined budget including activities and associated activity costs of a clinical trial;
    (b) automatically classifying, using the processor, the activities of the previously inputted clinical trial budget into a set of standardized service categories, wherein an electronic translator that includes a dictionary of clinical trial activities and their associated standardized service categories is used to automatically perform at least some of the classifying;
    (c) electronically allocating, using the processor, the associated activity costs with the respective standardized service category so that budget costs of the clinical trial can be objectively analyzed; and
    (d) outputting a report of the associated activity costs with the respective standardized service category for use in analyzing budgets for clinical trials.

2. The method of claim 1 wherein the clinical trial further includes a set of assumption specifications of the clinical trial, the method further comprises:
    (e) inputting the set of assumption specifications into the processor, the assumption specifications including at least the number of patients involved in the clinical trial;
    (f) calculating per unit costs of the assumption specifications; and
    (g) outputting a report of the per unit costs of the assumption specifications for use in analyzing budgets for clinical trials.

3. The method of claim 2 further comprising:
    (h) equalizing the activities and the associated activity costs against reference assumption specifications based on at least the per unit costs; and
    (i) outputting a report of the equalized activity costs for use in analyzing budgets for clinical trials.

4. The method of claim 2 further comprising:
    (h) using the per unit costs to compare the activities and the associated activity costs to reference assumption specifications.

5. The method of claim 1 wherein steps (a)-(d) are performed for a plurality of budgets for the same clinical trial, the method further comprising:
    (e) generating, using the processor, a comparison report showing at least some of the standardized service categories and the associated activity costs for each of the plurality of budgets.

6. The method of claim 1 wherein the activities include at least monitoring of clinical investigator sites that are conducting the clinical trial.

7. An electronic method of analyzing budgets for clinical trials, the method comprising:
    (a) inputting a previously defined clinical trial budget into a processor, the budget including assumption specifications of a clinical trial, activities of the clinical trial, and associated activity costs of the clinical trial;
    (b) calculating in the processor per unit costs of the assumption specifications of the previously inputted budget;
    (c) equalizing the activities and the associated activity costs against reference assumption specifications using at least the per unit costs via calculations performed in the processor so that budget costs of the clinical trial can be objectively analyzed; and
    (d) outputting at least one of (i) a report of the per unit costs of the assumption specifications, and (ii) a report of the equalized activity costs, for use in analyzing budgets for a clinical trial.

8. The method of claim 7 wherein the activities include at least monitoring of clinical investigator sites that are conducting the clinical trial, and the assumption specifications include at least the number of patients involved in the clinical trial.

9. The method of claim 7 wherein steps (a)-(d) are performed for a plurality of budgets for the same clinical trial, the method further comprising:
    (e) generating, using the processor, a comparison report showing at least some of the activities and the associated activity costs for each of the plurality of budgets.

10. An article of manufacture for analyzing budgets for clinical trials, the article of manufacture comprising a non-transitory computer-readable medium encoded with computer-executable instructions for performing the steps of:
    (a) inputting a previously defined clinical trial budget into a processor, the previously defined budget including activities and associated activity costs of a clinical trial;
    (b) automatically classifying, using the processor, the activities of the previously inputted clinical trial budget into a set of standardized service categories, wherein an electronic translator that includes a dictionary of clinical trial activities and their associated standardized service categories is used to automatically perform at least some of the classifying;
    (c) electronically allocating, using the processor, the associated activity costs with the respective standardized service category so that budget costs of the clinical trial can be objectively analyzed; and
    (d) outputting a report of the associated activity costs with the respective standardized service category for use in analyzing budgets for clinical trials.

11. The article of manufacture of claim 10 wherein the clinical trial further includes a set of assumption specifications of the clinical trial, and the computer-readable medium is encoded with computer-executable instructions for performing the further steps of:
    (e) inputting the set of assumption specifications into the processor, the assumption specifications including at least the number of patients involved in the clinical trial;
    (f) calculating per unit costs of the assumption specifications; and
    (g) outputting a report of the per unit costs of the assumption specifications for use in analyzing budgets for clinical trials.

12. The article of manufacture of claim 11 wherein the computer-readable medium is encoded with computer-executable instructions for performing the further step of:
    (h) equalizing the activities and the associated activity costs against reference assumption specifications based on at least the per unit costs; and
    (i) outputting a report of the equalized activity costs for use in analyzing budgets for clinical trials.

13. The article of manufacture of claim 11 wherein the computer-readable medium is encoded with computer-executable instructions for performing the further step of:

(h) using the per unit costs to compare the activities and the associated activity costs to reference assumption specifications.

14. The article of manufacture of claim 10 wherein steps (a)-(d) are performed for a plurality of budgets for the same clinical trial, the method further comprising:
   (e) generating, using the processor, a comparison report showing at least some of the standardized service categories and the associated activity costs for each of the plurality of budgets.

15. The article of manufacture of claim 10 wherein the activities include at least monitoring of clinical investigator sites that are conducting the clinical trial.

16. An article of manufacture for analyzing budgets for clinical trials, the article of manufacture comprising a non-transitory computer-readable medium encoded with computer-executable instructions for performing the steps of:
   (a) inputting a previously defined clinical trial budget into a processor, the budget including assumption specifications of a clinical trial, activities of the clinical trial, and associated activity costs of the clinical trial;
   (b) calculating in the processor per unit costs of the assumption specifications of the previously inputted budget;
   (c) equalizing the activities and the associated activity costs against reference assumption specifications using at least the per unit costs via calculations performed in the processor so that budget costs of the clinical trial can be objectively analyzed; and
   (d) outputting at least one of (i) a report of the per unit costs of the assumption specifications, and (ii) a report of the equalized activity costs, for use in analyzing budgets for a clinical trial.

17. The article of manufacture of claim 16 wherein the activities include at least monitoring of clinical investigator sites that are conducting the clinical trial, and the assumption specifications include at least the number of patients involved in the clinical trial.

18. The article of manufacture of claim 16 wherein steps (a)-(d) are performed for a plurality of budgets for the same clinical trial, the method further comprising:
   (e) generating, using the processor, a comparison report showing at least some of the activities and the associated activity costs for each of the plurality of budgets.

* * * * *